(12) United States Patent
Beaulieu et al.

(10) Patent No.: US 8,242,140 B2
(45) Date of Patent: Aug. 14, 2012

(54) VIRAL POLYMERASE INHIBITORS

(75) Inventors: Pierre L. Beaulieu, Laval (CA); Paul J. Edwards, Laval (CA); Martin Poirier, Laval (CA); Jean Rancourt, Laval (CA); Timothy A. Stammers, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 152 days.

(21) Appl. No.: 12/671,780

(22) PCT Filed: Jul. 31, 2008

(86) PCT No.: PCT/CA2008/001412
§ 371 (c)(1),
(2), (4) Date: Mar. 1, 2010

(87) PCT Pub. No.: WO2009/018657
PCT Pub. Date: Feb. 12, 2009

(65) Prior Publication Data
US 2010/0190779 A1    Jul. 29, 2010

Related U.S. Application Data

(60) Provisional application No. 60/953,701, filed on Aug. 3, 2007.

(51) Int. Cl.
*A61K 31/444* (2006.01)
(52) U.S. Cl. .................. 514/335; 546/261; 546/262
(58) Field of Classification Search .......... 546/261, 546/262
See application file for complete search history.

(56) References Cited

U.S. PATENT DOCUMENTS

| | | | |
|---|---|---|---|
| 4,062,682 A | 12/1977 | Laridon et al. | |
| 4,740,519 A | 4/1988 | Shroot et al. | |
| 5,633,388 A | 5/1997 | Diana et al. | |
| 6,434,489 B1 | 8/2002 | Lesburg et al. | |
| 6,448,281 B1 | 9/2002 | Beaulieu et al. | |
| 6,479,508 B1 | 11/2002 | Beaulieu et al. | |
| 6,794,404 B2 | 9/2004 | Beaulieu et al. | |
| 6,878,727 B2 | 4/2005 | Borchardt et al. | |
| 6,927,225 B2 * | 8/2005 | Ricks et al. ............ | 514/335 |
| 7,074,784 B2 | 7/2006 | Goldmann et al. | |
| 7,112,600 B1 | 9/2006 | Hashimoto et al. | |
| 7,157,486 B2 | 1/2007 | Beaulieu et al. | |
| 7,223,785 B2 | 5/2007 | Beaulieu et al. | |
| 7,238,725 B2 | 7/2007 | Balasubramanian et al. | |
| 7,386,398 B2 | 6/2008 | Coulombe et al. | |
| 7,816,348 B2 | 10/2010 | Coulombe et al. | |
| 7,897,622 B2 | 3/2011 | Beaulieu et al. | |
| 2003/0236251 A1 | 12/2003 | Beaulieu et al. | |
| 2004/0082635 A1 | 4/2004 | Hashimoto et al. | |
| 2004/0110126 A1 | 6/2004 | Kukolj et al. | |
| 2004/0224955 A1 | 11/2004 | Beaulieu et al. | |
| 2005/0003348 A1 | 1/2005 | Coulombe et al. | |
| 2006/0004197 A1 | 1/2006 | Thrash et al. | |
| 2006/0052418 A1 | 3/2006 | Beaulieu et al. | |
| 2006/0160798 A1 | 7/2006 | Beaulieu et al. | |
| 2006/0189672 A1 | 8/2006 | Poupart et al. | |
| 2006/0293306 A1 | 12/2006 | Beaulieu et al. | |
| 2007/0219176 A1 | 9/2007 | Coulombe et al. | |
| 2008/0045516 A1 | 2/2008 | Beaulieu et al. | |
| 2008/0114068 A1 | 5/2008 | Simoneau et al. | |
| 2008/0146539 A1 | 6/2008 | Priepke et al. | |
| 2010/0190779 A1 | 7/2010 | Beaulieu et al. | |
| 2010/0273651 A1 | 10/2010 | Dietz et al. | |
| 2010/0286131 A1 | 11/2010 | Beaulieu et al. | |
| 2010/0311581 A1 | 12/2010 | Dietz et al. | |
| 2010/0317515 A1 | 12/2010 | Dietz et al. | |
| 2011/0021486 A1 | 1/2011 | Beaulieu et al. | |

FOREIGN PATENT DOCUMENTS

| | | |
|---|---|---|
| CA | 2412718 A1 | 1/2002 |
| CA | 2450033 A1 | 2/2003 |
| CA | 2511301 A1 | 8/2004 |
| EP | 1256628 A2 | 11/2002 |
| EP | 1688420 A1 | 8/2006 |
| WO | 9118591 A1 | 12/1991 |
| WO | 9827108 A2 | 6/1998 |
| WO | 9907733 A2 | 2/1999 |
| WO | 9907734 A2 | 2/1999 |
| WO | 9949830 A2 | 10/1999 |
| WO | 0009543 A2 | 2/2000 |
| WO | 0009558 A1 | 2/2000 |
| WO | 0059929 A1 | 10/2000 |
| WO | 0114339 A2 | 3/2001 |

(Continued)

OTHER PUBLICATIONS

International Search Report, Form PCT/ISA/210, for corresponding PCT/CA2008/001412; date of mailing: Oct. 23, 2008.
Abdel-Magid, A.F., et al., "Reductive Amination of Aldehydes and Ketones with Sodium Triacetoxyborohydride. Studies on Direct and Indirect Reductive Amination Procedures", J. Org. Chem., 1996, vol. 61, p. 3849.
Abstract in English for WO1999049830 which is in the German language. Publication date: 1999.
Abstract in English for WO2009077497 which is in the German language. Publication Date: 2009.
Ago, H.,et al. "Crystal Structure of the RNA-dependent RNA Polymerase of Hepatitis C Virus", Structure, vol. 7, No. 11, pp. 1417-1426, USA, Nov. 1999.

(Continued)

*Primary Examiner* — James O Wilson
*Assistant Examiner* — Brian McDowell
(74) *Attorney, Agent, or Firm* — Michael P. Morris; Philip I. Datlow

(57) ABSTRACT

Compounds of formula I:

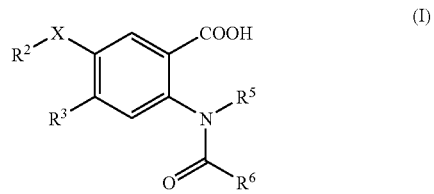

wherein X, $R^2$, $R^3$, $R^5$ and $R^6$ are defined herein, are useful as inhibitors of the hepatitis C virus NS5B polymerase.

11 Claims, No Drawings

FOREIGN PATENT DOCUMENTS

| | | |
|---|---|---|
| WO | 0147883 | 7/2001 |
| WO | 0177113 A2 | 10/2001 |
| WO | 0181325 A2 | 11/2001 |
| WO | 0204425 A2 | 1/2002 |
| WO | 0208187 A1 | 1/2002 |
| WO | 0208198 A2 | 1/2002 |
| WO | 0208244 A2 | 1/2002 |
| WO | 0208256 A2 | 1/2002 |
| WO | 0248172 A2 | 6/2002 |
| WO | 02060926 A2 | 8/2002 |
| WO | 03000254 | 1/2003 |
| WO | 03004458 A1 | 1/2003 |
| WO | 03007945 A1 | 1/2003 |
| WO | 03010140 A2 | 2/2003 |
| WO | 03010141 A2 | 2/2003 |
| WO | 03026587 | 4/2003 |
| WO | 03053349 A2 | 7/2003 |
| WO | 03062228 A1 | 7/2003 |
| WO | 03062265 A2 | 7/2003 |
| WO | 03064416 A1 | 8/2003 |
| WO | 03064455 A2 | 8/2003 |
| WO | 03064456 A1 | 8/2003 |
| WO | 03099274 A1 | 12/2003 |
| WO | 03099316 A1 | 12/2003 |
| WO | 03101993 | 12/2003 |
| WO | 2004030670 A1 | 4/2004 |
| WO | 2004032827 A2 | 4/2004 |
| WO | 2004037855 A1 | 5/2004 |
| WO | 2004039833 A1 | 5/2004 |
| WO | 2004043339 A2 | 5/2004 |
| WO | 2004064925 A1 | 8/2004 |
| WO | 2004065367 A1 | 8/2004 |
| WO | 2004072243 A2 | 8/2004 |
| WO | 2004087714 | 10/2004 |
| WO | 2004093798 A2 | 11/2004 |
| WO | 2004094452 A2 | 11/2004 |
| WO | 2004099241 A1 | 11/2004 |
| WO | 2004101602 A2 | 11/2004 |
| WO | 2004101605 A1 | 11/2004 |
| WO | 2004103996 A1 | 12/2004 |
| WO | 2004113365 A2 | 12/2004 |
| WO | 2005010029 A1 | 2/2005 |
| WO | 2005012288 A1 | 2/2005 |
| WO | 2005014543 | 2/2005 |
| WO | 2005021584 A2 | 3/2005 |
| WO | 2005028501 A1 | 3/2005 |
| WO | 2005030796 A1 | 4/2005 |
| WO | 2005037214 A2 | 4/2005 |
| WO | 2005046712 A1 | 5/2005 |
| WO | 2005049622 A1 | 6/2005 |
| WO | 2005051410 A1 | 6/2005 |
| WO | 2005051980 A1 | 6/2005 |
| WO | 2005054430 A2 | 6/2005 |
| WO | 2005058821 A1 | 6/2005 |
| WO | 2005070955 A1 | 8/2005 |
| WO | 2005080388 A1 | 9/2005 |
| WO | 2005085197 A1 | 9/2005 |
| WO | 2005085242 A1 | 9/2005 |
| WO | 2005085275 A1 | 9/2005 |
| WO | 2005087721 A2 | 9/2005 |
| WO | 2005087725 A2 | 9/2005 |
| WO | 2005087730 A1 | 9/2005 |
| WO | 2005087731 A1 | 9/2005 |
| WO | 2005107745 A1 | 11/2005 |
| WO | 2005113581 A1 | 12/2005 |
| WO | 2005121132 A1 | 12/2005 |
| WO | 2006000085 A1 | 1/2006 |
| WO | 2006007693 A1 | 1/2006 |
| WO | 2006007700 A1 | 1/2006 |
| WO | 2006007708 A1 | 1/2006 |
| WO | 2006014405 A2 | 2/2006 |
| WO | 2006049304 A1 | 5/2006 |
| WO | 2007014922 A1 | 2/2007 |
| WO | 2007087717 A1 | 8/2007 |
| WO | 2008019477 A1 | 2/2008 |
| WO | 2009010783 A1 | 1/2009 |
| WO | 2009018656 A1 | 2/2009 |
| WO | 2009018657 A1 | 2/2009 |
| WO | 2009076747 A1 | 6/2009 |
| WO | 2009077443 A2 | 6/2009 |
| WO | 2009077471 A2 | 6/2009 |
| WO | 2009077497 A2 | 6/2009 |
| WO | 2009077500 A2 | 6/2009 |
| WO | 2009077608 A1 | 6/2009 |
| WO | 2009080637 A1 | 7/2009 |
| WO | 2009085230 A1 | 7/2009 |
| WO | 2009085584 A1 | 7/2009 |
| WO | 2009085816 A1 | 7/2009 |
| WO | 2009085983 A1 | 7/2009 |
| WO | 2010037210 A1 | 4/2010 |

OTHER PUBLICATIONS

Beaulieu et al., Inhibitors of the HCV NS5B polymerase: New hope for the treatment of hepatitis C infections, "Current Opinion in Investigational Drugs" vol. 5 (8) pp. 838-850, 2004 (abstract and discussion).

Beaulieu et al, Non-nucleoside inhibitors of the hepatitis C virus NS5B polymerase: discovery of benzimidazole 5-carboxylic amide derivatives with low-nanomolar potency, "Biorganic & Medicinal Chemistry Letters" vol. 14 (4) pp. 967-971 (2004) (abstract and discussion).

Beaulieu, P. L., "Finger loop inhibitors of the HCV NS5B polymerase: Discovery and prospects for new HCV therapy", Curr. Opin. Drug Discovery & Development, 2006, vol. 9, No. 5, p. 618.

Beaulieu, P. L., "Non-nucleoside inhibitors of the HCV NS5B polymerase: Progress in the discovery and development of novel agents for the treatment of HCV infections", Curr. Opin. Investigational Drugs, 2007, vol. 8, No. 8, p. 614.

Beaulieu, P. L., "The discover of finger loop inhibitors of the hepatitis C virus NS5B polymerase: Status and prospects for novel HCV therapeutics", IDRUGS, 2006, vol. 9, No. 1, p. 39.

Berge, S. M., et al., "Pharmaceutical Salts", Journal of Pharmaceutical Sciences, 1977, vol. 66, No. 1, p. 1.

Bowie, et al., "Deciphering the message in protein sequences: tolerance to amino acide substitutions". Science, vol. 247, No. 4948, Mar. 1990, pp. 1306-1310.

Bressanelli, S., et al. "Crystal Structure of the RNA-dependent RNA Polymerase of Hepatitis C Virus", PNAS, vol. 96, No. 23, pp. 13034-13039, USA, Nov. 1999.

Bressanelli, S., et al. "Structural Analysis of the Hepatitis C Virus RNA Polymerase in Complex with Ribonucleotides", J. Virology. vol. 76, No. 7, pp. 3482-3492, USA, Apr. 2002.

Buck, E., et al., "Preparation of 1-Methoxy-2-(4-Methoxyphenoxy) Benzene", Org. Syntheses, 2005, vol. 82, p. 69.

CAPLUS: Hemalatha, R. et al., "QSAR Analysis of 5-substituted-2-Benzoylaminobenzoic acids as PPAR Modulator", E-Journal of Chemistry, 2004, vol. 1, No. 5, p. 243-250S.

Di Marco, S., et al., "Interdomain Communication in Hepatitis C Virus Polymerase Abolished by Small Molecule Inhibitors Bound to a Novel Allosteric Site", J. Biological Chemistry, 2005, vol. 280, No. 33, p. 29765.

Faucher et al., Synthesis of BILN 2061, an HCV NS3 Protease Inhibitor with Proven Antiviral Effect in Humans, "Organic Letters" vol. 6 (17) pp. 2901-2904, 2004 (abstract and discussion).

Giuliano, C. et al., "Preclinical pharmacokinetics and metabolism of a potent non-nucleoside inhibitor of the hepatitis C virus NS5B polymerase" Xenobiotica, 2005, vol. 35, No. 10, p. 1035.

Harper, S. et al., "Development and Preliminary Optimization of Indole-N-Acetamide Inhibitors of Hepatitis C Virus NS5B Polymerase", J. Medicinal Chemistry, 2005, vol. 48, p. 1314.

Harper,S., et al., "Potent Inhibitors of Subgenomic Hepatitis C Virus RNA Replication through Optimization of Indole-N-Acetamide Allosteric inhibitors of the Viral NS5B polymerase", J. Medicinal Chemistry, 2005, vol. 48, p. 454.

Hemalatha, et al., "QSAR Analysis of 5-substituted-2-benzoylaminobenzoic acids as PPAR Modulator," E-Journal of Chemistry, vol. 1, No. 5, 2004, pp. 243-250.

Hennessy, E.J., et al., "A General and Mild Copper-Catalyzed Arylation of Diethyl Malonate", Organic Letters, 2002, vol. 4, No. 2, p. 269.

Illinois Department of Public Health, HCV, 2011. http://www.idph.state.il.us/public/hb/hbhepc.htm.

Khoshtariya, T.E. et al., "Condensed Tetracyclic Systems with an ISATIN Fragment in the Molecule". Chemistry of Heterocyclic Compounds, vol. 43, No. 9, 2007, p. 1111-1117.

Kolykhalov, A.A., et al., "Hepatitis C Virus-Encoded Enzymatic Activities and Conserved RNA Elements in the 3' Nontranslated Region are Essential for Virus Replication in Vivo", J. Virology, 2000, vol. 74, No. 4, p. 2046.

Labonte, P. et al. "Modulation of Hepatitis C Virus RNA-dependent RNA Polymerase Activity by Structure-based Site-directed Mutagenesis", J. Bio. Chem. vol. 277, No. 41, Issue of Oct. 11, pp. 38838-38846, USA, 2002.

Lesburg, C. A., et al. "Crystal Structure of the RNA-dependent RNA Polymerase from Hepatitis C Virus Reveals a Fully Encircled Active Site", Nature Structural Biology, vol. 6, No. 10, pp. 937-943, USA, Oct. 1999.

Llinas-Brunet et al., Highly Potent and Selective Peptide-Based Inhibitors of the Hepatitis C virus Serine Protease: Towards Smaller Inhibitors, "Bioorganic & Medicinal Chemistry Letters" vol. 10 (20) pp. 2267-2270, 2000 (abstract and discussion).

McKercher, G., et al., "Specific inhibitors of HCV polymerase identified using an NS5B with lower affinity for template/primer substrate", Nucleic Acids Res., 2004, vol. 32, No. 2, p. 422.

Oestberg, T. et al., "A New Class of Peroxisome Proliferator-activated Receptor Agonists with a novel Binding Epitope Shows Antidiabetic Effects", J. Biological Chemistry, 2004, vol. 279, No. 39, p. 41124.

Still, W.C., et al., "Rapid Chromatographic Technique for Preparative Separations with Moderate Resolution", J. Org. Chem., 1978, vol. 43, No. 14, p. 2923.

Takagi, K., "Synthesis of Aromatic Thiols from Aryl Iodides and Thiourea by Means of Nickel Catalyst", Chemistry Letters, 1985, p. 1307.

Tanaka, K. et al., "Synthesis and Reaction of 5-Amino-3-trifluoromethylisoxazole and -pyrazole-4-carboxylic Acids", J. Heterocyclic Chem., 1986, vol. 23, p. 1535.

Thor, M., et al., "Synthesis and Pharmacological Evaluation of a New Class of Peroxisome Proliferator-Activated Receptor Modulators", Bioorganic and Medicinal Chemistry Letters, 2002, vol. 12, p. 3565.

Tomei, L., et al. "Mechanism of Action and Antiviral Activity of Benzimidazole-Based Allosteric Inhibitors of the Hepatitis C Virus RNA-Dependent RNA Polymerase" Journal of Virology, vol. 77, No. 24, pp. 13225-13231, USA, Dec. 2003.

Zurawski, et al., "Definition and spatial locatin of mouse interleukin-2-residues that interact with its heterotrimeric receptor." The EMBO Journal, vol. 12, No. 13, Dec. 1993, pp. 5113-5119.

Lohmann, V. et al., "Replication of Subgenomic Hepatitis C Virus RNAa i a Hepatoma Cell Line". Science, vol. 285, 1999, p. 110-113.

Coulombe et al.; CAS 147:234873; WO2007087717; PCT International Appl.; 2007.

Chilean International Search Report for Chilean Patent Appln 03819-2008 issued on Jul. 6, 2011.

Hepatitis C New Drug Pipeline, New drugs in development for the treatment of hepatitis C. http://hcvdrugs.com (Jun. 15, 2011).

* cited by examiner

```
                       SEQUENCE LISTING

<160> NUMBER OF SEQ ID NOS: 1

<210> SEQ ID NO 1
<211> LENGTH: 591
<212> TYPE: PRT
<213> ORGANISM: Artificial Sequence
<220> FEATURE:
<223> OTHER INFORMATION: HCV NS5B

<400> SEQUENCE: 1

Met Gly Ser Ser His His His His His His Ser Ser Gly Leu Val Pro
 1               5                  10                  15

Arg Gly Ser His Met Ser Met Ser Tyr Thr Trp Thr Gly Ala Leu Ile
                20                  25                  30

Thr Pro Cys Ala Ala Glu Glu Ser Gln Leu Pro Ile Asn Ala Leu Ser
             35                  40                  45

Asn Ser Leu Val Arg His Arg Asn Met Val Tyr Ser Thr Thr Ser Arg
         50                  55                  60

Ser Ala Ala Leu Arg Gln Lys Lys Val Thr Phe Asp Arg Leu Gln Val
 65                  70                  75                  80

Leu Asp Asp His Tyr Arg Asp Val Leu Lys Glu Met Lys Ala Lys Ala
                 85                  90                  95

Ser Thr Val Lys Ala Lys Leu Leu Ser Val Glu Glu Ala Cys Lys Leu
                100                 105                 110

Thr Pro Pro His Ser Ala Lys Ser Lys Phe Gly Tyr Gly Ala Lys Asp
            115                 120                 125

Val Arg Asn Leu Ser Ser Lys Ala Val Asp His Ile Arg Ser Val Trp
        130                 135                 140
```

```
Lys Asp Leu Leu Glu Asp Thr Glu Thr Pro Ile Asp Thr Thr Ile Met
145                 150                 155                 160

Ala Lys Asn Glu Val Phe Cys Val Gln Pro Glu Lys Gly Gly Arg Lys
                165                 170                 175

Pro Ala Arg Leu Ile Val Phe Pro Asp Leu Gly Val Arg Val Cys Glu
            180                 185                 190

Lys Met Ala Leu Tyr Asp Val Val Ser Thr Leu Pro Gln Ala Val Met
        195                 200                 205

Gly Ser Ser Tyr Gly Phe Gln Tyr Ser Pro Lys Gln Arg Val Glu Phe
    210                 215                 220

Leu Val Asn Ala Trp Lys Ser Lys Lys Cys Pro Met Gly Phe Ser Tyr
225                 230                 235                 240

Asp Thr Arg Cys Phe Asp Ser Thr Val Thr Glu Ser Asp Ile Arg Val
                245                 250                 255

Glu Glu Ser Ile Tyr Gln Cys Cys Asp Leu Ala Pro Glu Ala Arg Gln
                260                 265                 270

Ala Ile Lys Ser Leu Thr Glu Arg Leu Tyr Ile Gly Gly Pro Leu Thr
            275                 280                 285

Asn Ser Lys Gly Gln Asn Cys Gly Tyr Arg Arg Cys Arg Ala Ser Gly
        290                 295                 300

Val Leu Thr Thr Ser Cys Gly Asn Thr Leu Thr Cys Tyr Leu Lys Ala
305                 310                 315                 320

Ser Ala Ala Cys Arg Ala Ala Lys Leu Gln Asp Cys Thr Met Leu Val
                325                 330                 335

Asn Gly Asp Asp Leu Val Val Ile Cys Glu Ser Ala Gly Thr Gln Glu
            340                 345                 350

Asp Ala Ala Asn Leu Arg Val Phe Thr Glu Ala Met Thr Arg Tyr Ser
        355                 360                 365

Ala Pro Pro Gly Asp Leu Pro Gln Pro Glu Tyr Asp Leu Glu Leu Ile
    370                 375                 380

Thr Ser Cys Ser Ser Asn Val Ser Val Ala His Asp Ala Ser Gly Lys
385                 390                 395                 400

Arg Val Tyr Tyr Leu Thr Arg Asp Pro Thr Thr Pro Leu Ala Arg Ala
                405                 410                 415

Ala Trp Glu Thr Ala Arg His Thr Pro Ile Asn Ser Trp Leu Gly Asn
            420                 425                 430

Ile Ile Met Tyr Ala Pro Thr Leu Trp Ala Arg Met Val Leu Met Thr
        435                 440                 445

His Phe Phe Ser Ile Leu Leu Ala Gln Glu Gln Leu Glu Lys Ala Leu
    450                 455                 460

Asp Cys Gln Ile Tyr Gly Ala Cys Tyr Ser Ile Glu Pro Leu Asp Leu
465                 470                 475                 480

Pro Gln Ile Ile Glu Arg Leu His Gly Leu Ser Ala Phe Ser Leu His
                485                 490                 495

Ser Tyr Ser Pro Gly Glu Ile Asn Arg Val Ala Ser Cys Leu Arg Lys
            500                 505                 510

Leu Gly Val Pro Pro Leu Arg Val Trp Arg His Arg Ala Arg Ser Val
        515                 520                 525

Arg Ala Lys Leu Leu Ser Gln Gly Gly Arg Ala Ala Thr Cys Gly Lys
    530                 535                 540

Tyr Leu Phe Asn Trp Ala Val Arg Thr Lys Leu Lys Leu Thr Pro Ile
545                 550                 555                 560
```

| | | | | | | | | | | | | |
|---|---|---|---|---|---|---|---|---|---|---|---|---|
|Pro|Ala|Ala|Ser|Arg|Leu|Asp|Leu|Ser|Gly|Trp|Phe|Val|Ala|Gly|Tyr|
| | | | |565| | | |570| | | |575| | | |
|Asn|Gly|Gly|Asp|Ile|Tyr|His|Ser|Leu|Ser|Arg|Ala|Arg|Pro|Arg|
| | | |580| | | |585| | | |590| | |

VIRAL POLYMERASE INHIBITORS

RELATED APPLICATIONS

This application claims benefit of U.S. Ser. No. 60/953,701, filed Aug. 3, 2007, which is herein incorporated by reference.

FIELD OF THE INVENTION

The present invention relates to compounds, compositions and methods for the treatment of hepatitis C virus (HCV) infection. In particular, the present invention provides novel inhibitors of the hepatitis C virus NS5B polymerase, pharmaceutical compositions containing such compounds and methods for using these compounds in the treatment of HCV infection.

BACKGROUND OF THE INVENTION

It is estimated that at least 130 million persons worldwide are infected with the hepatitis C virus (HCV). Acute HCV infection progresses to chronic infection in a high number of cases, and, in some infected individuals, chronic infection leads to serious liver diseases such as cirrhosis and hepatocellular carcinoma.

Currently, standard treatment of chronic hepatitis C infection involves administration of pegylated interferon-alpha in combination with ribavirin. However, this therapy is not effective in reducing HCV RNA to undetectable levels in many infected patients and is associated with often intolerable side effects such as fever and other influenza-like symptoms, depression, thrombocytopenia and hemolytic anemia. Furthermore, some HCV-infected patients have co-existing conditions which contraindicate this treatment.

Therefore, a need exists for alternative treatments for hepatitis C viral infection. One possible strategy to address this need is the development of effective antiviral agents which inactivate viral or host cell factors which are essential for viral replication.

HCV is an enveloped positive strand RNA virus in the genus Hepacivirus in the Flaviviridae family. The single strand HCV RNA genome is approximately 9500 nucleotides in length and has a single open reading frame (ORF), flanked by 5' and 3' non-translated regions. The HCV 5' non-translated region is 341 nucleotides in length and functions as an internal ribosome entry site for cap-independent translation initiation. The open reading frame encodes a single large polyprotein of about 3000 amino acids which is cleaved at multiple sites by cellular and viral proteases to produce the mature structural and non-structural (NS2, NS3, NS4A, NS4B, NS5A, and NS5B) proteins. The viral NS2l3 protease cleaves at the NS2-NS3 junction; while the viral NS3 protease mediates the cleavages downstream of NS3, at the NS3-NS4A, NS4A-NS4B, NS4B-NS5A and NS5A-NS5B cleavage sites. The NS3 protein also exhibits nucleoside triphosphatase and RNA helicase activities. The NS4A protein acts as a cofactor for the NS3 protease and may also assist in the membrane localization of NS3 and other viral replicase components. Although NS4B and the NS5A phosphoprotein are also likely components of the replicase, their specific roles are unknown. The NS5B protein is the elongation subunit of the HCV replicase possessing RNA-dependent RNA polymerase (RdRp) activity.

The development of new and specific anti-HCV treatments is a high priority, and virus-specific functions essential for replication are the most attractive targets for drug development. The absence of RNA dependent RNA polymerases in mammals, and the fact that this enzyme appears to be essential to viral replication, would suggest that the NS5B polymerase is an ideal target for anti-HCV therapeutics. It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046-2051).

WO 2007/087717 discloses compounds of the general formula (A):

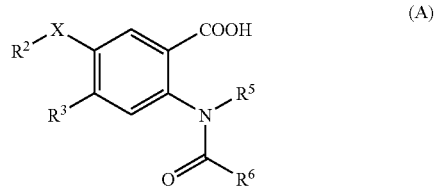

wherein $R^2$ is an optionally substituted aryl and $R^6$ is an optionally substituted $(C_{5-7})$cycloalkyl or aryl which are useful for the treatment of Hepatitis C virus infections.

SUMMARY OF THE INVENTION

The present invention provides a novel series of compounds having inhibitory activity against HCV polymerase. In particular compounds according to this invention inhibit RNA synthesis by the RNA dependent RNA polymerase of HCV, especially the enzyme NS5B encoded by HCV. A further advantage of compounds provided by this invention is their low to very low or even non-significant activity against other polymerases. Further objects of this invention arise for the one skilled in the art from the following description and the examples.

One aspect of the invention provides compounds of formula (I):

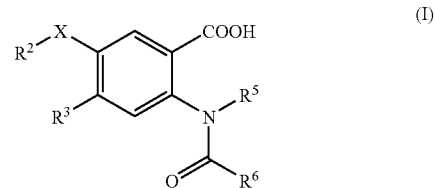

wherein:

X is selected from O and S;

$R^2$ is Het or aryl, optionally substituted with 1 to 5 $R^{20}$ substituents, wherein $R^{20}$ in each case is independently selected from:

a) halo, cyano or nitro;

b) $R^7$, —C(=O)—$R^7$, —C(=O)—O—$R^7$, —O—$R^7$, —S—$R^7$, —SO—$R^7$, —SO$_2$—$R^7$, —($C_{1-6}$)alkylene-$R^7$, —($C_{1-6}$)alkylene-C(=O)—$R^7$, —($C_{1-6}$)alkylene-C(=O)—O—$R^7$, —($C_{1-6}$)alkylene-O—$R^7$, ($C_{1-6}$)alkylene-S—$R^7$, —($C_{1-6}$)alkylene-SO—$R^7$ or —($C_{1-6}$)alkylene-SO$_2$—$R^7$;

wherein $R^7$ is in each instance independently selected from H, ($C_{1-6}$)alkyl, ($C_{2-6}$)alkenyl, ($C_{2-6}$)alkynyl, ($C_{1-6}$)haloalkyl, ($C_{3-7}$)cycloalkyl, aryl and Het;

wherein the ($C_{1-6}$)alkyl, ($C_{2-6}$)alkenyl, ($C_{2-6}$)alkynyl, ($C_{3-7}$)cycloalkyl and ($C_{1-6}$)alkylene are optionally substituted with 1 or 2 substituents each independently selected from —OH, —(C$_{1-6}$)alkyl, halo, —(C$_{1-6}$)haloalkyl, (C$_{3-7}$)cycloalkyl, —O—(C$_{1-6}$)alkyl, cyano, COOH, —NH$_2$, —NH(C$_{1-4}$)alkyl, —NH(C$_{3-7}$)cycloalkyl, —N((C$_{1-4}$)alkyl)(C$_{3-7}$)cycloalkyl and —N((C$_{1-4}$)alkyl)$_2$; and wherein each of the aryl and Het is optionally substituted with 1 to 3 substituents each independently selected from:
 i) halo, cyano, oxo, thioxo, imino, —OH, —O—(C$_{1-6}$)alkyl, —O—(C$_{1-6}$)haloalkyl, (C$_{3-7}$)cycloalkyl, (C$_{1-6}$)haloalkyl, —C(=O)—(C$_{1-6}$)alkyl, —SO$_2$(C$_{1-6}$)alkyl, —C(=O)—NH$_2$, —C(=O)—NH(C$_{1-4}$)alkyl, —C(=O)—N((C$_{1-4}$)alkyl)$_2$, —C(=O)—NH(C$_{3-7}$)cycloalkyl, —C(=O)—N((C$_{1-4}$)alkyl)(C$_{3-7}$)cycloalkyl, —NH$_2$, —NH(C$_{1-4}$)alkyl, —N((C$_{1-4}$)alkyl)$_2$, —NH(C$_{3-7}$)cycloalkyl, —N((C$_{1-4}$)alkyl)(C$_{3-7}$)cycloalkyl or —NH—C(=O)(C$_{1-4}$)alkyl;
 ii) (C$_{1-6}$)alkyl optionally substituted with —OH, —O—(C$_{1-6}$)haloalkyl, or —O—(C$_{1-6}$)alkyl; and
 iii) aryl or Het, wherein each of the aryl and Het is optionally substituted with halo or (C$_{1-6}$)alkyl; and
c) —N(R$^8$)R$^9$, —C(=O)—N(R$^8$)R$^9$, —O—C(=O)—N(R$^8$)R$^9$, SO$_2$—N(R$^8$)R$^9$, —(C$_{1-6}$)alkylene-N(R$^8$)R$^9$, —(C$_{1-6}$)alkylene-C(=O)—N(R$^8$)R$^9$, —(C$_{1-6}$)alkylene-O—C(=O)—N(R$^8$)R$^9$, or —(C$_{1-6}$)alkylene-SO$_2$—N(R$^8$)R$^9$;
 wherein the (C$_{1-6}$)alkylene is optionally substituted with 1 or 2 substituents each independently selected from —OH, —(C$_{1-6}$)alkyl, halo, —(C$_{1-6}$)haloalkyl, (C$_{3-7}$)cycloalkyl cyano, COOK, —NH$_2$, —NH(C$_{1-4}$)alkyl, —NH(C$_{3-7}$)cycloalkyl, —N((C$_{1-4}$)alkyl)(C$_{3-7}$)cycloalkyl and —N((C$_{1-4}$)alkyl)$_2$;
 R$^8$ is in each instance independently selected from H, (C$_{1-6}$)alkyl and (C$_{3-7}$)cycloalkyl; and
 R$^9$ is in each instance independently selected from R$^7$, —O— (C$_{1-6}$)alkyl, —(C$_{1-6}$)alkylene-R$^7$, —SO$_2$—R$^7$, —C(=O)—R$^7$, —C(=O)OR$^7$ and —C(=O)N(R$^8$)R$^7$; wherein R$^7$ and R$^8$ are as defined above;
  or R$^8$ and R$^9$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;
  wherein the heterocycle is optionally substituted with 1 to 3 substituents each independently selected from (C$_{1-6}$)alkyl, (C$_{1-6}$)haloalkyl, halo, oxo, OH, SH, (C$_{3-7}$)cycloalkyl, —NH$_2$, —NH(C$_{1-6}$)alkyl, —N((C$_{1-6}$)alkyl)$_2$, —NH(C$_{3-7}$)cycloalkyl, —N((C$_{1-4}$)alkyl)(C$_{3-7}$)cycloalkyl, —C(=O)(C$_{1-6}$)alkyl and —NHC(=O)—(C$_{1-6}$)alkyl;
R$^3$ is selected from H, halo, CN, (C$_{1-4}$)alkyl, —OH, —O—(C$_{1-4}$)alkyl, —S—(C$_{1-4}$)alkyl, —NH$_2$, —NH(C$_{1-4}$)alkyl, —NH(C$_{3-7}$)cycloalkyl, —((C$_{1-4}$)alkyl)(C$_{3-7}$)cycloalkyl and —N((C$_{1-4}$)alkyl)$_2$;
R$^5$ is H, (C$_{1-6}$)alkyl, (C$_{3-7}$)cycloalkyl, (C$_{3-7}$)cycloalkyl-(C$_{1-6}$)alkyl- or Het; the (C$_{1-6}$)alkyl and Het each being optionally substituted with 1 to 4 substituents each independently selected from (C$_{1-6}$)alkyl, (C$_{1-6}$)haloalkyl, (C$_{3-7}$)cycloalkyl, Het, —OH, —COOH, —C(=O)—(C$_{1-6}$)alkyl, —C(=O)—O—(C$_{1-6}$)alkyl, —SO$_2$(C$_{1-6}$)alkyl and —C(=O)—N(R$^{51}$)R$^{52}$;
 wherein R$^{51}$ is H, (C$_{1-6}$)alkyl or (C$_{3-7}$)cycloalkyl; and
 R$^{52}$ is H, (C$_{1-6}$)alkyl, (C$_{3-7}$)cycloalkyl, aryl, Het, aryl-(C$_{1-3}$)alkyl- or Het-(C$_{1-3}$)alkyl-;

wherein each of the (C$_{1-6}$)alkyl, (C$_{3-7}$)cycloalkyl, aryl, Het, aryl-(C$_{1-3}$)alkyl- and Het-(C$_{1-3}$)alkyl- are optionally substituted with 1 to 3 substituents each independently selected from (C$_{1-6}$)alkyl, (C$_{1-6}$)haloalkyl, halo, oxo, —OH, —O(C$_{1-6}$)alkyl, —NH$_2$, —NH(C$_{1-6}$)alkyl, —N((C$_{1-6}$)alkyl)$_2$, —NH(C$_{3-7}$)cycloalkyl, —N((C$_{1-4}$)alkyl)(C$_{3-7}$)cycloalkyl, —C(=O)(C$_{1-6}$)alkyl and —NHC(=O)—(C$_{1-6}$)alkyl;
 wherein the (C$_{1-6}$)alkyl is optionally substituted with OH;
or R$^{51}$ and R$^{52}$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;
 wherein the heterocycle is optionally substituted with 1 to 3 substituents each independently selected from (C$_{1-6}$)alkyl, (C$_{1-6}$)haloalkyl, halo, oxo, —OH, —O(C$_{1-6}$)alkyl, —NH$_2$, —NH(C$_{1-4}$)alkyl, —N((C$_{1-6}$)alkyl)$_2$, —NH(C$_{3-7}$)cycloalkyl, —N((C$_{1-4}$)alkyl)(C$_{3-7}$)cycloalkyl, —C(=O)(C$_{1-6}$)alkyl and —NHC(=O)—(C$_{1-4}$)alkyl;
 wherein the (C$_{1-6}$)alkyl is optionally substituted with OH;
R$^6$ is Het; being optionally substituted with 1 to 5 substituents each independently selected from halo, (C$_{1-6}$)alkyl, (C$_{1-6}$)haloalkyl, (C$_{3-7}$)cycloalkyl, —OH, —SH, —O—(C$_{1-4}$)alkyl, —S—(C$_{1-4}$)alkyl and —N(R$^8$)R$^9$; wherein R$^6$ and R$^9$ are as defined above; and
Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;
or a salt or ester thereof;
with the proviso that when X is O, R$^2$ is phenyl, R$^3$ is H and R$^5$ is H, then R$^6$ is not

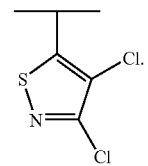

Another aspect of this invention provides a compound of formula (I), or a pharmaceutically acceptable salt or ester thereof, as a medicament.

Still another aspect of this invention provides a pharmaceutical composition comprising a therapeutically effective amount of a compound of formula (I) or a pharmaceutically acceptable salt or ester thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described hereinabove for the treatment of a hepatitis C viral infection in a mammal having or at risk of having the infection.

A further aspect of the invention involves a method of treating a hepatitis C viral infection in a mammal having or at risk of having the infection, the method comprising administering to the mammal a therapeutically effective amount of a compound of formula (I), a pharmaceutically acceptable salt or ester thereof, or a composition thereof as described hereinabove.

Another aspect of the invention involves a method of treating a hepatitis C viral infection in a mammal having or at risk of having the infection, the method comprising administering to the mammal a therapeutically effective amount of a combination of a compound of formula (I) or a pharmaceutically acceptable salt or ester thereof, and at least one other antiviral agent; or a composition thereof.

Also within the scope of this invention is the use of a compound of formula (I) as described herein, or a pharmaceutically acceptable salt or ester thereof, for the treatment of a hepatitis C viral infection in a mammal having or at risk of having the infection.

Another aspect of this invention provides the use of a compound of formula (I) as described herein, or a pharmaceutically acceptable salt or ester thereof, for the manufacture of a medicament for the treatment of a hepatitis C viral infection in a mammal having or at risk of having the infection.

An additional aspect of this invention refers to an article of manufacture comprising a composition effective to treat a hepatitis C viral infection; and packaging material comprising a label which indicates that the composition can be used to treat infection by the hepatitis C virus; wherein the composition comprises a compound of formula (I) according to this invention or a pharmaceutically acceptable salt or ester thereof.

Still another aspect of this invention relates to a method of inhibiting the replication of hepatitis C virus comprising exposing the virus to an effective amount of the compound of formula (I), or a salt or ester thereof, under conditions where replication of hepatitis C virus is inhibited.

Further included in the scope of the invention is the use of a compound of formula (I), or a salt or ester thereof, to inhibit the replication of hepatitis C virus.

DETAILED DESCRIPTION OF THE INVENTION

Definitions

As used herein, the following definitions apply unless otherwise noted:

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

The term "$(C_{1-n})$alkyl" as used herein, wherein n is an integer, either alone or in combination with another radical, is intended to mean acyclic, straight or branched chain alkyl radicals containing from 1 to n carbon atoms. "$(C_{1-6})$alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tert-butyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "$(C_{1-n})$alkylene" as used herein, wherein n is an integer, either alone or in combination with another radical, is intended to mean acyclic, straight or branched chain divalent alkyl radicals containing from 1 to n carbon atoms. "$(C_{1-6})$alkylene" includes, but is not limited to,

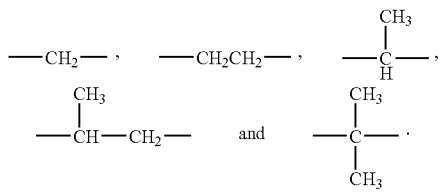

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$ alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{3-m})$cycloalkyl" as used herein, wherein m is an integer, either alone or in combination with another radical, is intended to mean a cycloalkyl substituent containing from 3 to m carbon atoms and includes, but is not limited to, cyclopropyl, cyclobutyl, cyclopentyl, cyclohexyl and cycloheptyl. When a $(C_{3-m})$cycloalkyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{3-m})$cycloalkyl-$(C_{1-n})$alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above. Examples of $(C_{3-7})$ cycloalkyl-$(C_{1-6})$alkyl- include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl- group is substituted, it is understood that substituents may be attached to either the cycloalkyl or the alkyl portion thereof or both, unless specified otherwise.

The term "aryl" as used herein, either alone or in combination with another radical, is intended to mean a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, 1-naphthyl, 2-naphthyl, tetrahydronaphthyl and dihydronaphthyl. When an aryl group is substituted, it is understood that substituents may be attached to any carbon atom thereof which would otherwise bear a hydrogen atom, unless specified otherwise.

The term "aryl-$(C_{1-n})$alkyl-" as used herein, wherein n is an integer, either alone or in combination with another radical, is intended to mean an alkyl radical having 1 to n carbon atoms as defined above which is itself substituted with an aryl radical as defined above. Examples of aryl-$(C_{1-n})$alkyl- include, but are not limited to, phenylmethyl (benzyl), 1-phenylethyl, 2-phenylethyl and phenylpropyl. When an aryl-$(C_{1-n})$alkyl- group is substituted, it is understood that substituents may be attached to either the aryl or the alkyl portion thereof or both, unless specified otherwise.

The term "Het" as used herein, either alone or in combination with another radical, is intended to mean a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$, unless specified otherwise. When a Het group is substituted, it is understood that substituents may be attached to any carbon atom or heteroatom thereof which would otherwise bear a hydrogen atom, unless specified otherwise.

The term "Het-$(C_{1-n})$alkyl-" as used herein and unless specified otherwise, wherein n is an integer, either alone or in combination with another radical, is intended to mean an alkyl radical having 1 to n carbon atoms as defined above which is itself substituted with a Het substituent as defined above. Examples of Het-$(C_{1-n})$alkyl-include, but are not limited to, thienylmethyl, furylmethyl, piperidinylethyl, 2-pyridinylmethyl, 3-pyridinylmethyl, 4-pyridinylmethyl, quinolinylpropyl, and the like. When a Het-$(C_{1-n})$alkyl- group is substituted, it is understood that substituents may be attached to either the Het or the alkyl portion thereof or both, unless specified otherwise.

The term "heteroatom" as used herein is intended to mean O, S or N.

The term "heterocycle" as used herein and unless specified otherwise, either alone or in combination with another radical, is intended to mean a 4- to 7-membered saturated, unsaturated or aromatic heterocycle containing from 1 to 4 heteroatoms each independently selected from O, N and S; or a monovalent radical derived by removal of a hydrogen atom therefrom. Examples of such heterocycles include, but are not limited to, azetidine, pyrrolidine, tetrahydrofuran, tetrahydrothiophene, thiazolidine, oxazolidine, pyrrole, thiophene, furan, pyrazole, imidazole, isoxazole, oxazole, isothiazole, thiazole, triazole, tetrazole, piperidine, piperazine, azepine, diazepine, pyran, 1,4-dioxane, 4-morpholine, 4-thiomorpholine, pyridine, pyridine-N-oxide, pyridazine, pyrazine, pyrimidine, and the following heterocycles:

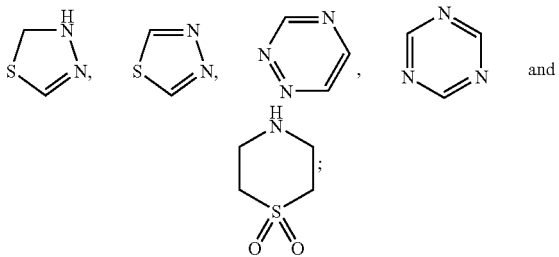

and saturated, unsaturated and aromatic derivatives thereof.

The term "heteropolycycle" as used herein and unless specified otherwise, either alone or in combination with another radical, is intended to mean a heterocycle as defined above fused to one or more other cycle, including a carbocycle, a heterocycle or any other cycle; or a monovalent radical derived by removal of a hydrogen atom therefrom. Examples of such heteropolycycles include, but are not limited to, indole, isoindole, benzimidazole, benzothiophene, benzofuran, benzodioxole, benzothiazole, quinoline, isoquinoline, naphthyridine, and the following heteropolycycles:

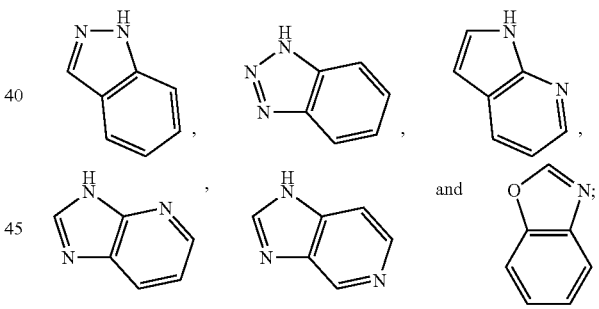

and saturated, unsaturated and aromatic derivatives thereof.

The term "halo" as used herein is intended to mean a halogen substituent selected from fluoro, chloro, bromo or iodo.

The term "$(C_{1-n})$haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of $(C_{1-n})$haloalkyl include but are not limited to chloromethyl, chloroethyl, dichloroethyl, bromomethyl, bromoethyl, dibromoethyl, fluoromethyl, difluoromethyl, trifluoromethyl, fluoroethyl and difluoroethyl.

The terms "—O—$(C_{1-n})$alkyl" or "$(C_{1-n})$alkoxy" as used herein interchangeably, wherein n is an integer, either alone or in combination with another radical, is intended to mean an oxygen atom further bonded to an alkyl radical having 1 to n carbon atoms as defined above. Examples of —O—$(C_{1-n})$ alkyl include but are not limited to methoxy (CH$_3$O—), ethoxy (CH$_3$CH$_2$O—), propoxy (CH$_3$CH$_2$CH$_2$O—), 1-methylethoxy (iso-propoxy; (CH$_3$)$_2$CH—O—) and 1,1-dimethylethoxy (tert-butoxy; (CH$_3$)$_3$C—O—). When an —O—(C$_{1-n}$)alkyl radical is substituted, it is understood to be substituted on the (C$_{1-n}$)alkyl portion thereof.

The terms "—S—(C$_{1-n}$)alkyl" or "(C$_{1-n}$)alkylthio" as used herein interchangeably, wherein n is an integer, either alone or in combination with another radical, is intended to mean an sulfur atom further bonded to an alkyl radical having 1 to n carbon atoms as defined above. Examples of —S—(C$_{1-n}$)alkyl include but are not limited to methylthio (CH$_3$S—), ethylthio (CH$_3$CH$_2$S—), propylthio (CH$_3$CH$_2$CH$_2$S—), 1-methylethylthio (isopropylthio; (CH$_3$)$_2$CH—S—) and 1,1-dimethylethylthio (tert-butylthio; (CH$_3$)$_3$C—S—). When —S—(C$_{1-n}$)alkyl radical, or an oxidized derivative thereof, such as an —SO—(C$_{1-n}$)alkyl radical or an —SO$_2$—(C$_{1-n}$)alkyl radical, is substituted, each is understood to be substituted on the (C$_{1-n}$)alkyl portion thereof.

The term "oxo" as used herein is intended to mean an oxygen atom attached to a carbon atom as a substituent by a double bond (═O).

The term "thioxo" as used herein is intended to mean a sulfur atom attached to a carbon atom as a substituent by a double bond (═S).

The term "imino" as used herein is intended to mean a NH group attached to a carbon atom as a substituent by a double bond (═NH).

The term "cyano" or "CN" as used herein is intended to mean a nitrogen atom attached to a carbon atom by a triple bond (C≡N).

The term "COOH" as used herein is intended to mean a carboxyl group (—C(═O)—OH). It is well known to one skilled in the art that carboxyl groups may be substituted by functional group equivalents. Examples of such functional group equivalents contemplated in this invention include, but are not limited to, esters, amides, imides, boronic acids, phosphonic acids, phosphoric acids, tetrazoles, triazoles, N-acylsulfamides (RCONHSO$_2$NR$_2$), and N-acylsulfonamides (RCONHSO$_2$R).

The term "functional group equivalent" as used herein is intended to mean an atom or group that may replace another atom or group which has similar electronic, hybridization or bonding properties.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof, herein incorporated by reference.

The following designation "" is used in sub-formulas to indicate the bond which is connected to the rest of the molecule as defined.

The term "salt thereof" as used herein is intended to mean any acid and/or base addition salt of a compound according to the invention, including but not limited to a pharmaceutically acceptable salt thereof.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Berge et al., J. Pharm. Sci., 1977, 66, pp. 1-19, herein incorporated by reference.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The term "ester thereof" as used herein is intended to mean any ester of a compound according to the invention in which any of the —COOH substituents of the molecule is replaced by a —COOR substituent, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl, each of which being optionally further substituted.

The term "ester thereof" includes but is not limited to pharmaceutically acceptable esters thereof.

The term "pharmaceutically acceptable ester" as used herein is intended to mean esters of the compound according to the invention in which any of the COOH substituents of the molecule are replaced by a —COOR substituent, in which the R moiety of the ester is selected from alkyl (including, but not limited to, methyl, ethyl, propyl, 1-methylethyl, 1,1-dimethylethyl, butyl); alkoxyalkyl (including, but not limited to methoxymethyl); acyloxyalkyl (including, but not limited to acetoxymethyl); arylalkyl (including, but not limited to, benzyl); aryloxyalkyl (including, but not limited to, phenoxymethyl); and aryl (including, but not limited to phenyl) optionally substituted with halogen, $(C_{1-4})$alkyl or $(C_{1-4})$alkoxy. Other suitable esters can be found in Design of Prodrugs, Bundgaard, H. Ed. Elsevier (1985), herein incorporated by reference. Such pharmaceutically acceptable esters are usually hydrolyzed in vivo when injected into a mammal and transformed into the acid form of the compound according to the invention. With regard to the esters described above, unless otherwise specified, any alkyl moiety present preferably contains 1 to 16 carbon atoms, more preferably 1 to 6 carbon atoms. Any aryl moiety present in such esters preferably comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "mammal" as used herein is intended to encompass humans, as well as non-human mammals which are susceptible to infection by hepatitis C virus. Non-human mammals include but are not limited to domestic animals, such as cows, pigs, horses, dogs, cats, rabbits, rats and mice, and non-domestic animals.

The term "treatment" as used herein is intended to mean the administration of a compound or composition according to the present invention to alleviate or eliminate symptoms of the hepatitis C disease and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood.

The term "antiviral agent" as used herein is intended to mean an agent that is effective to inhibit the formation and/or replication of a virus in a mammal, including but not limited to agents that interfere with either host or viral mechanisms necessary for the formation and/or replication of a virus in a mammal.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

PREFERRED EMBODIMENTS

In the following preferred embodiments, groups and substituents of the compounds according to this invention are described in detail.

X:
X-A: In one embodiment, X is O.
X-B: in another embodiment, X is S.
Any and each individual definition of X as set out herein may be combined with any and each individual definition of $R^2$, $R^{20}$, $R^3$, $R^5$ and $R^6$ as set out herein.

$R^2$:
$R^2$-A: In one embodiment, $R^2$ is Het or aryl, optionally substituted with 1 to 5 $R^{20}$ substituents, wherein $R^{20}$ is as defined herein.

$R^2$-B: In another embodiment, $R^2$ is Het wherein Het is a 5- or 6-membered heterocycle containing 1 to 3 heteroatoms each independently selected from O, N and S, or a 9- or 10-membered bicyclic heteropolycycle containing 1 to 3 heteroatoms each independently selected from O, N and S; wherein Het is optionally substituted with 1 to 5 $R^{20}$ substituents, wherein $R^{20}$ is as defined herein.

$R^2$-C: In another embodiment, $R^2$ is Het wherein Het is a 5- or 6-membered aromatic heterocycle containing 1 or 2 N heteroatoms, or a 9- or 10-membered bicyclic heteropolycycle containing 1 or 2 N heteroatoms; wherein Het is optionally substituted with 1 to 3 $R^{20}$ substituents, wherein $R^{20}$ is as defined herein.

$R^2$-D: In another embodiment, $R^2$ is Het selected from the following formulas:

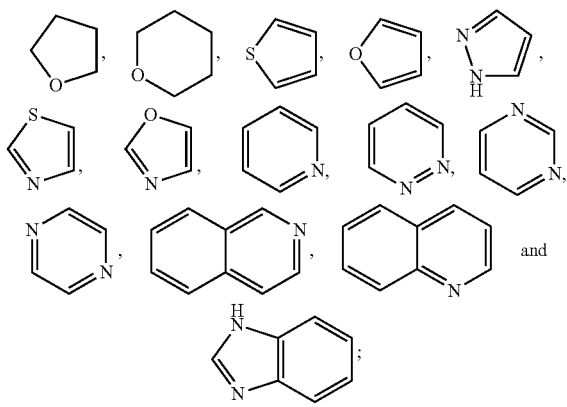

wherein Het is optionally substituted with 1 to 3 $R^{20}$ substituents, wherein $R^{20}$ is as defined herein.

$R^2$-E: In another embodiment, $R^2$ is Het of the formula:

wherein Het is optionally substituted with 1 to 3 $R^{20}$ substituents, wherein $R^{20}$ is as defined herein.

R²-F: In another embodiment, R² is of the formula:

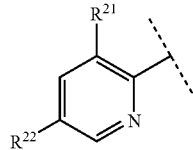

wherein R²¹ is as defined:
R²¹-A: In this embodiment, R²¹ is selected from H, halo, $(C_{1-6})$alkyl, $(C_{1-6})$haloalkyl, $(C_{3-7})$cycloalkyl and —O—$(C_{1-6})$haloalkyl.
R²¹-B: In this embodiment, R²¹ is selected from H, Cl, Br, $CH_3$, $CHF_2$, $CF_3$, cyclopropyl, cyclobutyl and —$OCF_3$.
R²¹-C: In this embodiment, R²¹ is H, $CHF_2$ or $CF_3$.
R²¹-D: In this embodiment, R²¹ is H or $CF_3$.
R²¹-E: In this embodiment, R²¹ is $CHF_2$ or $CF_3$.
R²¹-F: In this embodiment, R²¹ is $CF_3$;
and R²² is R²⁰ wherein R²⁰ is as defined herein.
Any and each individual definition of R²¹ as set out herein may be combined with any and each individual definition of X, R²⁰, R³, R⁵ and R⁶ as set out herein.

R²-G: In another embodiment, R² is a group of the formula:

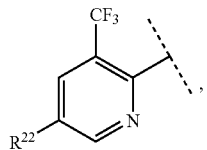

wherein R²² is R²⁰ wherein R²⁰ is as defined herein.
R²-H: In another embodiment, R² is naphthyl or phenyl, the phenyl being optionally substituted with 1 to 5 R²⁰ wherein R²⁰ is as defined herein.
R²-I: In yet another embodiment, R² is phenyl optionally substituted with 1 to 3 R²⁰ wherein R²⁰ is as defined herein.
R²-J: In an alternative embodiment, R² is a group of formula:

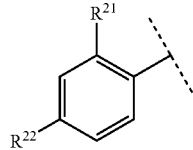

wherein R²¹ and R²² are as defined herein.
R²-K: In another embodiment, R² is a group of the formula:

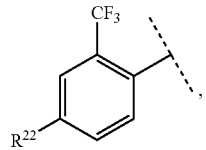

wherein R²² is R²⁰ wherein R²⁰ is as defined herein.
R²-L: In yet another alternative embodiment, R² is selected from the group:

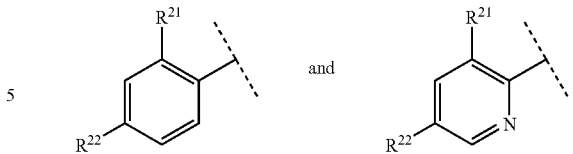

wherein R²¹ and R²² are as defined herein.
R²-M: In yet another alternative embodiment, R² is selected from the group:

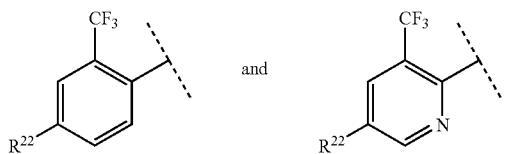

wherein R²² is as defined herein.
Any and each individual definition of R² as set out herein may be combined with any and each individual definition of X, R²⁰, R³, R⁵ and R⁶ as set out herein.

R²⁰-A:
R²⁰-A: In one embodiment, R²⁵ is selected from:
a) halo, cyano or nitro;
b) R⁷, —C(=O)—R⁷, —C(=O)—O—R⁷, —O—R⁷, —S—R⁷, —SO—R⁷, —$SO_2$—R⁷, —$(C_{1-6})$alkylene-R⁷, —$(C_{1-6})$alkylene-C(=O)—R⁷, —$(C_{1-6})$alkylene-C(=O)—O—R⁷, —$(C_{1-6})$alkylene-O—R⁷, $(C_{1-6})$alkylene-S—R⁷, —$(C_{1-6})$alkylene-SO—R⁷ or —$(C_{1-6})$alkylene-$SO_2$—R⁷;
wherein R⁷ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het;
wherein the $(C_{1-6})$alkyl, $(C_{2-6})$alkenyl, $(C_{2-6})$alkynyl, $(C_{3-7})$cycloalkyl and $(C_{1-6})$alkylene are optionally substituted with 1 or 2 substituents each independently selected from —OH, —$(C_{1-6})$alkyl, halo, —$(C_{1-6})$haloalkyl, $(C_{3-7})$cycloalkyl, —O—$(C_{1-6})$alkyl, cyano, COOH, —$NH_2$, —NH$(C_{1-4})$alkyl, —NH$(C_{3-7})$cycloalkyl, —N(($C_{1-4}$)alkyl)($C_{3-7}$)cycloalkyl and —N(($C_{1-4}$)alkyl)$_2$; and
wherein each of the aryl and Het is optionally substituted with 1 to 3 substituents each independently selected from:
i) halo, cyano, oxo, thioxo, imino, —OH, —O—$(C_{1-6})$alkyl, —O—$(C_{1-6})$haloalkyl, $(C_{3-7})$cycloalkyl, —C(=O)—$(C_{1-6})$alkyl, —$SO_2(C_{1-6})$alkyl, —C(=O)—$NH_2$, —C(=O)—NH$(C_{1-4})$alkyl, —C(=O)—N(($C_{1-4}$)alkyl)$_2$, —C(=O)—NH($C_{3j}$)cycloalkyl, —C(=O)—N(($C_{1-4}$)alkyl)($C_{3-7}$)cycloalkyl, —$NH_2$, —NH$(C_{1-4})$alkyl, —N(($C_{1-4}$)alkyl)$_2$, —NH$(C_{3-7})$cycloalkyl, —N(($C_{1-4}$)alkyl)($C_{3-7}$)cycloalkyl or —NH—C(=O)$(C_{1-4})$alkyl;
ii) $(C_{1-6})$alkyl optionally substituted with —OH, —O—$(C_{1-6})$haloalkyl, or —O—$(C_{1-6})$alkyl; and
iii) aryl or Het, wherein each of the aryl and Het is optionally substituted with halo or $(C_{1-6})$alkyl; and
c) —N(R⁸)R⁹, —C(=O)—N(R⁸)R⁹, —O—C(=O)—N(R⁸)R⁹, —$SO_2$—N(R⁸)R⁹, —$(C_{1-6})$alkylene-N(R⁸)R⁹, —$(C_{1-6})$alkylene-C(=O)—N(R⁸)R⁹, —$(C_{1-6})$alkylene-O—C(=O)—N(R⁸)R⁹, or —$(C_{1-6})$alkylene-$SO_2$—N(R⁸)R⁹;

wherein the $(C_{1-6})$alkylene is optionally substituted with 1 or 2 substituents each independently selected from —OH, —$(C_{1-6})$alkyl, halo, —$(C_{1-6})$haloalkyl, $(C_{3-7})$cycloalkyl, —O—$(C_{1-6})$alkyl, cyano, COOH, —$NH_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$;

$R^8$ is in each instance independently selected from H, $(C_{1-6})$alkyl and $(C_{3-7})$cycloalkyl; and $R^9$ is in each instance independently selected from $R^7$, —O—$(C_{1-6})$alkyl, —$(C_{1-6})$alkylene-$R^7$, —$SO_2$—$R^7$, —C(=O)—$R^7$, —C(=O)O$R^7$ and —C(=O)N$(R^8)R^7$; wherein $R^7$ and $R^8$ are as defined above;

or $R^8$ and $R^9$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or $SO_2$;

wherein the heterocycle is optionally substituted with 1 to 3 substituents each independently selected from $(C_{1-6})$alkyl, $(C_{1-6})$haloalkyl, halo, oxo, —OH, SH, —S$(C_{1-6})$alkyl, $(C_{3-7})$cycloalkyl, —$NH_2$, —NH$(C_{1-6})$alkyl, —N$((C_{1-6})$alkyl$)_2$, —NH$(C_{3-7})$cycloalkyl, —N$((C_{1-4})$alkyl$)(C_{3-7})$cycloalkyl, —C(=O)$(C_{1-6})$alkyl and —NHC(=O)—$(C_{1-6})$alkyl.

$R^{20}$-B: In another embodiment, $R^{20}$ is selected from:
a) halo, cyano or nitro;
b) $R^7$, —$(C_{1-6})$alkylene-$R^7$, —C(=O)—$R^7$, —O—$R^7$, —C(=O)—O—$R^7$, —$(C_{1-6})$alkylene-O—$R^7$, —S—$R^7$, —$SO_2$—$R^7$, —$(C_{1-6})$alkylene-S—$R^7$ or —$(C_{1-6})$alkylene-$SO_2$—$R^7$;

wherein $R^7$ is in each instance independently selected from H, $(C_{1-6})$alkyl, $(C_{2-6})$alkenyl, $(C_{1-6})$haloalkyl, $(C_{3-7})$cycloalkyl, aryl and Het; wherein the Het is a 5- or 6-membered heterocycle containing 1 to 4 heteroatoms, each independently selected from N, O and S, or Het is a 9- or 10-membered heteropolycycle containing 1 to 4 heteroatoms, each independently selected from N, O and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$; and wherein the $(C_{1-6})$alkyl is optionally substituted with 1 or 2 substituents each independently selected from —OH, —O—$(C_{1-6})$alkyl and COOH; and wherein each of the aryl and Het is optionally substituted with 1 to 3 substituents each independently selected from halo, cyano, oxo, imino, —OH, —O—$(C_{1-6})$alkyl, —$NH_2$, —NH$(C_{1-4})$alkyl, —N$((C_{1-4})$alkyl$)_2$, —NH—C(=O)$(C_{1-4})$alkyl, $(C_{1-6})$alkyl and Het, wherein the Het is a 5- or 6-membered heterocycle containing 1 to 4 heteroatoms, each independently selected from N, O and S; and c) —N$(R^8)R^9$, —$(C_{1-6})$alkylene-N$(R^8)R^9$ or —$(C_{1-6})$alkylene-C(=O)—N$(R^8)R^9$
wherein
$R^8$ is in each instance independently selected from H and $(C_{1-6})$alkyl; and $R^9$ is in each instance independently selected from $R^7$, —O—$(C_{1-6})$alkyl, —$SO_2$—$R^7$, —C(=O)—$R^7$, —C(=O)O$R^7$ and —C(=O)N$(R^8)R^7$; wherein $R^7$ and $R^8$ are as defined above.

$R^{20}$-C: In another embodiment, $R^{20}$ is selected from:
b) $R^7$, —$(C_{1-6})$alkylene-$R^7$, —C(=O)—$R^7$, —$(C_{1-6})$alkylene-O—$R^7$, —$SO_2$—$R^7$, —$(C_{1-6})$alkylene-S—$R^7$ or —$(C_{1-6})$alkylene-$SO_2$—$R^7$;

wherein $R^7$ is in each instance independently selected from H, $(C_{1-6})$alkyl, $(C_{2-6})$alkenyl, $(C_{1-6})$haloalkyl, $(C_{3-7})$cycloalkyl, aryl and Het;

wherein the Het is a 5- or 6-membered heterocycle containing 1 to 4 heteroatoms, each independently selected from N, O and S, or Het is a 9- or 10-membered heteropolycycle containing 1 to 4 heteroatoms, each independently selected from N, O and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$; and wherein the $(C_{1-6})$alkyl is optionally substituted with 1 or 2 substituents each independently selected from —OH, —O—$(C_{1-6})$alkyl and COOH; and wherein each of the aryl and Het is optionally substituted with 1 to 3 substituents each independently selected from halo, cyano, oxo, imino, —OH, —O—$(C_{1-6})$alkyl, —$NH_2$, —NH$(C_{1-4})$alkyl, —N$((C_{1-4})$alkyl$)_2$, —NH—C(=O)$(C_{1-4})$alkyl, $(C_{1-6})$alkyl and Het, wherein the Het is a 5- or 6-membered heterocycle containing 1 to 4 heteroatoms, each independently selected from N, O and S; and c) —$(C_{1-6})$alkylene-N$(R^8)R^9$ or —$(C_{1-6})$alkylene-C(=O)—N$(R^8)R^9$ wherein
$R^8$ is in each instance independently selected from H and $(C_{1-6})$alkyl; and
$R^9$ is in each instance independently selected from $R^7$, —O—$(C_{1-6})$alkyl, —$SO_2$—$R^7$, —C(=O)—$R^7$, —C(=O)O$R^7$ and —C(=O)N$(R^8)R^7$; wherein $R^7$ and $R^8$ are as defined above.

$R^{20}$-D: In another embodiment, $R^{20}$ is selected from:
a) halo or cyano;
b) $R^7$, —$CH_2$—$R^7$, —C(=O)—$R^7$, —$CH_2$—O—$R^7$, —$SO_2$—$R^7$, —$CH_2$—S—$R^7$ or —$CH_2$—$SO_2$—$R^7$;
wherein $R^7$ is in each instance independently selected from H, $(C_{1-6})$alkyl, $(C_{2-6})$alkenyl, $(C_{1-6})$haloalkyl, $(C_{3-7})$cycloalkyl, phenyl and Het; wherein the Het is selected from:

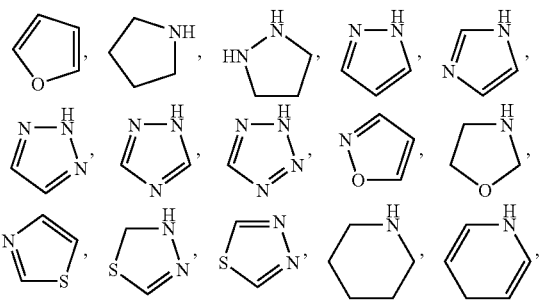

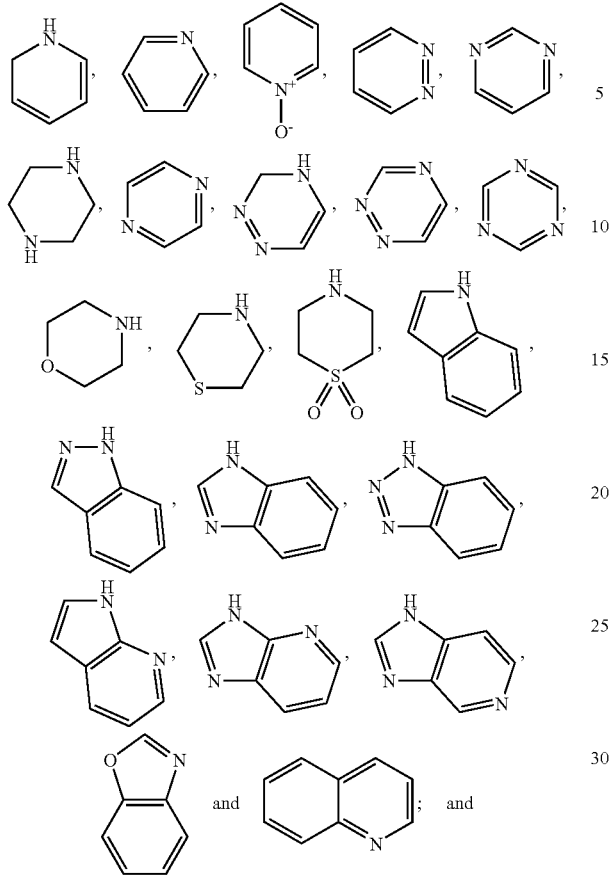

wherein the $(C_{1-6})$alkyl is optionally substituted with 1 or 2 substituents each independently selected from —OH, —O—$(C_{1-6})$alkyl and COOH; and wherein each of the phenyl and Het is optionally substituted with 1 to 3 substituents each independently selected from halo, cyano, oxo, imino, —OH, —O—$(C_{1-6})$alkyl, —$NH_2$, —NH$(C_{1-4})$alkyl, —N$((C_{1-4})$alkyl$)_2$, —NH—C(=O)$(C_{1-4})$alkyl and $(C_{1-6})$alkyl; and c) —$CH_2$—N($R^8$)$R^9$ or —$CH_2$—C(=O)—N($R^8$)$R^9$ wherein $R^8$ is in each instance independently selected from H and $(C_{1-6})$alkyl; and $R^9$ is in each instance independently selected from $R^7$, —O— $(C_{1-6})$alkyl, —$SO_2$—$R^7$, —C(=O)—$R^7$, —C(=O)O$R^7$ and —C(=O)N($R^8$)$R^7$; wherein $R^7$ and $R^8$ are as defined above.

$R^{20}$-E: In another embodiment, $R^{20}$ is selected from:
b) —$(C_{1-3})$alkylene-$R^7$, —$(C_{1-3})$alkylene-O—$R^7$, —$(C_{1-3})$alkylene-S—$R^7$ or —$(C_{1-3})$alkylene-$SO_2$—$R^7$;
wherein $R^7$ is Het; wherein the Het is a 5- or 6-membered heterocycle containing 1 to 4 heteroatoms, each independently selected from N, O and S, or Het is a 9- or 10-membered heteropolycycle containing 1 to 4 heteroatoms, each independently selected from N, O and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$;

wherein the Het is optionally substituted with 1 to 3 substituents each independently selected from halo, cyano, oxo, imino, —OH, —O—$(C_{1-6})$alkyl, —O—$(C_{1-6})$haloalkyl, $(C_{3-7})$cycloalkyl, —$NH_2$, —NH$(C_{1-4})$alkyl, —NH$(C_{3-7})$cycloalkyl, —N$((C_{1-4})$alkyl)$(C_{3-7})$cycloalkyl, —N$((C_{1-4})$alkyl$)_2$, —NH—C(=O)$(C_{1-4})$alkyl, $(C_{1-6})$alkyl and Het, wherein the Het is a 5- or 6-membered heterocycle containing 1 to 4 heteroatoms, each independently selected from N, O and S; and c) —$(C_{1-3})$alkylene-N($R^8$)$R^9$ wherein
$R^8$ is in each instance independently selected from H, $(C_{1-6})$alkyl and $(C_{3-7})$cycloalkyl; and
$R^9$ is $R^7$ wherein $R^7$ is as defined above.

$R^{20}$-F: In another embodiment, $R^{20}$ is selected from:
b) —$CH_2$—$R^7$, —$CH_2CH_2$—$R^7$, —$CH_2$—O—$R^7$, —$CH_2$—S—$R^7$ or $CH_2$—$SO_2$—$R^7$;
wherein $R^7$ is Het; wherein the Het is selected from:

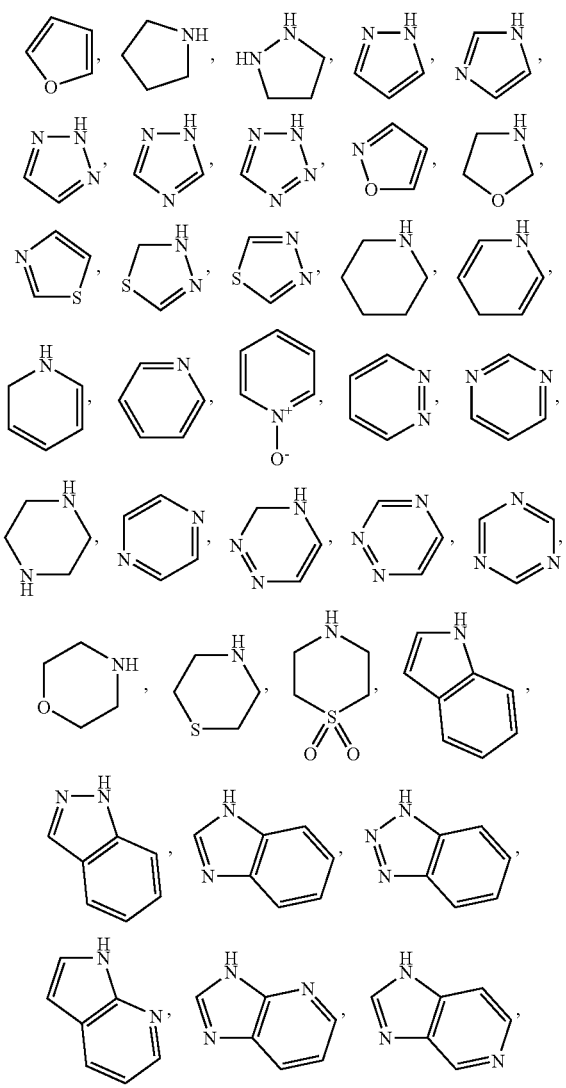

-continued

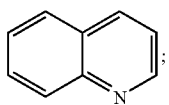

wherein the Het is optionally substituted with 1 to 3 substituents each independently selected from halo, cyano, oxo, imino, —OH, —O—$(C_{1-6})$alkyl, —$NH_2$, —NH$(C_{1-4})$alkyl, —N$((C_{1-4})$alkyl$)_2$, —NH—C(=O)$(C_{1-4})$alkyl and $(C_{1-6})$alkyl; and c) —$CH_2$—N$(R^8)R^9$ wherein $R^8$ is in each instance independently selected from H and $(C_{1-6})$alkyl; and $R^9$ is $R^7$ wherein $R^7$ is as defined above.

$R^{20}$-G: In another embodiment, $R^{20}$ is selected from:

b) $R^7$, —$(C_{1-6})$alkylene-$R^7$, —C(=O)—$R^7$, —$(C_{1-6})$alkylene-O—$R^7$, —$SO_2$—$R^7$, —$(C_{1-6})$alkylene-S—$R^7$ or —$(C_{1-6})$alkylene-$SO_2$—$R^7$;

wherein $R^7$ is in each instance independently selected from H, $(C_{1-6})$alkyl, $(C_{2-6})$alkenyl, $(C_{1-6})$haloalkyl, $(C_{3-7})$cycloalkyl, aryl and Het;

wherein the Het is selected from the group:

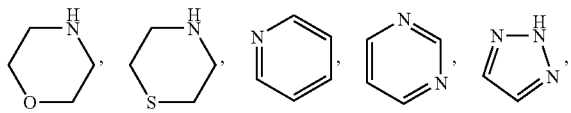

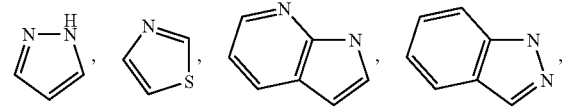

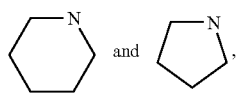

wherein the $(C_{1-6})$alkyl is optionally substituted with 1 or 2 substituents each independently selected from —OH, —O—$(C_{1-6})$alkyl and COOH; and wherein each of the aryl and Het is optionally substituted with 1 to 3 substituents each independently selected from halo, cyano, oxo, imino, —OH, —O—$(C_{1-6})$alkyl, —$NH_2$, —NH$(C_{1-4})$alkyl, —N$((C_{1-4})$alkyl$)_2$, —NH—C(=O)$(C_{1-4})$alkyl, $(C_{1-6})$alkyl and Het, wherein the Het is a 5- or 6-membered heterocycle containing 1 to 4 heteroatoms, each independently selected from N, O and S; and c) —$(C_{1-6})$alkylene-N$(R^8)R^9$ or —$(C_{1-6})$alkylene-C(=O)—N$(R^8)R^9$ wherein $R^8$ is in each instance independently selected from H and $(C_{1-6})$alkyl; and $R^9$ is in each instance independently selected from $R^7$, —O—$(C_{1-6})$alkyl, —$SO_2$—$R^7$, —C(=O)—$R^7$, —C(=O)O$R^7$ and —C(=O)N$(R^8)R^7$; wherein $R^7$ and $R^8$ are as defined above.

$R^{20}$-H: In another embodiment, $R^{20}$ is selected from:

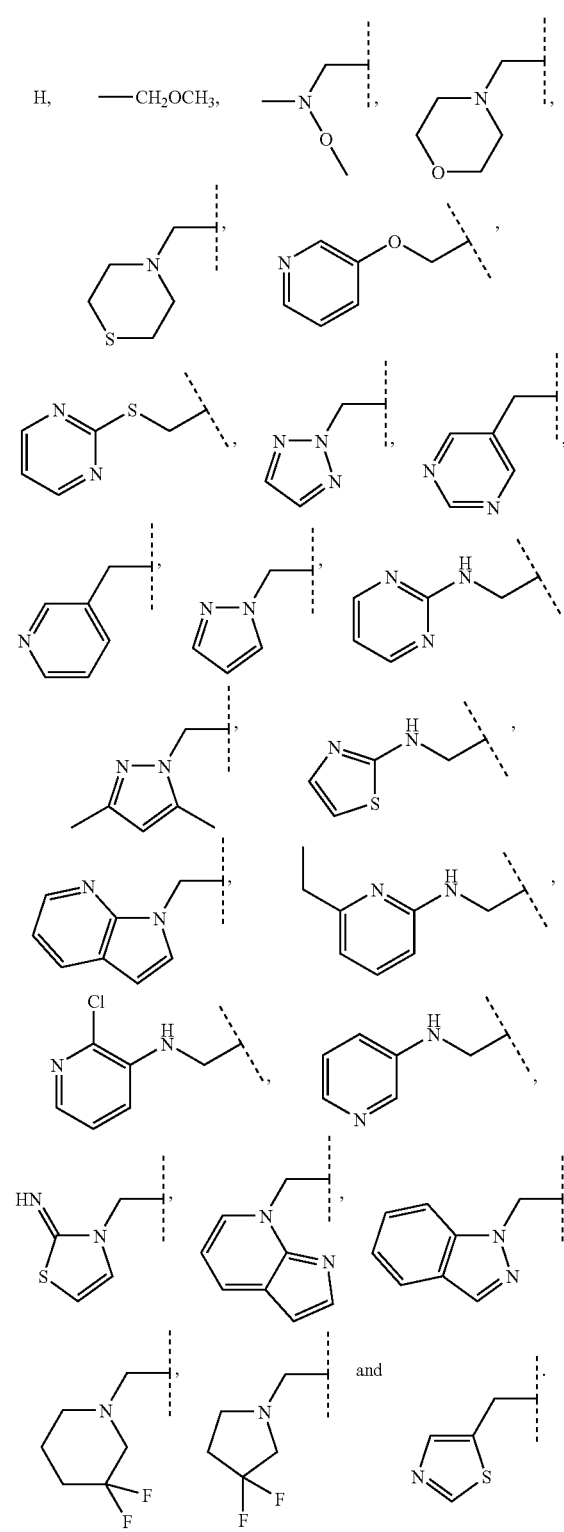

$R^{20}$-I: In another embodiment, $R^{20}$ is selected from:

b) —$(C_{1-3})$alkylene-$R^7$, —$(C_{1-3})$alkylene-O—$R^7$, or —$(C_{1-3})$alkylene-S—$R^7$;

wherein $R^7$ is Het; wherein the Het is a 5- or 6-membered heterocycle containing 1 to 3 nitrogen heteroatoms, or Het is a 9- or 10-membered heteropolycycle containing 1 to 4 nitrogen heteroatoms, wherein each N heteroatom may, independently and where possible, exist in an oxidized state such that it is further bonded to an oxygen atom to form an N-oxide group;
wherein the Het is optionally substituted with 1 to 3 substituents each independently selected from halo, imino, —OH, —O—$(C_{1-6})$alkyl, —O—$(C_{1-6})$haloalkyl, $(C_{3-7})$cycloalkyl, —$NH_2$, —NH$(C_{1-4})$alkyl, —NH$(C_{3-7})$cycloalkyl, —N$((C_{1-4})$alkyl$)(C_{3-7})$cycloalkyl, —N$((C_{1-4})$alkyl$)_2$, —NH—C(=O)$(C_{1-4})$alkyl, $(C_{1-6})$alkyl and c) —$(C_{1-3})$alkylene-N($R^8$)$R^9$ wherein
$R^8$ is in each instance independently selected from H, $(C_{1-6})$alkyl and $(C_{3-7})$cycloalkyl; and
$R^9$ is $R^7$ wherein $R^7$ is as defined above.

Any and each individual definition of $R^{20}$ as set out herein may be combined with any and each individual definition of X, $R^2$, $R^3$, $R^5$ and $R^6$ as set out herein.

$R^3$:
$R^3$-A: In one embodiment, $R^3$ is selected from H, halo, CN, —OH, —O—$(C_{1-4})$alkyl, —S—$(C_{1-4})$alkyl, —$NH_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$.
$R^3$-B: In another embodiment, $R^3$ is selected from H, halo, CN, —O—$(C_{1-4})$alkyl and —N$((C_{1-4})$alkyl$)_2$.
$R^3$-C: In another embodiment, $R^3$ is selected from H, halo and CN.
$R^3$-D: In another embodiment, $R^3$ is selected from H, F, Cl and CN.
$R^3$-E: In another embodiment, $R^3$ is selected from H and halo.
$R^3$-F: In another embodiment, $R^3$ is selected from H, F and Cl.
$R^3$-G: In another embodiment, $R^3$ is H or F.
$R^3$-H: In another embodiment, $R^3$ is H.

Any and each individual definition of $R^3$ as set out herein may be combined with any and each individual definition of X, $R^{20}$, $R^2$, $R^5$ and $R^6$ as set out herein.

$R^5$:
$R^5$-A: In one embodiment, $R^5$ is selected from H, $(C_{1-6})$alkyl, $(C_{3-7})$cycloalkyl, $(C_{3-7})$cycloalkyl-$(C_{1-6})$alkyl- or Het; the $(C_{1-6})$alkyl and Het each being optionally substituted with 1 to 4 substituents each independently selected from $(C_{1-6})$alkyl, $(C_{1-6})$haloalkyl, Het, —OH, —COOH, —C(=O)—$(C_{1-6})$alkyl, —C(=O)—O—$(C_{1-6})$alkyl, —$SO_2(C_{1-6})$alkyl and —C(=O)—N($R^{51}$)$R^{52}$;
wherein $R^{51}$ is H, $(C_{1-6})$alkyl or $(C_{3-7})$cycloalkyl; and
$R^{52}$ is H, $(C_{3-7})$cycloalkyl, aryl, Het, aryl-$(C_{1-3})$alkyl- or Het-$(C_{1-3})$alkyl-;
wherein each of the $(C_{1-6})$alkyl, $(C_{3-7})$cycloalkyl, aryl, Het, aryl-$(C_{1-3})$alkyl- and Het-$(C_{1-3})$alkyl- are optionally substituted with 1 to 3 substituents each independently selected from $(C_{1-6})$alkyl, $(C_{1-6})$haloalkyl, halo, oxo, —OH, —O$(C_{1-6})$alkyl, —$NH_2$, —NH$(C_{1-6})$alkyl, —N$((C_{1-6})$alkyl$)_2$, —NH$(C_{3-7})$cycloalkyl, —N$((C_{1-4})$alkyl$)(C_{3-7})$cycloalkyl, —C(=O)$(C_{1-6})$alkyl and —NHC(=O)—$(C_{1-6})$alkyl;
wherein the $(C_{1-6})$alkyl is optionally substituted with OH; or $R^{51}$ and $R^{52}$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or $SO_2$;
wherein the heterocycle is optionally substituted with 1 to 3 substituents each independently selected from $(C_{1-6})$alkyl, $(C_{1-6})$haloalkyl, halo, oxo, —OH, —O$(C_{1-6})$alkyl, —$NH_2$, —NH$(C_{1-6})$alkyl, —N$((C_{1-6})$alkyl$)_2$, —NH$(C_{3-7})$cycloalkyl, —N$((C_{1-4})$alkyl$)(C_{3-7})$cycloalkyl, —C(=O)$(C_{1-6})$alkyl and —NHC(=O)—$(C_{1-6})$alkyl;
wherein the $(C_{1-6})$alkyl is optionally substituted with OH.

$R^5$-B: In one embodiment, $R^5$ is $(C_{1-6})$alkyl.
$R^5$-C: In another embodiment, $R^5$ is methyl or 1-methylethyl.
$R^5$-D: In another embodiment, $R^5$ is 1-methylethyl.
$R^5$-E: In another embodiment, $R^5$ is $(C_{1-4})$alkyl substituted with $(C_{1-6})$haloalkyl, Het, —COOH or —C(=O)—N($R^{51}$)$R^{52}$, wherein the Het is a 5- or 6-membered heterocycle containing from 1 to 4 N heteroatoms or Het is a 9- or 10-membered bicyclic heteropolycycle containing from 1 to 4 N heteroatoms;
and wherein $R^{51}$ is H or $(C_{1-6})$alkyl and $R^{52}$ is selected from H, $(C_{1-6})$alkyl, $(C_{3-7})$cycloalkyl, Het and Het-$(C_{1-3})$alkyl-;
wherein the $(C_{1-6})$alkyl is optionally substituted with 1 or 2 substituents each independently selected from —O$(C_{1-6})$alkyl and —N$(C_{1-6})$alkyl$)_2$;
and wherein the Het and the Het portion of Het-$(C_{1-3})$alkyl- are each independently a 5- or 6-membered heterocycle containing 1 to 3 heteroatoms each independently selected from N, O and S, wherein the Het and the Het-$(C_{1-3})$alkyl- are each optionally substituted with 1 to 3 substituents each independently selected from halo, oxo, —OH, $(C_{1-6})$alkyl, $(C_{1-6})$haloalkyl, —(C=O)$(C_{1-6})$alkyl, —N$((C_{1-6})$alkyl$)_2$ and —NH(C=O)$(C_{1-6})$alkyl,
wherein the $(C_{1-6})$alkyl is optionally substituted with OH;
or $R^{51}$ and $R^{52}$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or $SO_2$;
wherein the heterocycle is optionally substituted with 1 to 3 substituents each independently selected from halo, oxo, —OH, $(C_{1-6})$alkyl, $(C_{1-6})$haloalkyl, —(C=O)$(C_{1-6})$alkyl, —N$((C_{1-6})$alkyl$)_2$ and —NH(C=O)$(C_{1-6})$alkyl,
wherein the $(C_{1-6})$alkyl is optionally substituted with OH.

$R^5$-F: In another embodiment, $R^5$ is $(C_{1-2})$alkyl substituted with $(C_{1-6})$haloalkyl or Het, wherein the Het is selected from

wherein the Het is optionally substituted with 1 or 2 substituents selected from $(C_{1-4})$alkyl and —N$((C_{1-4})$alkyl$)_2$.
$R^5$-G: In another embodiment, $R^5$ is Het, $(C_{3-7})$cycloalkyl or $(C_{1-6})$alkyl, optionally substituted with $(C_{1-6})$haloalkyl.
$R^5$-H: In another embodiment, $R^5$ is cyclopropyl or cyclobutyl.

R⁵-I: In another embodiment, R⁵ is selected from:

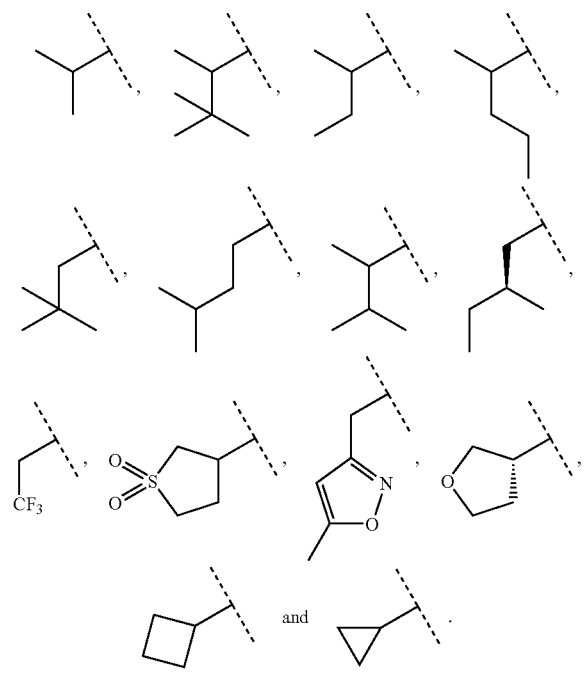

R⁵-J: In another embodiment, R⁵ is Het optionally substituted with 1 to 2 substituents each independently selected from (C$_{1-6}$)alkyl and (C$_{1-6}$)haloalkyl.

R⁵-K: In another embodiment, R⁵ is (C$_{1-6}$)alkyl, (C$_{3-7}$)cycloalkyl, (C$_{3-7}$)cycloalkyl-(C$_{1-6}$)alkyl- or Het; the (C$_{1-6}$)alkyl and Het each being optionally substituted with 1 to 4 substituents each independently selected from (C$_{1-6}$)alkyl, (C$_{1-6}$)haloalkyl, (C$_{3-7}$)cycloalkyl, Het, —OH, —COOH, —C(=O)—(C$_{1-6}$)alkyl, —C(=O)—O—(C$_{1-6}$)alkyl, —SO$_2$(C$_{1-6}$)alkyl and —C(=O)—N(R⁵¹)R⁵²;

wherein R⁵¹ is H, (C$_{1-6}$)alkyl or (C$_{3-7}$)cycloalkyl; and

R⁵² is H, (C$_{1-6}$)alkyl, (C$_{3-7}$)cycloalkyl, aryl, Het, aryl-(C$_{1-3}$)alkyl- or Het-(C$_{1-3}$)alkyl-;

wherein each of the (C$_{1-6}$)alkyl, (C$_{3-7}$)cycloalkyl, aryl, Het, aryl-(C$_{1-3}$)alkyl- and Het-(C$_{1-3}$)alkyl- are optionally substituted with 1 to 3 substituents each independently selected from (C$_{1-6}$)alkyl, (C$_{1-6}$)haloalkyl, halo, oxo, —OH, —O(C$_{1-6}$)alkyl, —NH$_2$, —NH(C$_{1-6}$)alkyl, —N((C$_{1-6}$)alkyl)$_2$, —NH(C$_{3-7}$)cycloalkyl, —N((C$_{1-4}$)alkyl)(C$_{3-7}$)cycloalkyl, —C(=O)(C$_{1-6}$)alkyl and —NHC(=O)—(C$_{1-6}$)alkyl;

wherein the (C$_{1-6}$)alkyl is optionally substituted with OH;

or R⁵¹ and R⁵², together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;

wherein the heterocycle is optionally substituted with 1 to 3 substituents each independently selected from (C$_{1-6}$)alkyl, (C$_{1-6}$)haloalkyl, halo, oxo, OH, —O(C$_{1-6}$)alkyl, —NH$_2$, —NH(C$_{1-6}$)alkyl, —N((C$_{1-6}$)alkyl)$_2$, —NH(C$_{3-7}$)cycloalkyl, —N((C$_{1-4}$)alkyl)(C$_{3-7}$)cycloalkyl, —C(=O)(C$_{1-6}$)alkyl and —NHC(=O)—(C$_{1-6}$)alkyl;

wherein the (C$_{1-6}$)alkyl is optionally substituted with OH.

Any and each individual definition of R⁵ as set out herein may be combined with any and each individual definition of X, R²⁰, R², R³ and R⁶ as set out herein.

R⁶:

R⁶-A: In an alternative embodiment, R⁶ is Het optionally substituted with 1 to 5 substituents each independently selected from halo, (C$_{1-6}$)alkyl, (C$_{1-6}$)haloalkyl, (C$_{3-7}$)cycloalkyl, —OH, —SH, —O—(C$_{1-4}$)alkyl and —S—(C$_{1-4}$)alkyl.

R⁶-B: In another alternative embodiment, R⁶ is Het optionally substituted with 1 to 3 substituents each independently selected from halo, —OH, (C$_{1-4}$)alkyl and (C$_{1-4}$)haloalkyl.

R⁶-C: In yet another alternative embodiment, R⁶ is Het optionally substituted with 1 to 3 substituents each independently selected from F, Cl, Br, OH and methyl.

R⁶-D: In still another embodiment, R⁶ is Het optionally substituted with 1 to 5 substituents each independently selected from halo, (C$_{1-6}$)alkyl, (C$_{1-6}$)haloalkyl, (C$_{3-7}$)cycloalkyl, —OH, —SH, —O—(C$_{1-4}$)alkyl and —S—(C$_{1-4}$)alkyl.

wherein the Het is selected from:

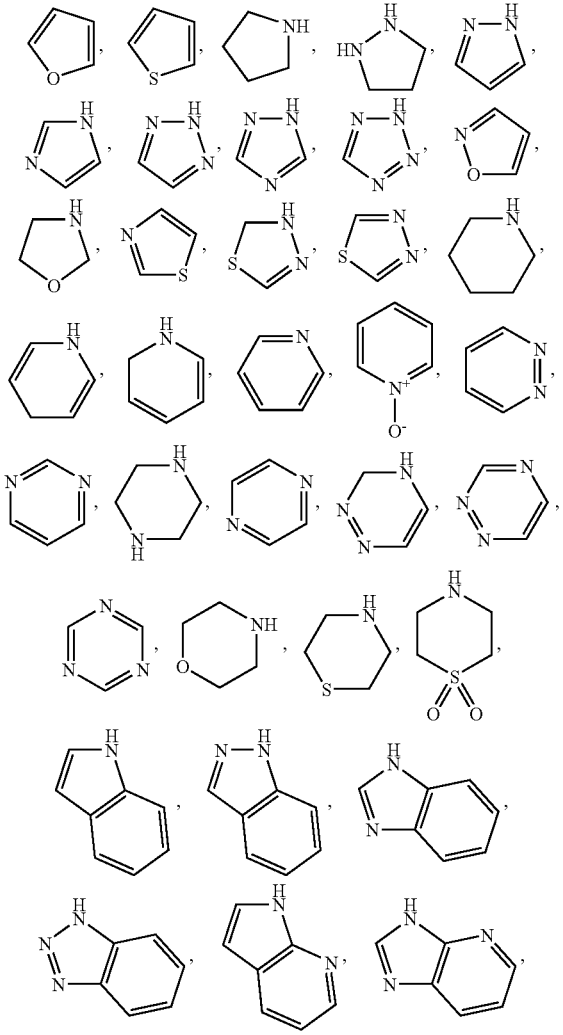

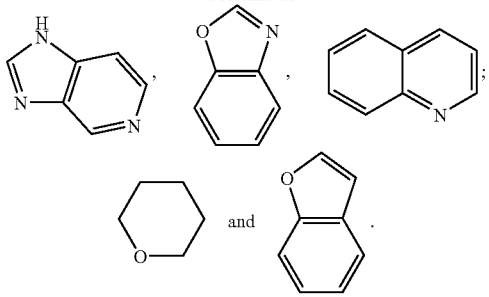

R⁶-E: In still another embodiment, R⁶ is Het optionally substituted with 1 to 3 substituents each independently selected from halo, OH, $(C_{1-6})$alkyl and $(C_{1-6})$haloalkyl wherein the Het is selected from:

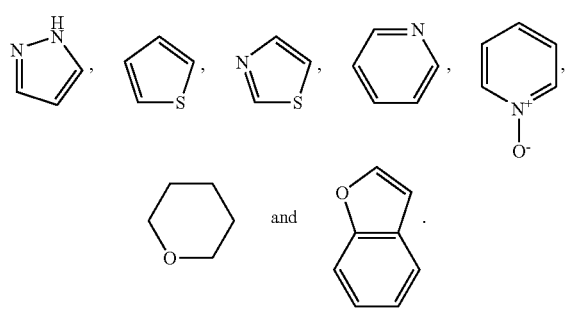

R⁶-F: In still another embodiment, R⁶ is Het optionally substituted with 1 to 3 substituents each independently selected from halo, OH, $(C_{1-4})$alkyl and $(C_{1-4})$haloalkyl wherein the Het is selected from:

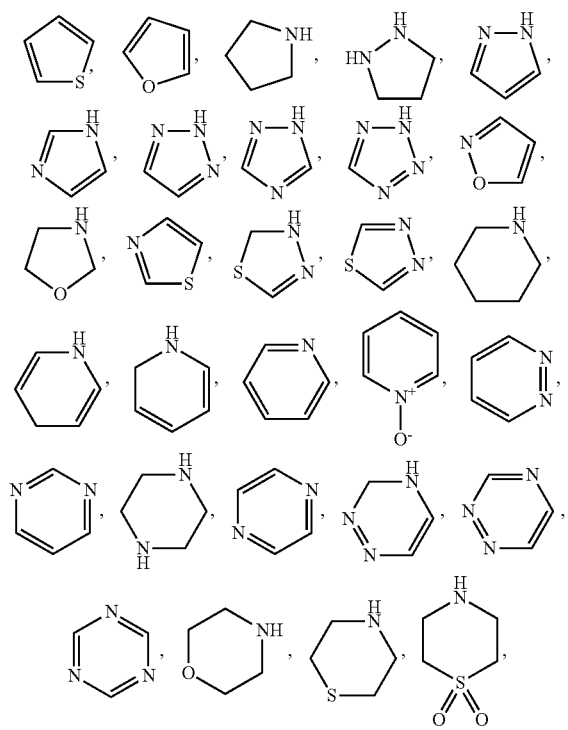

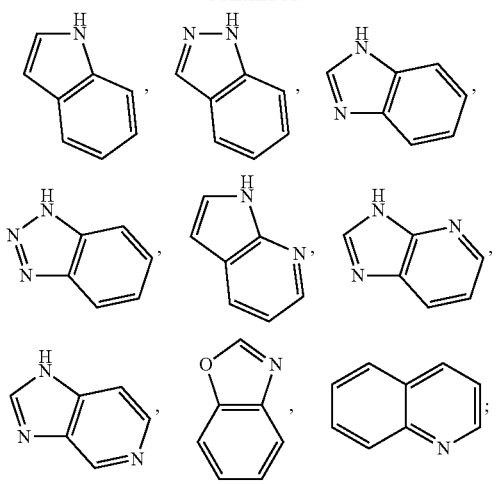

R⁶-G: In still another embodiment, R⁶ is Het, wherein the Het is selected from:

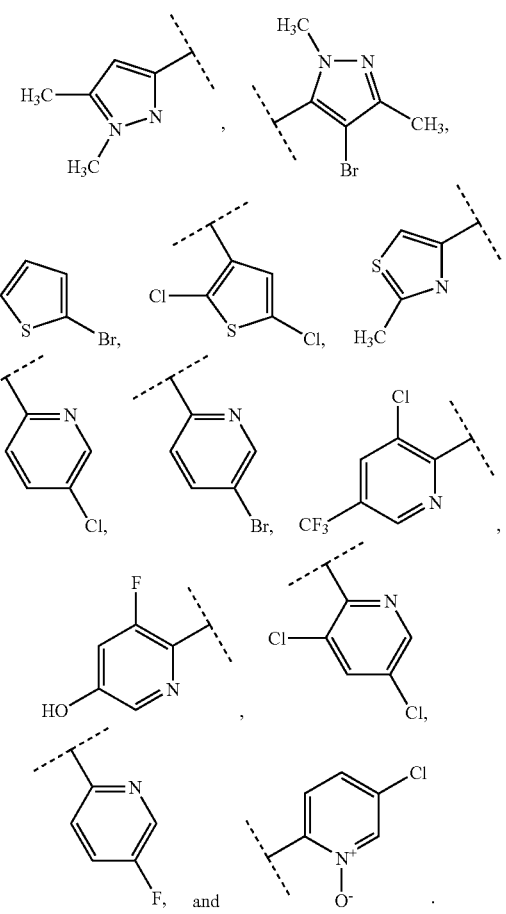

R⁶-H: In still another embodiment, R⁶ is Het optionally substituted with 1 to 2 substituents each independently selected from halo, OH and $(C_{1-6})$haloalkyl and, wherein the Het is

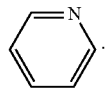

R⁶-I: In still another embodiment, R⁶ is Het, wherein the Het is selected from:

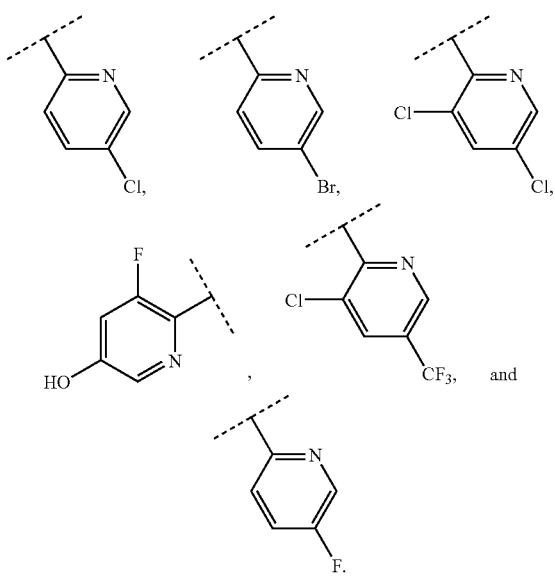

R⁶-J: In still another embodiment, R⁶ is

R⁶-K: In still another embodiment, R⁶ is Het; being optionally substituted with 1 to 5 substituents each independently selected from halo, $(C_{1-6})$alkyl, $(C_{1-6})$haloalkyl, $(C_{3-7})$cycloalkyl, —OH, —SH, —O—$(C_{1-4})$alkyl, —S—$(C_{1-4})$alkyl and —N(R⁸)R⁹; wherein R⁸ is selected from H, $(C_{1-6})$alkyl and $(C_{3-7})$cycloalkyl; and R⁹ is R⁷; wherein R⁷ is selected from H, $(C_{2-6})$alkenyl, $(C_{2-6})$alkynyl, $(C_{1-6})$haloalkyl, $(C_{3-7})$cycloalkyl, aryl and Het;

wherein the $(C_{1-6})$alkyl is optionally substituted with 1 or 2 substituents each independently selected from —OH, —O—$(C_{1-6})$alkyl, cyano, COOH, —NH₂, —NH$(C_{1-4})$alkyl, —NH$(C_{3-7})$cycloalkyl, —N$((C_{1-4})$alkyl)$(C_{3-7})$cycloalkyl and —N$((C_{1-4})$alkyl)₂; and wherein each of the aryl and Het is optionally substituted with 1 to 3 substituents each independently selected from:

i) halo, cyano, oxo, thioxo, imino, —OH, —O—$(C_{1-6})$alkyl, —O—$(C_{1-6})$haloalkyl, $(C_{3-7})$cycloalkyl, $(C_{1-6})$haloalkyl, —C(=O)—$(C_{1-6})$alkyl, —SO₂$(C_{1-6})$alkyl, —C(=O)—NH₂, —C(=O)—NH$(C_{1-4})$alkyl, —C(=O)—N$((C_{1-4})$alkyl)₂, —C(=O)—NH$(C_{3-7})$cycloalkyl, —C(=O)—N$((C_{1-4})$alkyl)$(C_{3-7})$cycloalkyl, —NH₂, —NH$(C_{1-4})$alkyl, —N$((C_{1-4})$alkyl)₂, —NH$(C_{3-7})$cycloalkyl, —N$((C_{1-4})$alkyl)$(C_{3-7})$cycloalkyl or —NH—C(=O)$(C_{1-4})$alkyl;

ii) $(C_{1-6})$alkyl optionally substituted with —OH, —O—$(C_{1-6})$haloalkyl, or —O—$(C_{1-6})$alkyl; and iii) aryl or Het, wherein each of the aryl and Het is optionally substituted with halo or $(C_{1-6})$alkyl;

or R⁸ and R⁹, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO₂;

wherein the heterocycle is optionally substituted with 1 to 3 substituents each independently selected from $(C_{1-6})$alkyl, $(C_{1-6})$haloalkyl, halo, oxo, —OH, SH, —S$(C_{1-6})$alkyl, $(C_{3-7})$cycloalkyl, —NH₂, —NH$(C_{1-6})$alkyl, —N$((C_{1-6})$alkyl)₂, —NH$(C_{3-7})$cycloalkyl, —N$((C_{1-4})$alkyl)$(C_{3-7})$cycloalkyl, —C(=O)$(C_{1-6})$alkyl and —NHC(=O)—$(C_{1-6})$alkyl.

Any and each individual definition of R⁶ as set out herein may be combined with any and each individual definition of X, R², R²⁶, R³ and R⁵ as set out herein.

Examples of preferred subgeneric embodiments of the present invention are set forth in the following table, wherein each substituent group of each embodiment is defined according to the definitions set forth above:

| Embodiment | X | R² | R²⁰ | R³ | R⁵ | R⁶ |
|---|---|---|---|---|---|---|
| E-1 | X-A | R²-A | R²⁰-A | R³-A | R⁵-A | R⁶-B |
| E-2 | X-A | R²-A | R²⁰-E | R³-C | R⁵-A | R⁶-H |
| E-3 | X-A | R²-A | R²⁰-A | R³-A | R⁵-A | R⁶-B |
| E-4 | X-A | R²-A | R²⁰-E | R³-C | R⁵-A | R⁶-J |
| E-5 | X-A | R²-A | R²⁰-A | R³-A | R⁵-A | R⁶-J |
| E-6 | X-A | R²-A | R²⁰-A | R³-C | R⁵-A | R⁶-A |
| E-7 | X-A | R²-A | R²⁰-A | R³-A | R⁵-C | R⁶-I |
| E-8 | X-A | R²-B | R²⁰-E | R³-A | R⁵-A | R⁶-A |
| E-9 | X-A | R²-B | R²⁰-G | R³-A | R⁵-A | R⁶-J |
| E-10 | X-A | R²-B | R²⁰-A | R³-C | R⁵-A | R⁶-J |
| E-11 | X-A | R²-B | R²⁰-A | R³-A | R⁵-D | R⁶-A |
| E-12 | X-A | R²-F | R²⁰-E | R³-C | R⁵-G | R⁶-B |
| E-13 | X-A | R²-F | R²⁰-E | R³-A | R⁵-G | R⁶-J |
| E-14 | X-A | R²-F | R²⁰-A | R³-C | R⁵-D | R⁶-A |
| E-15 | X-A | R²-G | R²⁰-E | R³-C | R⁵-G | R⁶-B |
| E-16 | X-A | R²-G | R²⁰-E | R³-A | R⁵-G | R⁶-J |
| E-17 | X-A | R²-G | R²⁰-A | R³-C | R⁵-D | R⁶-A |
| E-18 | X-A | R²-J | R²⁰-E | R³-C | R⁵-G | R⁶-B |
| E-19 | X-A | R²-J | R²⁰-E | R³-A | R⁵-G | R⁶-J |
| E-20 | X-A | R²-J | R²⁰-A | R³-C | R⁵-D | R⁶-A |
| E-21 | X-A | R²-K | R²⁰-E | R³-C | R⁵-G | R⁶-B |
| E-22 | X-A | R²-K | R²⁰-E | R³-A | R⁵-G | R⁶-J |
| E-23 | X-A | R²-K | R²⁰-A | R³-C | R⁵-D | R⁶-A |
| E-24 | X-A | R²-L | R²⁰-A | R³-A | R⁵-A | R⁶-A |
| E-25 | X-A | R²-L | R²⁰-C | R³-A | R⁵-A | R⁶-A |
| E-26 | X-A | R²-L | R²⁰-C | R³-G | R⁵-G | R⁶-B |
| E-27 | X-A | R²-L | R²⁰-D | R³-D | R⁵-D | R⁶-J |
| E-28 | X-A | R²-L | R²⁰-D | R³-G | R⁵-G | R⁶-A |
| E-29 | X-A | R²-L | R²⁰-C | R³-B | R⁵-B | R⁶-B |
| E-30 | X-A | R²-L | R²⁰-D | R³-E | R⁵-E | R⁶-A |
| E-31 | X-A | R²-L | R²⁰-C | R³-G | R⁵-G | R⁶-B |
| E-32 | X-A | R²-L | R²⁰-A | R³-G | R⁵-G | R⁶-J |
| E-33 | X-A | R²-L | R²⁰-C | R³-D | R⁵-D | R⁶-H |
| E-34 | X-A | R²-M | R²⁰-A | R³-A | R⁵-A | R⁶-A |
| E-35 | X-A | R²-M | R²⁰-C | R³-A | R⁵-A | R⁶-A |

| Embodiment | X | $R^2$ | $R^{20}$ | $R^3$ | $R^5$ | $R^6$ |
|---|---|---|---|---|---|---|
| E-36 | X-A | $R^2$-M | $R^{20}$-C | $R^3$-G | $R^5$-G | $R^6$-B |
| E-37 | X-A | $R^2$-M | $R^{20}$-D | $R^3$-D | $R^5$-D | $R^6$-J |
| E-38 | X-A | $R^2$-M | $R^{20}$-D | $R^3$-G | $R^5$-G | $R^6$-A |
| E-39 | X-A | $R^2$-M | $R^{20}$-C | $R^3$-B | $R^5$-B | $R^6$-B |
| E-40 | X-A | $R^2$-M | $R^{20}$-D | $R^3$-E | $R^5$-E | $R^6$-A |
| E-41 | X-A | $R^2$-M | $R^{20}$-C | $R^3$-G | $R^5$-G | $R^6$-B |
| E-42 | X-A | $R^2$-M | $R^{20}$-A | $R^3$-G | $R^5$-G | $R^6$-J |
| E-43 | X-A | $R^2$-M | $R^{20}$-C | $R^3$-D | $R^5$-D | $R^6$-H |
| E-44 | X-A | $R^2$-C | $R^{20}$-A | $R^3$-F | $R^5$-G | $R^6$-D |
| E-45 | X-A | $R^2$-C | $R^{20}$-C | $R^3$-G | $R^5$-C | $R^6$-C |
| E-46 | X-A | $R^2$-C | $R^{20}$-C | $R^3$-G | $R^5$-G | $R^6$-B |
| E-47 | X-A | $R^2$-C | $R^{20}$-A | $R^3$-G | $R^5$-G | $R^6$-J |
| E-48 | X-A | $R^2$-C | $R^{20}$-C | $R^3$-D | $R^5$-D | $R^6$-H |
| E-49 | X-A | $R^2$-C | $R^{20}$-G | $R^3$-H | $R^5$-H | $R^6$-E |
| E-50 | X-A | $R^2$-C | $R^{20}$-H | $R^3$-H | $R^5$-A | $R^6$-G |
| E-51 | X-A | $R^2$-C | $R^{20}$-J | $R^3$-F | $R^5$-I | $R^6$-D |
| E-52 | X-A | $R^2$-C | $R^{20}$-J | $R^3$-D | $R^5$-J | $R^6$-B |
| E-53 | X-A | $R^2$-D | $R^{20}$-D | $R^3$-D | $R^5$-D | $R^6$-J |
| E-54 | X-A | $R^2$-D | $R^{20}$-D | $R^3$-G | $R^5$-G | $R^6$-A |
| E-55 | X-A | $R^2$-D | $R^{20}$-C | $R^3$-B | $R^5$-B | $R^6$-B |
| E-56 | X-A | $R^2$-D | $R^{20}$-I | $R^3$-H | $R^5$-H | $R^6$-B |
| E-57 | X-A | $R^2$-D | $R^{20}$-G | $R^3$-E | $R^5$-J | $R^6$-G |
| E-58 | X-A | $R^2$-D | $R^{20}$-B | $R^3$-D | $R^5$-D | $R^6$-D |
| E-59 | X-A | $R^2$-D | $R^{20}$-D | $R^3$-D | $R^5$-D | $R^6$-J |
| E-60 | X-A | $R^2$-D | $R^{20}$-D | $R^3$-D | $R^5$-D | $R^6$-C |
| E-61 | X-A | $R^2$-D | $R^{20}$-C | $R^3$-A | $R^5$-H | $R^6$-C |
| E-62 | X-A | $R^2$-D | $R^{20}$-A | $R^3$-C | $R^5$-A | $R^6$-F |
| E-63 | X-A | $R^2$-D | $R^{20}$-C | $R^3$-F | $R^5$-J | $R^6$-B |
| E-64 | X-A | $R^2$-D | $R^{20}$-C | $R^3$-E | $R^5$-D | $R^6$-A |
| E-65 | X-A | $R^2$-E | $R^{20}$-C | $R^3$-D | $R^5$-D | $R^6$-H |
| E-66 | X-A | $R^2$-E | $R^{20}$-C | $R^3$-G | $R^5$-G | $R^6$-B |
| E-67 | X-A | $R^2$-E | $R^{20}$-C | $R^3$-D | $R^5$-D | $R^6$-J |
| E-68 | X-A | $R^2$-E | $R^{20}$-D | $R^3$-G | $R^5$-G | $R^6$-A |
| E-69 | X-A | $R^2$-E | $R^{20}$-C | $R^3$-B | $R^5$-B | $R^6$-B |
| E-70 | X-A | $R^2$-E | $R^{20}$-D | $R^3$-E | $R^5$-E | $R^6$-A |
| E-71 | X-A | $R^2$-E | $R^{20}$-C | $R^3$-G | $R^5$-G | $R^6$-B |
| E-72 | X-A | $R^2$-H | $R^{20}$-A | $R^3$-G | $R^5$-G | $R^6$-J |
| E-73 | X-A | $R^2$-H | $R^{20}$-C | $R^3$-D | $R^5$-D | $R^6$-H |
| E-74 | X-A | $R^2$-H | $R^{20}$-G | $R^3$-H | $R^5$-H | $R^6$-E |
| E-75 | X-A | $R^2$-H | $R^{20}$-H | $R^3$-H | $R^5$-A | $R^6$-G |
| E-76 | X-A | $R^2$-H | $R^{20}$-J | $R^3$-F | $R^5$-I | $R^6$-D |
| E-77 | X-A | $R^2$-H | $R^{20}$-J | $R^3$-D | $R^5$-J | $R^6$-B |
| E-78 | X-A | $R^2$-I | $R^{20}$-C | $R^3$-D | $R^5$-D | $R^6$-H |
| E-79 | X-A | $R^2$-I | $R^{20}$-C | $R^3$-G | $R^5$-G | $R^6$-B |
| E-80 | X-A | $R^2$-I | $R^{20}$-D | $R^3$-D | $R^5$-D | $R^6$-J |
| E-81 | X-A | $R^2$-I | $R^{20}$-D | $R^3$-G | $R^5$-G | $R^6$-A |
| E-82 | X-A | $R^2$-I | $R^{20}$-C | $R^3$-B | $R^5$-B | $R^6$-B |
| E-83 | X-A | $R^2$-I | $R^{20}$-D | $R^3$-E | $R^5$-E | $R^6$-A |
| E-84 | X-A | $R^2$-I | $R^{20}$-A | $R^3$-G | $R^5$-G | $R^6$-J |
| E-85 | X-A | $R^2$-I | $R^{20}$-C | $R^3$-D | $R^5$-D | $R^6$-H |
| E-86 | X-B | $R^2$-A | $R^{20}$-A | $R^3$-A | $R^5$-A | $R^6$-B |
| E-87 | X-B | $R^2$-A | $R^{20}$-E | $R^3$-C | $R^5$-A | $R^6$-H |
| E-88 | X-B | $R^2$-A | $R^{20}$-A | $R^3$-A | $R^5$-A | $R^6$-B |
| E-89 | X-B | $R^2$-A | $R^{20}$-E | $R^3$-C | $R^5$-A | $R^6$-J |
| E-90 | X-B | $R^2$-F | $R^{20}$-E | $R^3$-C | $R^5$-G | $R^6$-B |
| E-91 | X-B | $R^2$-F | $R^{20}$-E | $R^3$-A | $R^5$-G | $R^6$-J |
| E-92 | X-B | $R^2$-F | $R^{20}$-A | $R^3$-C | $R^5$-D | $R^6$-A |
| E-93 | X-B | $R^2$-G | $R^{20}$-E | $R^3$-C | $R^5$-G | $R^6$-B |
| E-94 | X-B | $R^2$-G | $R^{20}$-E | $R^3$-A | $R^5$-G | $R^6$-J |
| E-95 | X-B | $R^2$-G | $R^{20}$-A | $R^3$-C | $R^5$-G | $R^6$-A |
| E-96 | X-B | $R^2$-J | $R^{20}$-E | $R^3$-C | $R^5$-G | $R^6$-B |
| E-97 | X-B | $R^2$-J | $R^{20}$-E | $R^3$-A | $R^5$-G | $R^6$-J |
| E-98 | X-B | $R^2$-I | $R^{20}$-A | $R^3$-C | $R^5$-D | $R^6$-A |
| E-99 | X-B | $R^2$-K | $R^{20}$-E | $R^3$-C | $R^5$-G | $R^6$-B |
| E-100 | X-B | $R^2$-K | $R^{20}$-E | $R^3$-A | $R^5$-G | $R^6$-J |
| E-101 | X-B | $R^2$-K | $R^{20}$-A | $R^3$-C | $R^5$-D | $R^6$-A |
| E-102 | X-B | $R^2$-L | $R^{20}$-C | $R^3$-C | $R^5$-G | $R^6$-B |
| E-103 | X-B | $R^2$-L | $R^{20}$-D | $R^3$-D | $R^5$-D | $R^6$-J |
| E-104 | X-B | $R^2$-L | $R^{20}$-D | $R^3$-G | $R^5$-G | $R^6$-A |
| E-105 | X-B | $R^2$-L | $R^{20}$-C | $R^3$-B | $R^5$-B | $R^6$-B |
| E-106 | X-B | $R^2$-L | $R^{20}$-D | $R^3$-E | $R^5$-E | $R^6$-A |
| E-107 | X-B | $R^2$-L | $R^{20}$-C | $R^3$-G | $R^5$-G | $R^6$-B |
| E-108 | X-B | $R^2$-L | $R^{20}$-A | $R^3$-G | $R^5$-G | $R^6$-J |
| E-109 | X-B | $R^2$-L | $R^{20}$-C | $R^3$-D | $R^5$-D | $R^6$-H |
| E-110 | X-B | $R^2$-M | $R^{20}$-C | $R^3$-G | $R^5$-G | $R^6$-B |
| E-111 | X-B | $R^2$-M | $R^{20}$-D | $R^3$-D | $R^5$-D | $R^6$-J |
| E-112 | X-B | $R^2$-M | $R^{20}$-D | $R^3$-G | $R^5$-G | $R^6$-A |
| E-113 | X-B | $R^2$-M | $R^{20}$-C | $R^3$-B | $R^5$-B | $R^6$-B |
| E-114 | X-B | $R^2$-M | $R^{20}$-D | $R^3$-E | $R^5$-E | $R^6$-A |
| E-115 | X-B | $R^2$-M | $R^{20}$-C | $R^3$-G | $R^5$-G | $R^6$-B |
| E-116 | X-B | $R^2$-M | $R^{20}$-A | $R^3$-G | $R^5$-G | $R^6$-J |
| E-117 | X-B | $R^2$-M | $R^{20}$-C | $R^3$-D | $R^5$-D | $R^6$-H |

Examples of most preferred compounds according to this invention are each single compounds listed in the following Tables 1 and 2.

In general, all tautomeric and isomeric forms and mixtures thereof, for example, individual geometric isomers, stereoisomers, atropisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000, herein incorporated by reference. Furthermore, there are equally well-known methods for the quantitation of enantiomeric excess or purity, for example, GC, HPLC, CE, or NMR, and assignment of absolute configuration and conformation, for example, CD, ORD, X-ray crystallography, or NMR.

The compounds according to the present invention are inhibitors of the hepatitis C virus NS58 RNA-dependent RNA polymerase and thus may be used to inhibit replication of hepatitis C viral RNA.

A compound according to the present invention may also be used as a laboratory reagent or a research reagent. For example, a compound of the present invention may be used as positive control to validate assays, including but not limited to surrogate cell-based assays and in vitro or in vivo viral replication assays.

Compounds according to the present invention may also be used as probes to study the hepatitis C virus NS5B polymerase, including but not limited to the mechanism of action of the polymerase, conformational changes undergone by the polymerase under various conditions and interactions with entities which bind to or otherwise interact with the polymerase.

Compounds of the invention used as probes may be labelled with a label which allows recognition either directly or indirectly of the compound such that it can be detected, measured and quantified. Labels contemplated for use with the compounds of the invention include, but are not limited to, fluorescent labels, chemiluminescent labels, colorimetric labels, enzymatic markers, radioactive isotopes, affinity tags and photoreactive groups.

Compounds of the invention used as probes may also be labelled with an affinity tag whose strong affinity for a receptor can be used to extract from a solution the entity to which the ligand is attached. Affinity tags include but are not limited to biotin or a derivative thereof, a histidine polypeptide, a polyarginine, an amylose sugar moiety or a defined epitope recognizable by a specific antibody.

Furthermore, compounds of the invention used as probes may be labelled with a photoreactive group which is transformed, upon activation by light, from an inert group to a reactive species, such as a free radical. Photoreactive groups include but are not limited to photoaffinity labels such as benzophenone and azide groups.

Furthermore, a compound according to the present invention may be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

Pharmaceutical Composition

Compounds of the present invention may be administered to a mammal in need of treatment for hepatitis C viral infection as a pharmaceutical composition comprising a therapeutically effective amount of a compound according to the invention or a pharmaceutically acceptable salt or ester thereof; and one or more conventional non-toxic pharmaceutically-acceptable carriers, adjuvants or vehicles. The specific formulation of the composition is determined by the solubility and chemical nature of the compound, the chosen route of administration and standard pharmaceutical practice. The pharmaceutical composition according to the present invention may be administered orally or systemically.

For oral administration, the compound, or a pharmaceutically acceptable salt or ester thereof, can be formulated in any orally acceptable dosage form including but not limited to aqueous suspensions and solutions, capsules, powders, syrups, elixirs or tablets. For systemic administration, including but not limited to administration by subcutaneous, intracutaneous, intravenous, intramuscular, intra-articular, intrasynovial, intrasternal, intrathecal, and intralesional injection or infusion techniques, it is preferred to use a solution of the compound, or a pharmaceutically acceptable salt or ester thereof, in a pharmaceutically acceptable sterile aqueous vehicle.

Pharmaceutically acceptable carriers, adjuvants, vehicles, excipients and additives as well as methods of formulating pharmaceutical compositions for various modes of administration are well-known to those of skill in the art and are described in pharmaceutical texts such as Remington: The Science and Practice of Pharmacy, 21st Edition, Lippincott Williams & Wilkins, 2005; and L. V. Allen, N. G. Popovish and H. C. Ansel, Pharmaceutical Dosage Forms and Drug Delivery Systems, 8th ed., Lippincott Williams & Wilkins, 2004, herein incorporated by reference.

The dosage administered will vary depending upon known factors, including but not limited to the activity and pharmacodynamic characteristics of the specific compound employed and its mode, time and route of administration; the age, diet, gender, body weight and general health status of the recipient; the nature and extent of the symptoms; the severity and course of the infection; the kind of concurrent treatment; the frequency of treatment; the effect desired; and the judgment of the treating physician. In general, the compound is most desirably administered at a dosage level that will generally afford antivirally effective results without causing any harmful or deleterious side effects.

A daily dosage of active ingredient can be expected to be about 0.01 to about 200 milligrams per kilogram of body weight, with the preferred dose being about 0.1 to about 50 mg/kg. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Combination Therapy

Combination therapy is contemplated wherein a compound according to the invention, or a pharmaceutically acceptable salt or ester thereof, is co-administered with at least one additional antiviral agent. The additional agents may be combined with compounds of this invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt or ester thereof, and one or more additional antiviral agent, both the compound and the additional agent should be present at dosage levels of between about 10 to 100%, and more preferably between about 10 and 80% of the dosage normally administered in a monotherapy regimen. In the case of a synergistic interaction between the compound of the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, α-, β-, δ-, ω-, and τ-interferons, while examples of class II interferons include, but are not limited to, γ-interferons.

Inhibitors of HCV NS3 protease include agents (compounds or biologicals) that are effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700, WO 2006/007708, WO 2007/009227 (all by Boehringer Ingelheim), WO 02/060926, WO 03/053349, WO 03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune), WO 01/77113, WO 01/81325, WO 02/08187, WO 02/08198, WO 02/08244, WO 02/08256, WO 02/48172, WO 03/062228, WO 03/062265, WO 2005/021584, WO 2005/030796, WO 2005/058821, WO 2005/051980, WO 2005/085197, WO 2005/085242, WO 2005/085275, WO 2005/087721, WO 2005/087725, WO 2005/087730, WO 2005/087731, WO 2005/107745 and WO 2005/113581 (all by Schering), WO 2006/119061, WO 2007/016441, WO 2007/015855, WO 2007/015787 (all by Merck); and the candidates VX-950, ITMN-191 and SCH-503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388, WO 2006/007693, WO 2007/019674, WO 2007/087717 (all by Boehringer Ingelheim), WO 01/47883 (Japan Tobacco), WO 03/000254 (Japan Tobacco), WO 03/026587 (BMS), WO 2004/087714 (IRBM), WO 2005/012288 (Genelabs), WO 2005/014543 (Japan Tobacco), WO 2005/049622 (Japan Tobacco), and WO 2005/121132 (Shionogi), WO 2005/080399 (Japan Tobacco), WO 2006/052013 (Japan Tobacco), WO 2006/119646 (Virochem Pharma), WO 2007/039146 (SmithKline Beecham), WO 2005/021568 (Biota), WO 2006/094347 (Biota) and the candidates HCV 796 (ViroPharma/Wyeth), R-1626, R-1656 and R-7128 (Roche), NM 283 (Idenix/Novartis), VCH-759 (Virochem), GSK625433 (GSK), GS9190 (Gilead), MK-608 (Merck) and PF868554 (Pfizer).

Inhibitors of another target in the HCV life cycle include agents (compounds or biologicals) that are effective to inhibit the formation and/or replication of HCV other than by inhibiting the function of the HCV NS3 protease or HCV polymerase. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

HIV inhibitors include agents (compounds or biologicals) that are effective to inhibit the formation and/or replication of HIV. This includes but is not limited to agents that interfere with either host or viral mechanisms necessary for the formation and/or replication of HIV in a mammal. HIV inhibitors include, but are not limited to;
  NRTIs (nucleoside or nucleotide reverse transcriptase inhibitors; including but not limited to zidovudine, didanosine, zalcitabine, stavudine, lamivudine, emtricitabine, abacavir, and tenofovir);
  NNRTIs (non-nucleoside reverse transcriptase inhibitors; including but not limited to nevirapine, delavirdine, efavirenz, etravirine, rilpivirine and BILR 355);
  protease inhibitors (including but not limited to ritonavir, tipranavir, saquinavir, nelfinavir, indinavir, amprenavir, fosamprenavir, atazanavir, lopinavir, darunavir and brecanavir);
  entry inhibitors including but not limited to
    CCR5 antagonists (including but not limited to maraviroc (UK-427,857) and TAK-652),
    CXCR4 antagonists (including but not limited to AMD-11070),
    fusion inhibitors (including but not limited to enfuvirtide (T-20)) and
    others (including but not limited to BMS-488043);
  integrase inhibitors (including but not limited to MK-0518, c-1605, BMS-538158 and GS 9137);
  TAT inhibitors;
  maturation inhibitors (including but not limited to bevirimat (PA-457)); and
  immunomodulating agents (including but not limited to levamisole).

HAV inhibitors include agents (compounds or biologicals) that are effective to inhibit the formation and/or replication of HAV. This includes but is not limited to agents that interfere with either host or viral mechanisms necessary for the formation and/or replication of HAV in a mammal. HAV inhibitors include but are not limited to Hepatitis A vaccines.

HBV inhibitors include agents (compounds or biologicals) that are effective to inhibit the formation and/or replication of HBV in a mammal. This includes but is not limited to agents that interfere with either host or viral mechanisms necessary for the formation and/or replication of HBV in a mammal. HBV inhibitors include, but are not limited to, agents that inhibit the HBV viral DNA polymerase and HBV vaccines.

Therefore, according to one embodiment, the pharmaceutical composition of this invention additionally comprises a therapeutically effective amount of one or more antiviral agents.

A further embodiment provides the pharmaceutical composition of this invention wherein the one or more antiviral agent comprises at least one other anti-HCV agent.

According to a more specific embodiment of the pharmaceutical composition of this invention, the at least one other anti-HCV agent comprises at least one immunomodulatory agent.

According to another more specific embodiment of the pharmaceutical composition of this invention, the at least one other anti-HCV agent comprises at least one other inhibitor of HCV polymerase.

According to yet another more specific embodiment of the pharmaceutical composition of this invention, the at least one other anti-HCV agent comprises at least one inhibitor of HCV NS3 protease.

According to still another more specific embodiment of the pharmaceutical composition of this invention, the at least one other anti-HCV agent comprises at least one inhibitor of another target in the HCV life cycle.

All of the documents cited herein are incorporated in to the invention as a reference, as if each of them is individually incorporated. Further, it would be appreciated that, in the above teaching of invention, the silted in the art could make certain changes or modifications to the invention, and these equivalents would still be within the scope of the invention defined by the appended claims of the application.

EXAMPLES

Other features of the present invention will become apparent from the following non-limiting examples which illustrate, by way of example, the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is carried out on silica gel ($SiO_2$) according to the procedure of W. C. Still et al., J. Org. Chem., (1978), 43, 2923. Mass spectral analyses are recorded using electrospray mass spectrometry. Purification on a combiflash is performed using an Isco Combiflash (column cartridge $SiO_2$). Preparative HPLC is carried our under standard conditions using a SunFire™ Prep C18 OBD 5 μM reverse phase column, 19×50 mm and a linear gradient (20 to 98%) employing 0.1% TFA/acetonitrile and 0.1% TFA/water as solvents. Compounds are isolated as TFA salts when applicable. Analytical HPLC is carried out under standard conditions using a Combiscreen™ ODS-AQ C18 reverse phase column, YMC, 50×4.6 mm i.d., 5 μM, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein include:
Ac: acetyl;
AcOH: acetic acid;
Bn: benzyl (phenylmethyl);
Bu: butyl;
n-BuLi: n-butyllithium;
m-CPBA: meta-chloroperbenzoic acid;
DBU: 1,8-diazabicyclo[5.4.0]undec-7-ene;
DCE: dichloroethane;
DCM: dichloromethane;
DIAD: diisopropyl azodicarboxylate;
DMAP: 4-dimethylaminopyridine;
DMF: N,N-dimethylformamide;
DMSO: dimethylsulfoxide;
$EC_{50}$: 50% effective concentration;
EDTA: ethylenediaminetetracetic acid;
Et: ethyl;
$Et_3N$: triethylamine;
$Et_2O$: diethyl ether;
EtOAc: ethyl acetate;
EtOH: ethanol;
HPLC: high performance liquid chromatography;
Hex: hexane;
$IC_{50}$: 50% inhibitory concentration;
LC-MS: liquid chromatography-mass spectrometry;
Pr or i-Pr: 1-methylethyl (iso-propyl);
Me: methyl;
MeCN: acetonitrile;
MeI: iodomethane;
MeOH: methanol;
MS: mass spectrometry;
$NaHB(OAc)_3$: sodium triactoxyborohydride;
NIS: N-iodosuccinamide;
NLIN: non-linear;
NMO: N-methylmorpholine N-oxide;
NMR: nuclear magnetic resonance spectroscopy;
Ph: phenyl;
Pr: propyl;
RT: room temperature (approximately 18° C. to 25° C.);
SAS: small-angle scattering;
SPA: scintillation proximity assay;
TCEP: tris(2-carboxyethyl)phosphine hydrochloride;
Pert-butyl or t-butyl: 1,1-dimethylethyl;
TFA: trifluoroacetic acid;
THF: tetrahydrofuran;
TLC: thin layer chromatography.

Example 1A

Preparation of Compound 1001

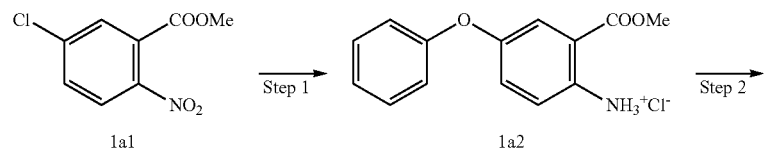

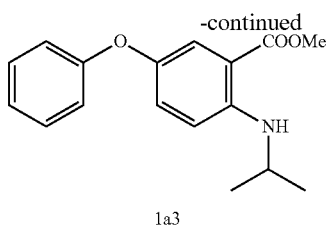

1a3

Step 4

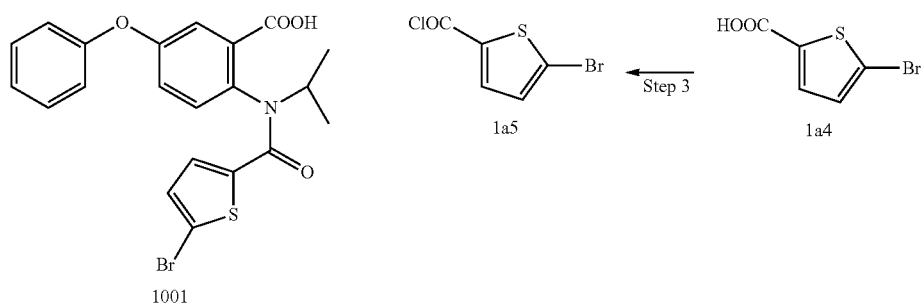

Step 1a:

To a mixture of phenol (5.0 g, 53 mmol) and methyl-5-chloro-2-nitrobenzoate 1a1 (7.6 g, 35 mmol) in DMSO (20 mL) is added anhydrous $K_2CO_3$ (7.3 g, 53 mmol). The mixture is heated to 90° C. and stirred 6 hours. The mixture is diluted in water then extracted with EtOAc (×2). The combined organic extracts are washed with brine, dried over $MgSO_4$, filtered and concentrated under reduced pressure.

Step 1b:

The crude diarylether is diluted in MeOH and 10% Pd $(OH)_2/C$ (0.3 g) is added. The vessel is purged with $H_2$ then is stirred overnight under 1 atm of $H_2$. The mixture is filtered through a pad of celite then is concentrated in vacuo. To a mixture of the crude aniline in anhydrous $Et_2O$ (150 mL) is slowly added HCl (1 M in ether, 150 mL). The resulting solid hydrochloride salt 1a2 is collected by filtration and washed with excess ether and dried.

Step 2:

Reference: Abdel-Magid, A. F.; Carson, K. G.; Harris, B. D.; Maryanoff, C. A.; Shah, R. D. *J. Org. Chem.* 1996, 61, 3849.

To a mixture of aniline hydrochloride salt 1a2 (268 mg, 0.96 mmol) in anhydrous DCE (5 mL) is added 2-methoxypropene (0.37 mL, 3.8 mmol) followed by $NaHB(OAc)_3$ (407 mg, 1.9 mmol). The mixture is stirred overnight at room temperature then is diluted in EtOAc and washed with saturated aqueous $NaHCO_3$ and brine. The organic phase is dried over $MgSO_4$, filtered then concentrated under reduced pressure. The resulting residue is subjected to flash chromatography to isolate isopropylaniline 1a3.

Step 3:

To a mixture of 5-bromo-2-thiophenecarboxylic acid 1a4 (56 mg, 0.27 mmol) and anhydrous $CH_2Cl_2$ (400 mL) is added a drop of anhydrous DMF followed by $(COCl)_2$ (2.0 M in DCM, 0.34 mL, 0.68 mmol). The mixture stirs 20 minutes at RT before being concentrated under reduced pressure to yield the crude acid chloride 1a5.

Step 4:

The crude acid chloride 1a5 is diluted in anhydrous pyridine (1 mL) and i-Pr-aniline 1a3 (50 mg, 0.18 mmol) is added. The mixture stirs overnight at RT. Aqueous NaOH (10 N, 180 μL, 1.8 mmol) and water (180 μL) are added and the mixture stirs overnight at RT. The mixture is diluted in EtOAc and washed with 1N HCl and brine. The organic phase is dried over $MgSO_4$, filtered and concentrated under reduced pressure. The residue is triturated in $Et_2O$ and hexanes to provide compound 1001.

Example 2A

Preparation of Intermediate 2a3

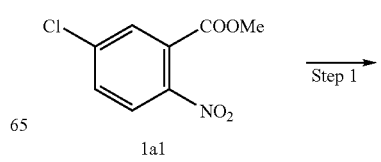

1a1

Step 1

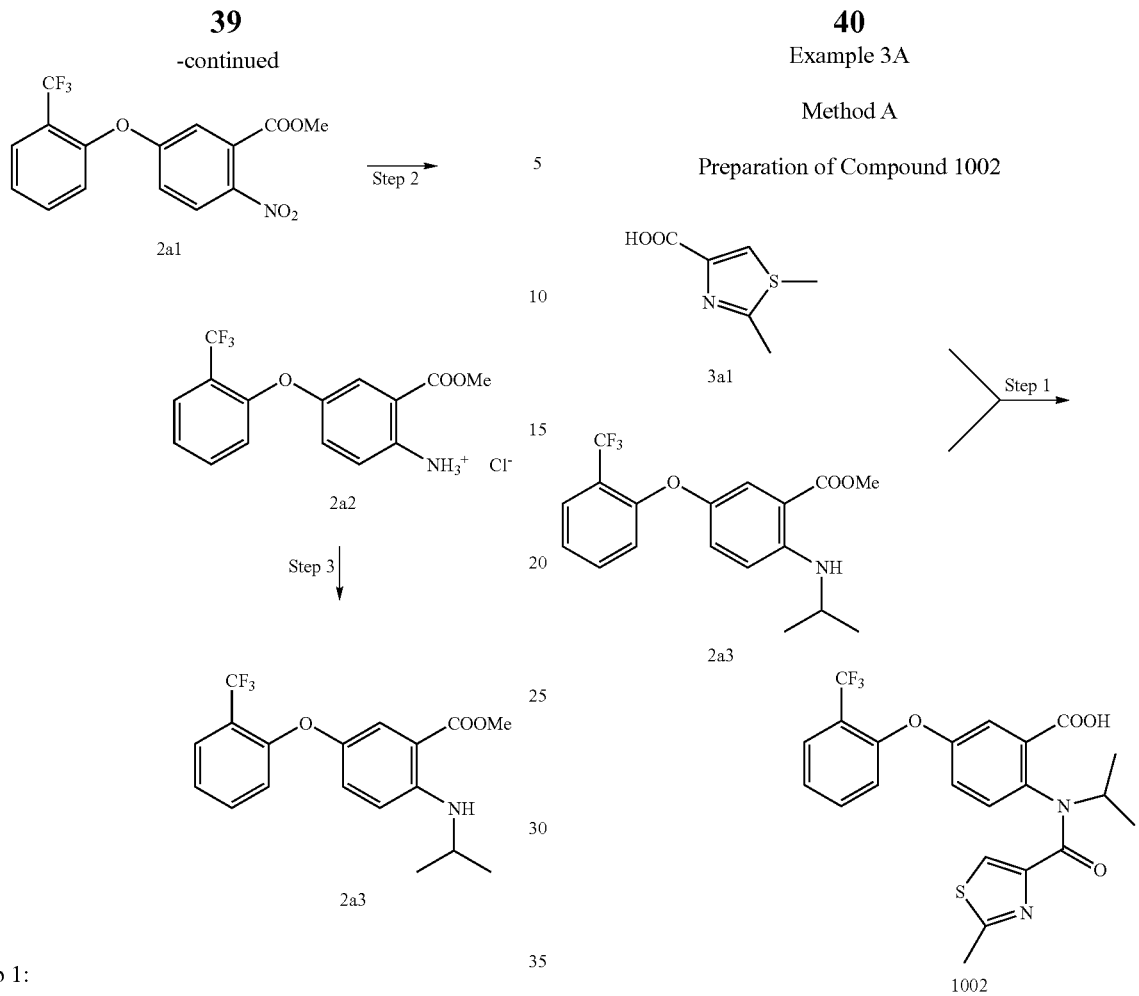

Step 1:

The $S_NAr$ reaction between 2-trifluoromethylphenol and methyl-5-chloro-2-nitrobenzoate 1a1 to form diarylether 2a1 is performed as described in example 1A step 1a.

Step 2:

To a mixture of nitroarene 2a1 (780 mg, 2.3 mmol) in MeOH (20 mL) and AcOH (6 mL) is added iron powder (1.3 g, 23 mmol). The mixture is stirred for 30 minutes at 85° C. before being partitioned between EtOAc and saturated aqueous $NaHCO_3$. The aqueous layer is separated and extracted again with EtOAc. The combined organic extracts are washed with water and brine. The organic phase is dried over $MgSO_4$, filtered, and then concentrated under reduced pressure.

To a mixture of the crude aniline in $Et_2O$ and hexanes is added HCl (1.0 M in ether, 6 mL, 6 mmol). The resulting solid hydrochloride salt 2a2 is collected by filtration and washed with excess ether and dried.

Step 3:

Reductive amination to form i-Pr-aniline 2a3 is performed as described in example 1A step 2.

Example 3A

Method A

Preparation of Compound 1002

Step 1a:

To a mixture of 2-methyl-4-thiazolecarboxylic acid 3a1 (27 mg, 0.17 mmol) and anhydrous DCE (1 mL) is added triphosgene (22 mg, 0.08 mmol) and 2,4,6-collidine (100 µl) and i-Pr-aniline 2a3 (35 mg, 0.10 mmol). The mixture is agitated on a J-Kem® orbital shaker (300 rpm) at 80° C. overnight. The mixture is concentrated under reduced pressure using a Savant™ speed-vac. The residue is taken up in EtOAc and washed with saturated aqueous $NaHCO_3$ (×2) and brine. The solvent is removed under reduced pressure. The residue is taken up in DMSO then aqueous NaOH (10 N, 50 µL, 0.5 mmol) and water (180 µL) are added and the mixture is agitated on a J-Kem® orbital shaker (300 rpm) at RT overnight. The mixture is acidified with AcOH (200 µl) then injected onto a preparative HPLC to isolate compound 1002.

Example 4A

Preparation of Intermediate 4a12

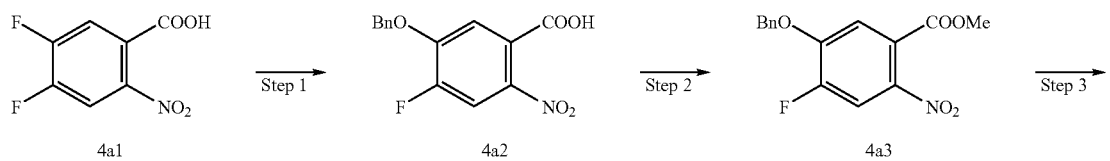

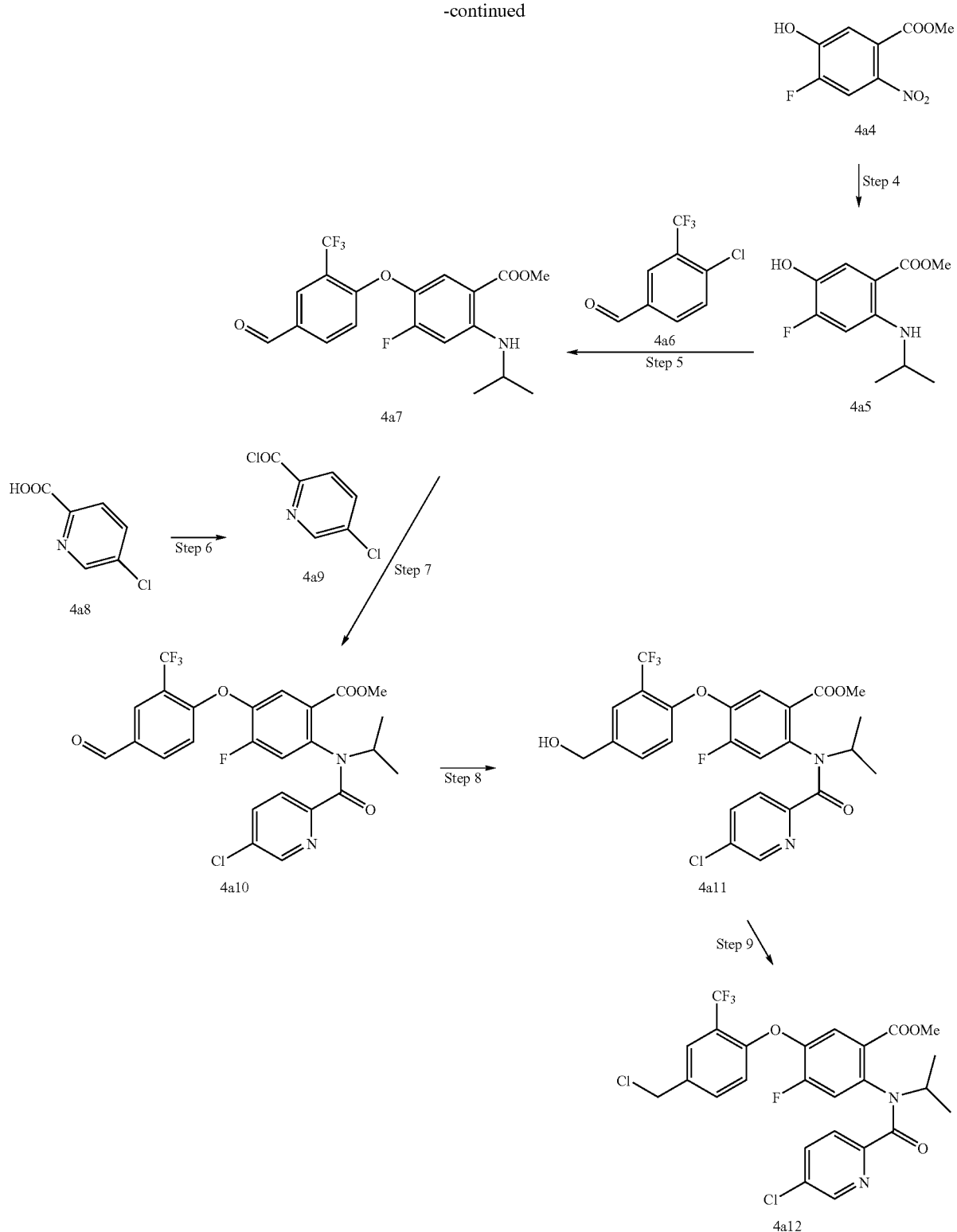

Step 1:

4,5-difluoro-2-nitrobenzoic acid 4a1 (73 g, 359 mmol) is combined with anhydrous THF (2 L) under argon. Benzylalcohol (80.8 mL, 800 mmol) is added and the mixture is chilled to 0° C. Sodiumbis(trimethylsilyl)amide (1.0 M in THF, 800 mL, 800 mmol) is added drop-wise. After stirring for one hour, the mixture is partitioned between saturated aqueous NH₄Cl and EtOAc. The organic phase is collected and dried over sodium sulfate. The mixture is filtered and concentrated. The resulting solid 4a2 is washed with cold EtOAc and dried.

Step 2:

Carboxylic acid 4a2 (112.8 g, 384 mmol) is combined with anhydrous DMF (2 L). Potassium carbonate (108.1 g, 775 mmol) is added and the mixture is chilled to 0° C. Iodomethane (110 g, 775 mmol) is added drop-wise and after 2 hours the reaction is quenched by the addition of saturated aqueous $NH_4Cl$. The aqueous solution is extracted with EtOAc (×2). The combined organic extracts are then washed with water and brine before being dried with $MgSO_4$. Removal of solvent results in methyl ester 4a3.

Step 3:

Benzylether 4a3 (56.7 g, 186 mmol) is combined with MeOH (300 mL) and EtOAc (300 mL) in a Parr Bomb. The solution is degassed with Ar then Pearlman's catalyst (6 g) is added. The bomb is charged with 30 psi of $H_2$ and stirred at RT overnight. The mixture is filtered and the solvent removed in vacuo. The residue is triturated with hexane to afford phenol 4a4.

Step 4:

Reference: Abdel-Magid, A. F.; Carson, K. G.; Harris, B. D.; Maryanoff, C. A.; Shah, R. D. *J. Org. Chem.* 1996, 61, 3849.

To a mixture of phenol 4a4 (5.00 g, 27 mmol) and DCM (200 mL) is added HCl (1.0 M in ether, 27 mL, 27 mmol). After stirring for 5 minutes at ambient temperature, 2-methoxypropene (3.8 mL, 40 mmol) is added followed by NaHB(OAc)$_3$ (11.4 g, 54 mmol). The mixture is stirred for 2 hours. The reaction mixture is diluted in EtOAc and washed with saturated aqueous $NaHCO_3$ and brine. The organic phase is dried with $MgSO_4$ then filtered. Silica gel is added to the solution then the solvent is removed under reduced pressure. The silica gel dry packed compound is purified by combiflash (5 to 30% EtOAc/Hex gradient) to isolate i-Pr-aniline 4a5.

Step 5:

The coupling between i-Pr-aniline 4a5 and chloroarene 4a6 is performed under conditions described in example 1 step 1a. The crude product is purified by flash chromatography to afford diarylether 4a7.

Step 6:

The conversion of acid 4a8 to acid chloride 4a9 is performed using the protocol described in example 1A step 3.

Step 7:

Diarylether 4a7 (4.96 g, 11.7 mmol) is combined with DCM (60 mL) and anhydrous pyridine (5.7 mL, 70.3 mmol). This mixture is transferred via cannula into a mixture of acid chloride 4a9 and DCM (60 mL). Finally, DMAP (0.29 g, 2.3 mmol) is added and the mixture is stirred under reflux for 20 hours. The reaction mixture is washed with water, 0.5 N HCl and brine. The organic phase is dried with $MgSO_4$, and filtered followed by removal of the solvent under reduced pressure. The crude product is purified by flash chromatography to isolate amide 4a10.

Step 8:

To a mixture of amide 4a10 (1.96 g, 3.6 mmol) in MeOH (20 mL) is added $NaBH_4$ (0.27 g, 7.3 mmol). The mixture is stirred at RT under an Ar atmosphere overnight. The mixture is diluted in EtOAc (100 ml) and washed with saturated aqueous $NaHCO_3$ and brine followed by drying over $MgSO_4$. Filtration and concentration affords alcohol 4a11 that is used without purification.

Step 9:

To a mixture of alcohol 4a11 (1.97 g, 3.6 mmol) in anhydrous DCM (50 mL) and anhydrous DMF (1 mL) is added $SOCl_2$ (0.86 g, 7.4 mmol) drop-wise. The mixture is stirred at RT for 1 hour. The mixture is diluted in EtOAc (100 mL) and washed with saturated aqueous $NaHCO_3$ and brine, then dried over $MgSO_4$. After filtration and concentration in vacuo benzylchloride 4a12 is recovered.

Example 5A

Preparation of Intermediate 5a8

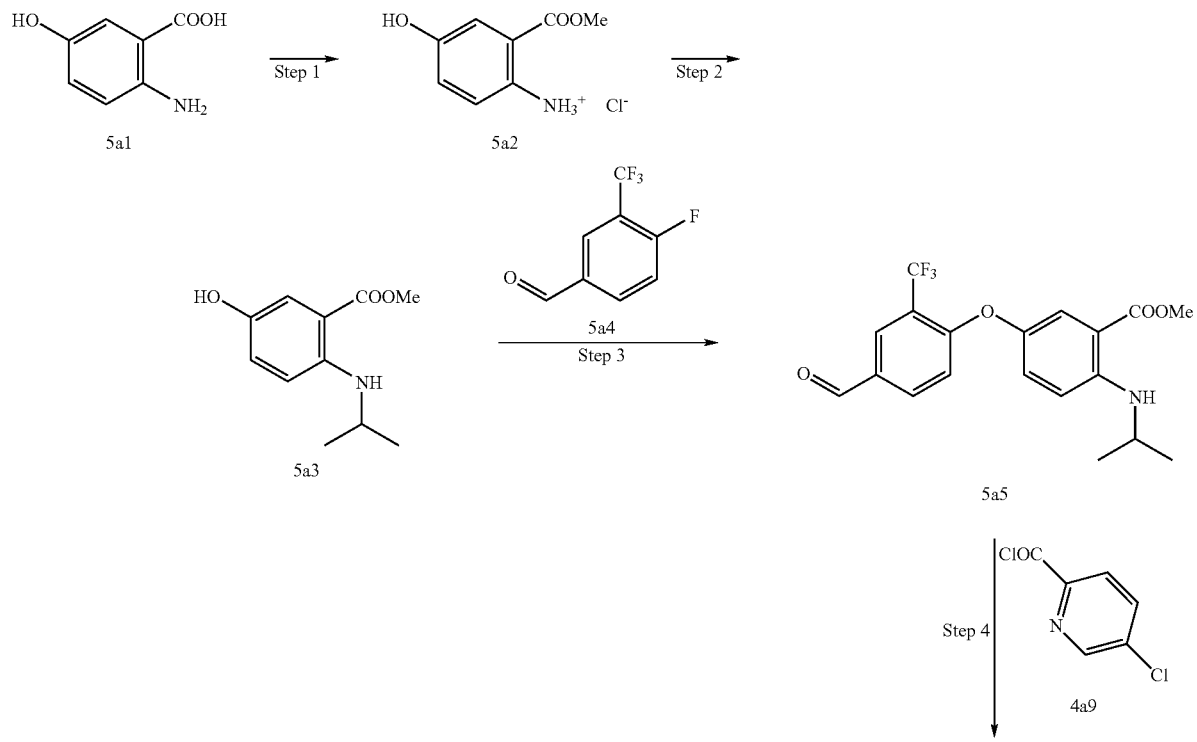

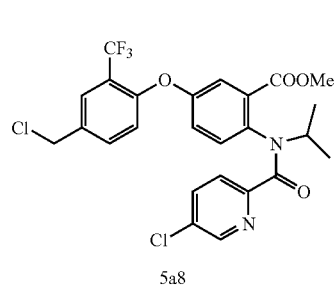
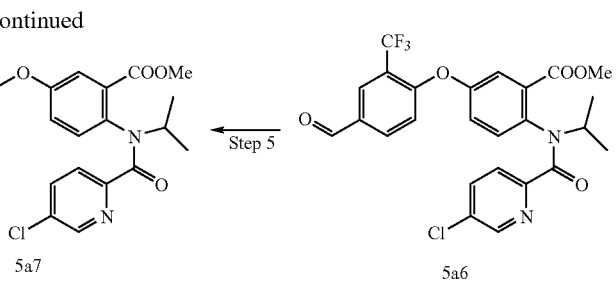

Step 1:

To a mixture of 5-hydroxyanthranilic acid 5a1 (400 g, 2.6 mol) in MeOH (4 is added $SOCl_2$ (380 mL, 5.2 mol). The mixture is heated to reflux and stirs overnight before an additional portion of $SOCl_2$ is added (190 mL). The mixture is refluxed for 3 hours then allowed to cool to RT. The mixture is diluted in MeCN (6 L). The mixture is chilled to 10° C. and stirred for 30 minutes. The resulting solid 5a2 is collected by filtration and washed with MeCN.

Step 2:

Introduction of the i-Pr-group to aniline hydrochloride salt 5a2 to generate 5a3 is performed as described in example 1A step 2.

Step 3:

The coupling between phenol 5a3 and fluoroarene 5a4 is performed under conditions described in example 1A step 1a. The crude product is purified by flash chromatography to afford diarylether 5a5.

Step 4:

The coupling between diarylether 5a5 and acid chloride 4a9 to form amide 5a6 is performed under conditions described in example 4A step 7.

Step 5 & 6:

The conversion of amide 5a6 to alcohol 5a7 then to benzylchloride 5a8 is performed using protocols described in example 4A steps 8 and 9. Final product 5a8 is purified by flash chromatography.

Example 6A

Method B

Preparation of Compound 1016

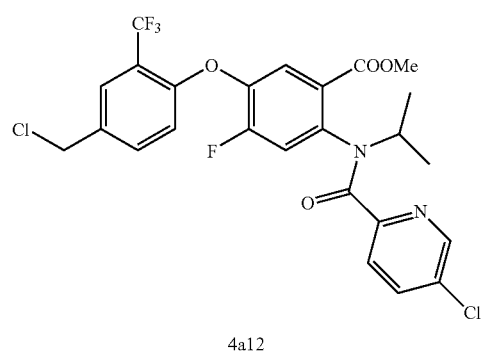

Step 1:

A mixture of benzylchloride 4a12 (56 mg, 0.1 mmol), 2-amino-6-ethylpyridine (18 mg, 0.15 mmol), $Cs_2CO_3$ (50 mg, 0.15 mmol), KI (6 mg, 0.04 mmol) and $MgSO_4$ (70 mg, 0.58 mmol) in DMF (1 mL) is agitated on a J-Kem® orbital shaker (300 rpm) at 70° C. overnight. The mixture is cooled to ambient temperature, filtered and washed with DMSO (0.5 mL). Aqueous NaOH (5 N, 0.2 mL, 1.0 mmol) is added and the mixture is agitated on a Bohdan orbital shaker (300 rpm) at RT for 2 hours. The mixture is acidified with AcOH, then purified by preparative HPLC to isolate compound 1016.

Example 7A

Method C

Preparation of Compound 1008

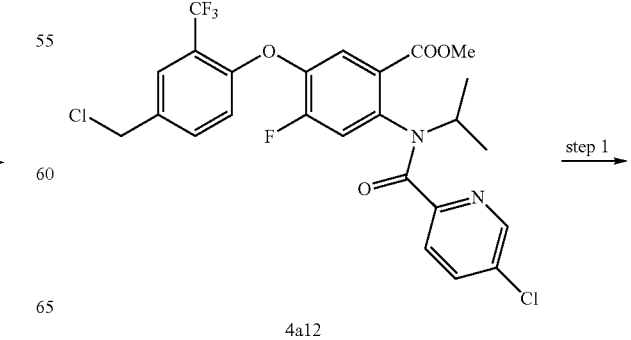

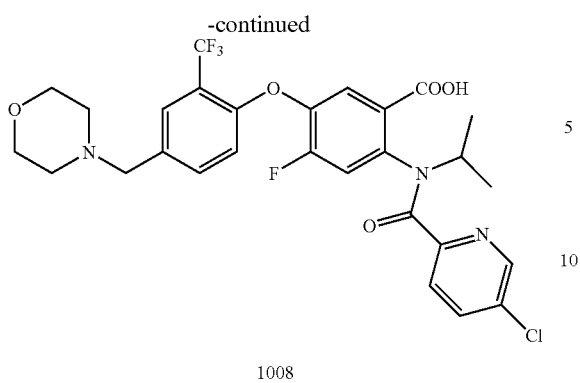

1008

Step 1:
A mixture of intermediate 4a12 (56 mg, 0.1 mmol), morpholine (13 mg, 0.15 mmol) and Et₃N (0.025 mL, 0.18 mmol) in THF (2 mL) is agitated on a J-Kem® orbital shaker (300 rpm) at 70° C. overnight. The mixture is concentrated under reduced pressure using a Savant™ speed-vac and then taken up in DMSO (1 mL). Aqueous NaOH (5 N, 0.2 mL, 1.0 mmol) is added and the mixture is agitated on a Bohdan™ orbital shaker (300 rpm) at RT for 2 hours. The mixture is acidified with AcOH and purified by preparative HPLC to isolate compound 1008.

Example 8A

Preparation of Compound 1036

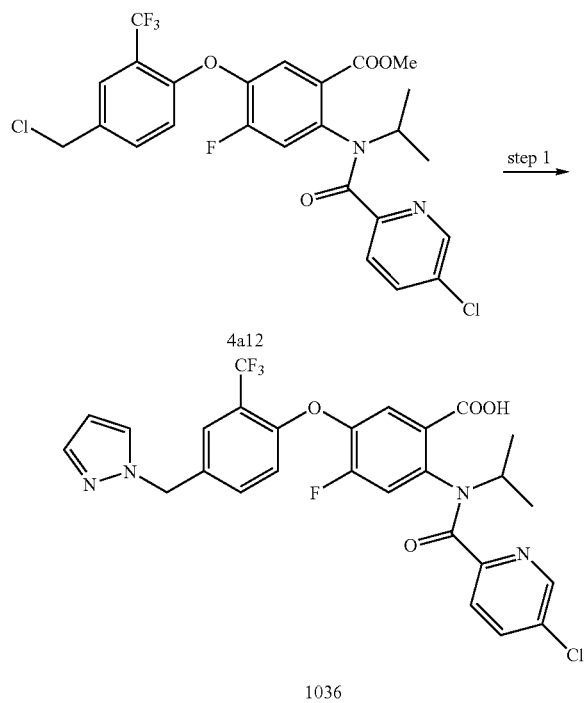

1036

Step 1:
A mixture of benzylchloride 4a12 (40 mg, 0.07 mmol), pyrrazole (5 mg, 0.07 mmol), K₂CO₃ (33 mg, 0.24 mmol), KI (4 mg, 0.02 mmol) in acetone (1 mL) is heated to 70° C. and is stirred for 2 hours. The mixture is concentrated and the residue is taken-up in DMSO (1 mL). Aqueous NaOH (2.5 N, 0.4 mL, 1.0 mmol) is added and the mixture is heated to 50° C. and is stirred for about 1 hour. The mixture is acidified with AcOH, then purified by preparative HPLC to isolate compound 1036.

Example 9A

Method D

Preparation of Compound 1037

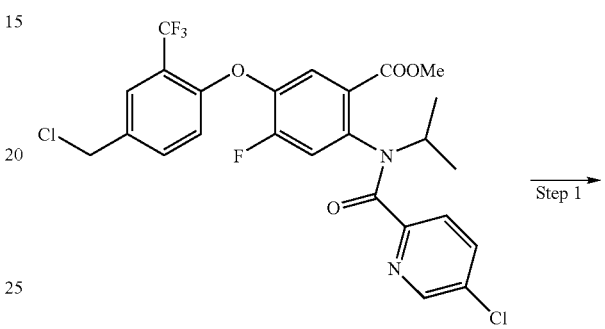

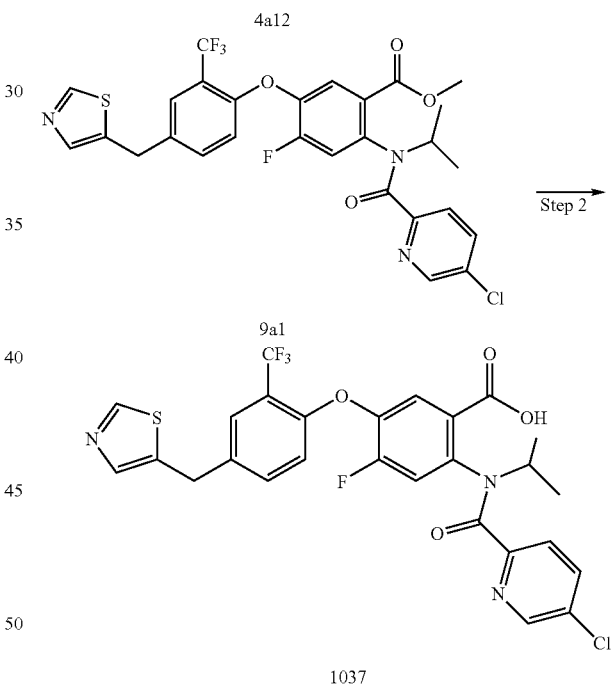

1037

Step 1:
To a degassed (N₂) mixture of benzylchloride 4a12 (84 mg, 0.15 mmol) in anhydrous DMF (2 mL) is added 5-tributylstannylthiazole (126 mg, 0.34 mmol) and (Ph₃P)₄Pd(0) (17 mg, 0.02 mmol). The mixture is heated in a microwave at 120° C. for 20 minutes. The mixture is diluted in EtOAc (50 ml) and washed with water and brine. The organic phase is dried over MgSO₄, filtered and the solvent is removed under reduced pressure. The residue is subjected to flash chromatography (1:1 EtOAc/Hex) to isolate 9a1.

Step 2:
To a mixture of ester 9a1 (57 mg, 0.09 mmol) in DMSO (2 mL) and water (0.1 mL) is added aqueous LiOH (1 N, 100 μl, 0.1 mmol). The mixture is stirred overnight at RT. More LiOH (1 N, 100 μL. 1.0 mmol) is added and stirring is continued for 1 hour. The mixture is acidified with TFA, filtered then injected onto a preparative HPLC to isolate compound 1037.

Example 10A

Preparation of Intermediate 10a6

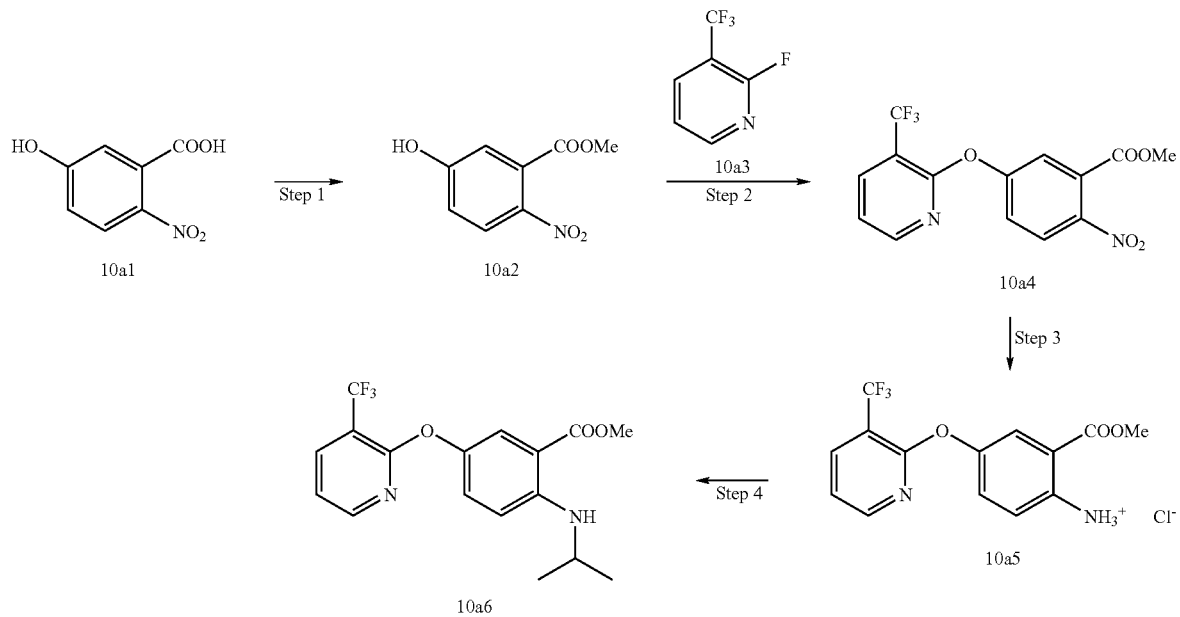

Step 1:

A mixture of carboxylic acid 10a1 (5.0 g, 27 mmol) and concentrated H₂SO₄ (4 mL) in MeOH (80 mL) is stirred at reflux for 12 hours. The mixture is concentrated under reduced pressure and poured onto a mixture of ice and saturated aqueous NaHCO₃. The aqueous mixture is acidified with citric acid and extracted twice with EtOAc. The combined organic extracts are washed with water and brine, dried with MgSO₄, filtered, and concentrated under reduced pressure. Purification by flash chromatography (3:7 EtOAc/Hexane) affords ester 10a2.

Step 2:

Compound 10a2 (10 g, 51 mmol), 2-fluoro-3-trifluoromethylpyridine 10a3 (10 g, 61 mmol) and K₂CO₃ (8.4 g, 61 mmol) are mixed in anhydrous DMSO (150 mL) at room temperature under an argon atmosphere. The mixture is stirred at 100° C. overnight, cooled to room temperature and diluted with EtOAc (3 L). The organic phase is washed with saturated NH₄Cl solution and brine, dried over MgSO₄, filtered and concentrated under reduced pressure. Addition of Et₂O and hexanes to the residue provides compound 10a4; more compound 10a4 is obtained by concentrating the filtrate and purifying the residue by flash chromatography.

Step 3:

A mixture of compound 10a4 (12.5 g, 37 mmol), MeOH (600 mL) and Pd/C (1.4 g) is stirred at room temperature for 3.5 hours under H₂ (1 atm). The mixture is filtered through celite and rinsed with MeOH. The filtrate is concentrated and the residue is purified by flash chromatography (gradient; ¼ to ⅔ EtOAc/Hexanes). A mixture of the free aniline obtained and CH₂Cl₂ (250 mL) is cooled to 0° C. and 2 M HCl in Et₂O (50 mL) is added. The mixture is stirred at room temperature for 1 h and the hydrochloride salt 10a5 is collected by filtration, rinsed with Et₂O and air dried.

Step 4:

To a mixture of compound 10a5 (2.1 g, 5.9 mmol) and 2-methoxypropene (2.3 mL, 24 mmol) in CH₂Cl₂ is added NaBH(OAc)₃ (2.5 g, 12 mmol) portion-wise. The mixture is stirred at RT for 30 minutes, then diluted with EtOAc and washed with saturated aqueous NaHCO₃ and brine. The organic phase is dried with MgSO₄, filtered and concentrated under reduced pressure. Trituration of the residue in hexanes/ether followed by filtration, washing (hexanes) and drying affords compound 10a6.

Example 11A

Method E

Preparation of Compound 2001

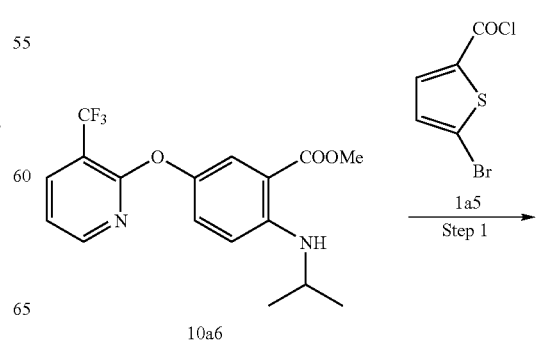

-continued

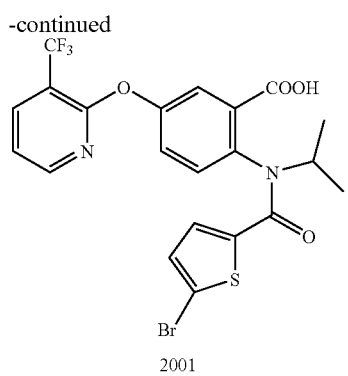

2001

Step 1:

To 5-bromothiophene-2-carbonyl chloride 1a5 (0.080 mmol) in an 8-mL vial is added a pyridine solution (0.5 mL) of the aniline 10a6 (20 mg, 0.056 mmol). The vial is agitated on a J-Kem® orbital shaker (250 rpm) at 80° C. overnight and then concentrated. The residue is taken-up in dry pyridine (0.5 mL) containing DMAP (1.3 mg, 0.011 mmol) and treated again with 5-bromothiophene-2-carbonyl chloride (0.080 mmol). The reaction mixture is stirred overnight at 80° C. A third coupling reaction is performed at 60° C. (0.08 mmol of acid chloride and 0.011 mmol of DMAP) as may be necessary in order to get a complete transformation to the desired amide. After concentration, the crude amide is dissolved in dichloroethane (10 mL) and treated with Wang resin (0.86 g, 0.95 mmol) and MP-carbonate (0.33 g, 0.95 mmol). The reaction mixture is agitated on a J-Kem® orbital shaker (250 rpm) at RT for 1 hr, filtered and concentrated. The residue is then dissolved in DMSO (0.5 mL) and treated with water (50 µL) and a 10 N aqueous NaOH solution (50 µL). The reaction mixture is agitated on a Bohdan™ shaker at 450 rpm overnight at RT. Acetic acid (200 µL) is added and the solution is injected onto a semi-preparative LC-MS (Column: Agilent SB-C18, 5 uM, 21.2 mm×50 mm; gradient: 5%-100% H$_2$O 0.06% TFA/CH$_3$CN 0.06% TFA; 30 ml/min; 13.5 min makeup: 25% H$_2$O 0.05% Ammonium Formate/75% MeCN; 1 ml/min). After lyophilization, 2001 is isolated.

Example 12A

Preparation of Compound 2003

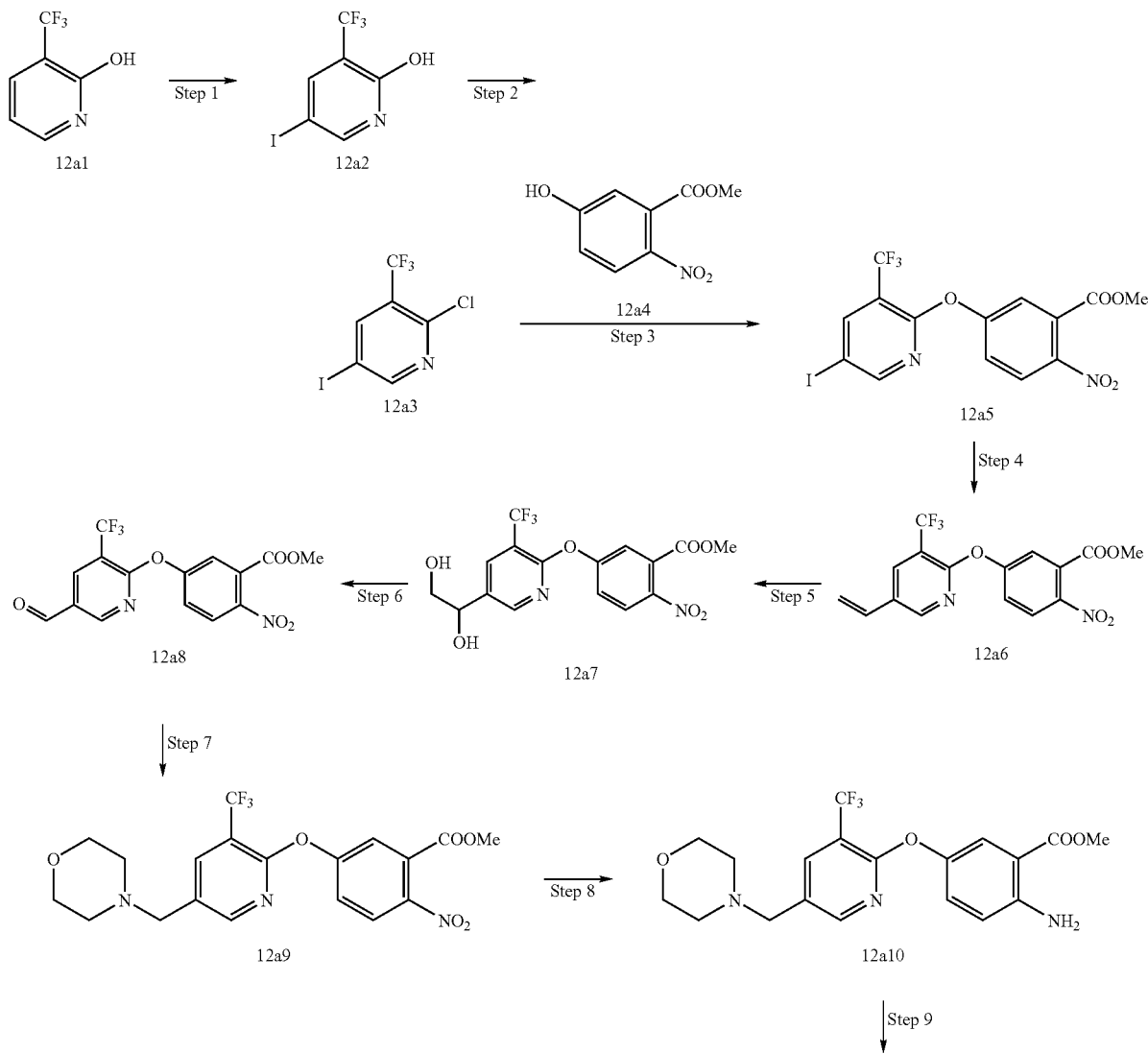

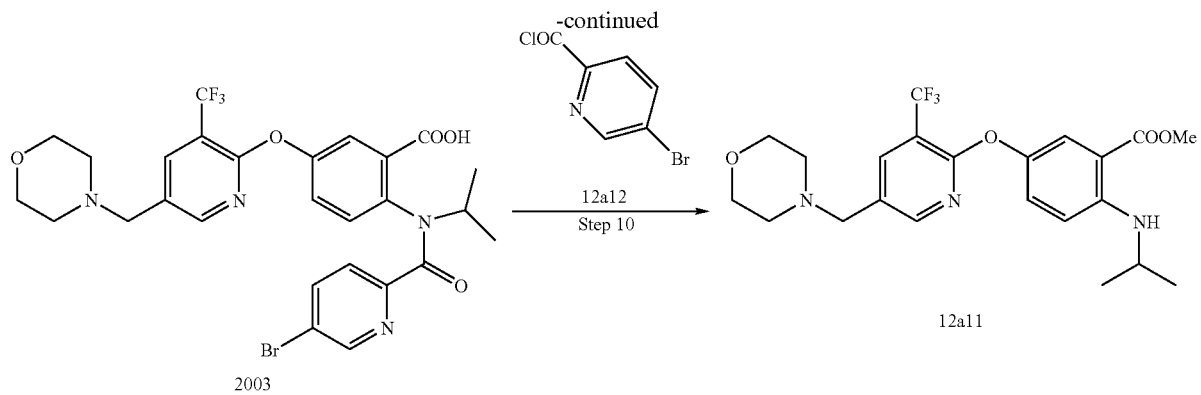

2003

Step 1:
To a mixture of 2-hydroxy-3-trifluoromethylpyridine 12a1 (39.01 g, 239 mmol) and anhydrous DMF (800 mL) under Ar is added N-iodosuccinimide (4.89 g, 244 mmol) and anhydrous K$_2$CO$_3$ (33.72 g, 244 mmol) and the mixture is allowed to stir at 60° C. for about 3 hours. The mixture is cooled to ambient temperature, filtered and concentrated under reduced pressure. The residue is dissolved in DCM (1 L) and the organic phase is washed with brine. The aqueous phase is adjusted to pH 4 by the addition of 2 M HCl then extracted with DCM (1 L). The combined organic extracts are washed with brine (2 L) and dried over Na$_2$SO$_4$. The mixture is concentrated to ~300 mL and cooled overnight in a fridge. The precipitated solid is removed by filtration and dried to provide aryl iodide 12a2.

Step 2:
A mixture of compound 12a2 (115.7 g, 400 mmol) and PhPOCl$_2$ (668.6 g, 343 mmol) under N$_2$ is stirred at 136° C. overnight, then cooled to room temperature and added slowly to 3 L of crushed ice. The aqueous mixture is adjusted to pH 6 and filtered. The aqueous filtrate is extracted with DCM (3 L) then the organic phase is washed with saturated NaHCO$_3$ and brine, dried over Na$_2$SO$_4$, filtered and concentrated to provide chloropyridine 12a3.

Step 3:
The S$_N$Ar reaction between methyl-5-hydroxy-2-nitrobenzoate 12a4 (synthesized from the corresponding benzoic acid using the conditions described example 5 step 1) and chloropyridine 12a3 to form ether 12a5 is performed in the conditions described in example 1A step 1.

Step 4:
To a degassed (Ar) mixture of compound 12a5 (1.05 g, 2.2 mmol) in anhydrous DMSO (25 mL) are added vinyltributyltin (890 µL, 3.0 mmol) and (PPh$_3$)$_4$Pd (254 mg, 0.22 mmol). The mixture is heated to 95° C. for 1.5 hours. The reaction mixture is diluted in Et$_2$O/EtOAc (100 mL/150 mL) and washed with water and brine. The organic phase is dried over MgSO$_4$, filtered and the solvent is removed under reduced pressure. The residue is subjected to flash chromatography (5:1 Hexane/EtOAc) to isolate alkene 12a6.

Step 5:
To a mixture of the alkene 12a6 (800 mg, 2.2 mmol) in acetone (710 mL) are added tert-BuOH (8 mL), water (5 mL), 4-N-methylmorpholineoxide monohydrate (60% solution in water, 565 µL, 3.3 mmol) and OsO$_4$ (2.5 wt % in t-BuOH, 365 µL). The mixture is stirred overnight at ambient temperature, then is concentrated and taken up in EtOAc (100 mL). The organic phase is washed with 1 N HCl, water, saturated aqueous NaHCO$_3$ and brine. The organic phase is dried over MgSO$_4$, filtered and the solvent is removed under reduced pressure. The residue is subjected to flash chromatography (1:2 Hexane/EtOAc) to isolate diol 12a7.

Step 6:
Sodium periodate (460 mg, 2.2 mmol) is added to a mixture of the diol 12a7 (580 g, 1.4 mmol) in THF (10 mL) and water (5 mL). The mixture is stirred at RT overnight.
The mixture is diluted with ether/EtOAc (50 mL/100 mL) then washed with water and brine, dried over MgSO$_4$, filtered and concentrated under reduced pressure. Crude aldehyde 12a8 is utilized in the next step without further purification.

Step 7:
To a mixture of the aldehyde 12a8 (510 mg, 1.4 mmol) in EtOH (6 mL) are added AcOH (87 µL, 1.5 mmol) and morpholine (150 µL, 1.7 mmol). The mixture is warmed to 50° C. and is stirred for about 1 hour. The mixture is allowed to cool to RT and NaCNBH$_3$ (99 mg, 1.6 mmol) is added. The mixture is stirred at RT for about 2 hours. The mixture is diluted with ether/EtOAc (50 mL/100 mL) then washed with saturated aqueous NaHCO$_3$, water and brine. The organic phase is dried over MgSO$_4$, filtered and concentrated under reduced pressure. The residue is subjected to flash chromatography (1:2 Hexane/EtOAc) to isolate 12a9.

Step 8:
Nitroarene 12a9 is reduced to aniline 12a10 using the procedure described in example 2A step 2. (note: HCl salt is not generated)

Step 9:
To a mixture of aniline 12a10 (100 mg, 0.24 mmol) in DCM (5 mL) is added 2-methoxypropene (116 µL, 1.2 mmol) followed by NaHB(OAc)$_3$ (258 mg, 1.2 mmol). The mixture is stirred overnight at RT then diluted in EtOAc and washed with saturated aqueous NaHCO$_3$, water and brine. The organic phase is dried over MgSO$_4$, filtered then concentrated under reduced pressure. Crude isopropylaniline 12a11 is utilized in the next step without further purification.

Step 10:
Acid chloride 12a12 is formed from the corresponding carboxylic acid using the protocol described in example 1A step 3.
To a mixture of i-Pr-aniline 12a11 (50 mg, 0.11 mmol) in anhydrous pyridine (3 mL) is added acid chloride 12a12 (0.55 mmol) and DMAP (13 mg, 0.11 mmol). The mixture is warmed to 80° C. and stirs overnight. The mixture is diluted in EtOAc (50 mL) then washed with 10% citric acid, 1 N NaOH, water and brine. The organic phase is dried over MgSO$_4$, filtered and concentrated under reduced pressure. The residue is taken-up in DMSO (2 mL), MeOH (1 mL) and water (0.2 mL) before aqueous NaOH (10 N, 100 μL, 1.0 mmol) is added. The mixture is stirred for 1 hour at RT before being acidified with TFA, filtered and injected onto a preparative HPLC to isolate compound 2003.

Example 13A

Preparation of Compound 2010

C. once again and MeOH (20 mL) is added carefully. The ice bath is removed and the mixture is heated to 100° C. and stirred for about 4.5 hours. The mixture is carefully diluted into a water/ice mixture. The aqueous mixture is made basic by the addition of NaHCO₃ then is partitioned with EtOAc. The organic layer is separated then washed with water and brine, dried over MgSO₄, filtered and concentrated under reduced pressure. Crude nitro-ester 13a2 is utilized without further purification.

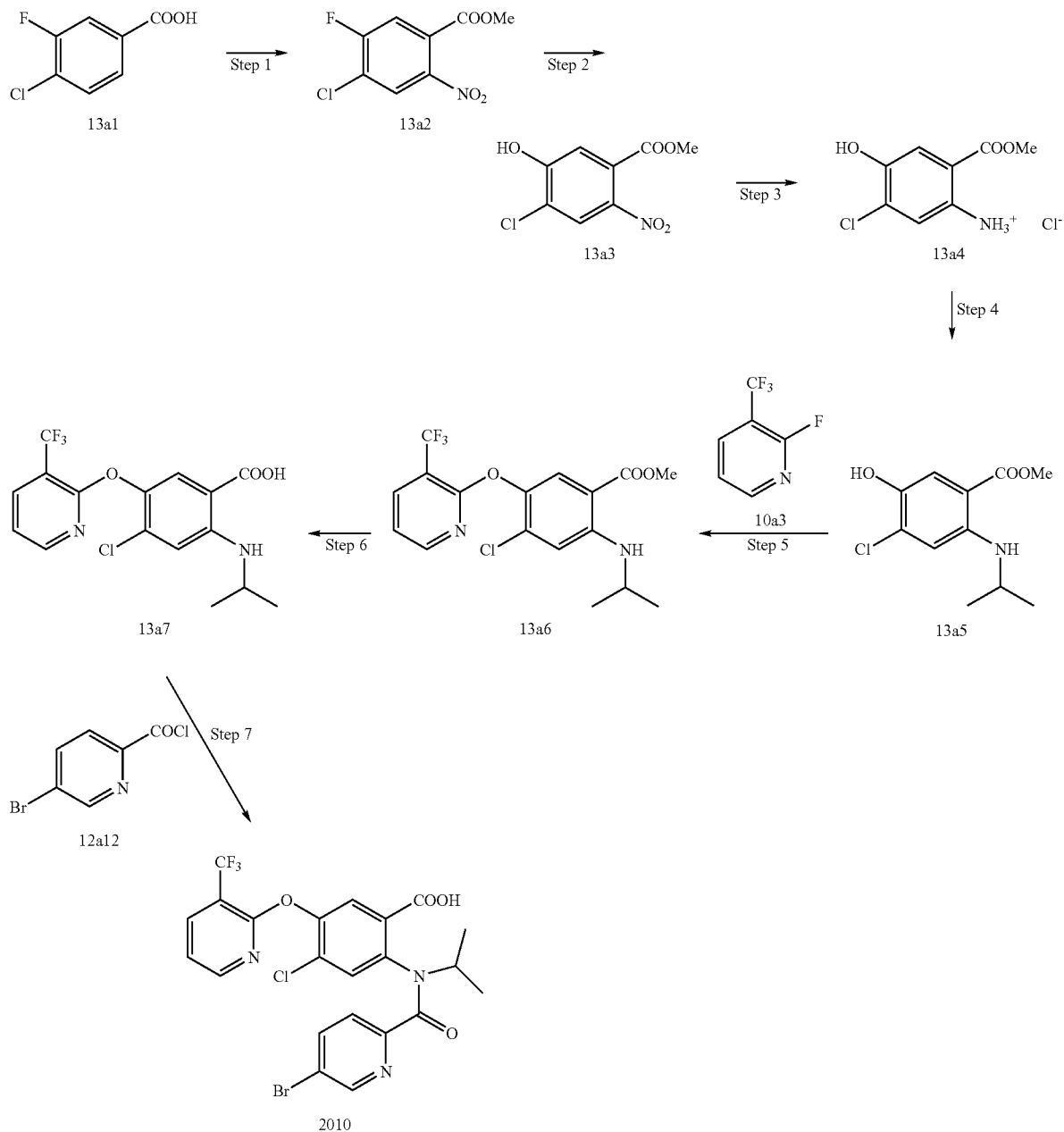

Step 1:

To a mixture of 4-chloro-3-fluorobenzoic acid 13a1 (2.00 g, 11.5 mmol) in concentrated H₂SO₄ (15 mL) chilled to 0° C. is added NaNO₂ (1.16 g, 11.5 mmol) portion-wise. Once the addition of NaNO₂ is complete, the mixture is allowed to warm to RT and stirred overnight. The mixture is chilled to 0°

Step 2:

Reference: Rogers, J. F.; Green D. M. *Tet. Lett.* 2002, 43, 3585.

To a mixture of nitroarene 13a2 (2.57 g, 11.0 mmol) and 2-(methylsulfonyl)ethanol (1.82 g, 14.6 mmol) in anhydrous DMF (30 mL) under a N₂ atmosphere chilled to 0° C. is added NaH (95%, 556 mg, 22.0 mmol). The mixture is stirred at 0° C. for about 1 hour then stirred for 1 hour at RT. The reaction is quenched by the addition of 1 N aqueous HCl then partitioned with EtOAc. The organic phase is separated and washed with water. The organic phase is washed with 1 N NaOH (×2). The combined aqueous washes are acidified with 1 N HCl then extracted with EtOAc (× 2). The combined organic extracts are dried over MgSO$_4$, filtered and concentrated under reduced pressure. Crude phenol 13a3 is utilized without further purification.

Step 3:

To a mixture of nitroarene 13a3 (1.52 g, 6.6 mmol) in MeOH (15 mL) is added SnCl$_2$ (6.5 g, 33 mmol). The mixture is heated to reflux and stirs for 30 minutes. The mixture is allowed to cool to RT then washed partitioned between EtOAc and saturated aqueous NaHCO$_3$. To the mixture is added celite (25 g) then the mixture is filtered. The organic phase is separated and washed with water and brine, dried over MgSO$_4$, filtered and concentrated under reduced pressure. The residue is taken up in EtOAc then treated with HCl (1.0 N in ether, 8 mL, 8.0 mmol). Solid aniline HCl salt 13a4 is recovered by filtration.

Step 4:

Introduction of the i-Pr-group to aniline hydrochloride salt 13a4 to generate 13a5 is performed as described in example 1A step 2.

Step 5:

The S$_N$Ar reaction between phenol 13a5 and fluoropyridine 10a3 to form ether 13a6 is performed under the conditions described in example 1A step 1.

Step 6:

To a mixture of ester 13a6 (70 mg, 0.18 mmol) in THF (4 mL), MeOH (1 mL) and water (75 µL) is added NaOH (10 N, 90 µL, 0.90 mmol) and the mixture is stirred at RT overnight. The reaction is quenched by the addition of 0.5 N aqueous KHSO$_4$ then partitioned with EtOAc. The organic phase is separated and washed with water and brine. The organic phase is dried over MgSO$_4$, filtered and concentrated under reduced pressure. Crude anthranilic acid 13a7 is utilized without further purification.

Step 7:

To a mixture of anthranilic acid 13a7 (53 mg, 0.14 mmol) in anhydrous DCE (2 mL) is added acid chloride 12a12 (44 mg, 0.27 mmol) and anhydrous pyridine (33 µL, 0.41 mmol). The mixture is heated in a microwave oven at 150° C. for 15 minutes. The mixture is diluted in DMSO (1 mL) and acidified with TFA before being partially concentrated and injected onto a preparative HPLC to isolate compound 2010.

Example 14A

Preparation of Intermediate 14a4

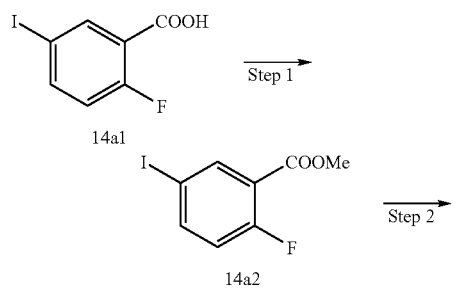

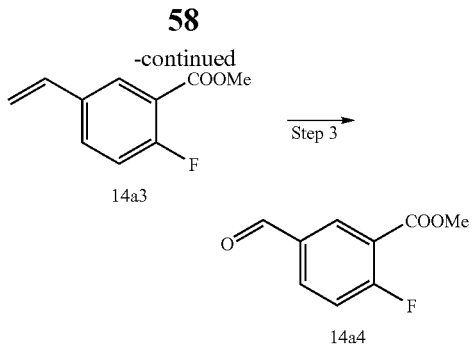

Step 1:

To a stirring mixture of 2-fluoro-5-iodobenzoic acid 14a1 (25 g, 24 mmol) in MeCN (500 mL) and DMF (50 mL) chilled to −5° C. is added DBU (15.4 mL, 103 mmol) followed by the slow addition of MeI (8.8 mL, 141 mmol). The mixture is allowed to warm to RT and stirs overnight. The mixture is poured in water (1 L) then extracted with EtOAc (500 mL×3). The combined organic extracts are washed with brine, dried over Na$_2$SO$_4$, filtered and concentrated under reduced pressure. Crude ester 14a2 is utilized without further purification.

Step 2:

To a mixture of iodoarene 14a2 (22.3 g, 79 mmol) in dioxane (200 mL) is added tributylvinyltin (20 mL, 68 mmol). The mixture is degassed (Ar) before (Ph$_3$P)$_4$Pd (2.4 g, 2.1 mmol) is added. The mixture is refluxed for about 1 hour then stirred at RT overnight. The mixture is concentrated under reduced pressure and the resulting residue is subjected to flash chromatography to isolate alkene 14a3.

Step 3:

To a mixture of alkene 14a3 (9.6 g, 89 mmol) in THF (360 mL) and water (270 mL) is added OsO$_4$ (2.5% solution in t-BuOH, 5.4 mL) followed by the portion-wise addition of NaIO$_4$ (34 g, 160 mmol). The mixture is stirred for about 2 hours at RT before being partially concentrated and diluted in EtOAc. The organic phase is washed with brine, dried over Na$_2$SO$_4$, filtered and concentrated. The residue is subjected to flash chromatography to isolate aldehyde 14a4.

Example 15A

Method F

Preparation of Compound 2011

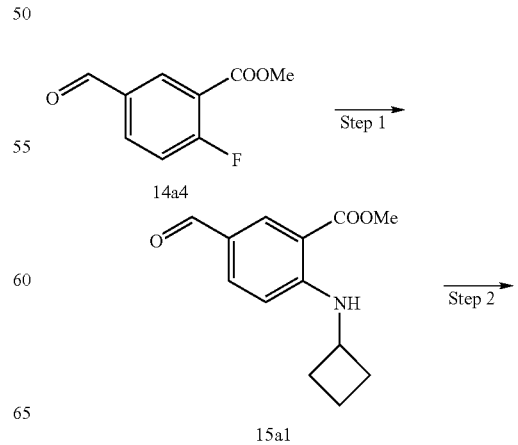

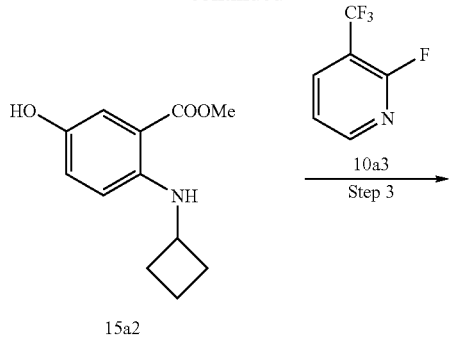

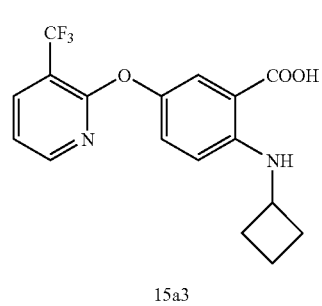

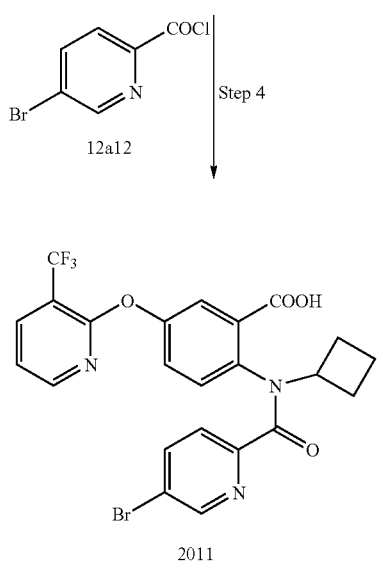

Step 1:

To an 8-mL vial are successively added K₂CO₃ (46 mg, 0.33 mmol), aldehyde 14a4 (50 mg, 0275 mmol in 0.5 mL DMSO) and cyclobutylamine (98 mg, 1.4 mmol). The mixture is agitated on a J-Kem® orbital shaker (270 rpm) at 70° C. overnight. Water (1 mL) and concentrated HCl (0.7 mL) are added to the mixture. The mixture is heated at 70° C. for 3 hrs, extracted with EtOAc (2 mL) and washed three times with water. After concentration the crude aniline 15a1 is obtained and used as such in the following transformation.

Step 2:

To the crude amine 15a1 obtained above in methanol (1.5 mL in an 8-mL vial) at 2° C. are successively added hydrogen peroxide (434 of a 30% aqueous solution) and concentrated H₂SO₄ (20 μL). The mixture is agitated on a J-Kem® orbital shaker (290 rpm) at 2° C. for 15 minutes and then a saturated aqueous solution of NaCl is added (2 mL). The mixture is extracted twice with EtOAc (2 mL and 1 mL) and the combined organic extracts are successively washed with water (1 mL) and brine (1 mL). The organic phase is dried with MgSO₄, filtered and concentrated to afford the crude phenol 15a2 which is used as such in the following transformation.

Step 3:

To the crude phenol 15a2 obtained above in dry DMSO (0.5 mL) are successively added K₂CO₃ (133 mg, 0.96 mmol) and 2-fluoro-3-trifluoromethylpyridine 10a3 (40 pt, 0.33 mmol). The suspension is agitated overnight on a J-Kem® orbital shaker (290 rpm) at 85° C. Aqueous sodium hydroxide solution (5 N, 250 μL) is added at RT and the reaction mixture is agitated at 50° C. for 3 hours. After acidification using a 1 N aq. KHSO₄ solution, the mixture is extracted three times with EtOAc. The combined organic extracts are successively washed with water and brine, dried over MgSO₄ and filtered. After concentration, the residue is dissolved in a mixture of DMSO and AcOH (1.5 mL) and purified by reverse phase preparative LC-MS. Conditions; column: Agilent SB-C18, 5 uM, 21.2 mm×50 mm; gradient: 5% to 100% H₂O 0.06% TFA/CH₃CN 0.06% TFA; flow: 30 ml/min for 13.5 min; makeup: 25% H₂O 0.05% Ammonium formate 175% MeCN; 1 ml/min. After lyophilization the desired compound 15a3 is isolated.

Step 4:

To a mixture of aniline 15a3 (11.1 mg, 0.032 mmol) in DCE (0.3 mL) is added acid chloride 12a12 (7.1 mg, 0.044 mmol) and pyridine (11.0 μL, 0.136 mmol). The mixture is heated at 150° C. for 15 minutes in a microwave. After concentration, the residue is dissolved in DMSO and AcOH, and purified by reverse phase preparative LC-MS. Conditions; column: Agilent SB-C18, 5 uM, 21.2 mm×50 mm; gradiant: 5% to 100% H₂O 0.06% TFA/CH₃CN 0.06% TFA; flow: 30 ml/min for 13.5 min; makeup: 25% H₂O 0.05% Ammonium formate/75% MeCN; 1 ml/min. After lyophilization compound 2011 is isolated.

Example 16A

Preparation of Compound 2027

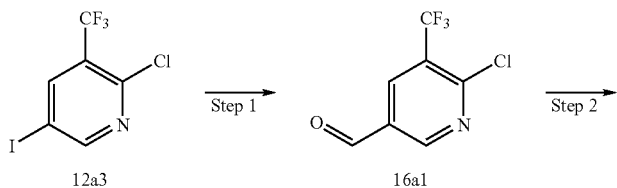

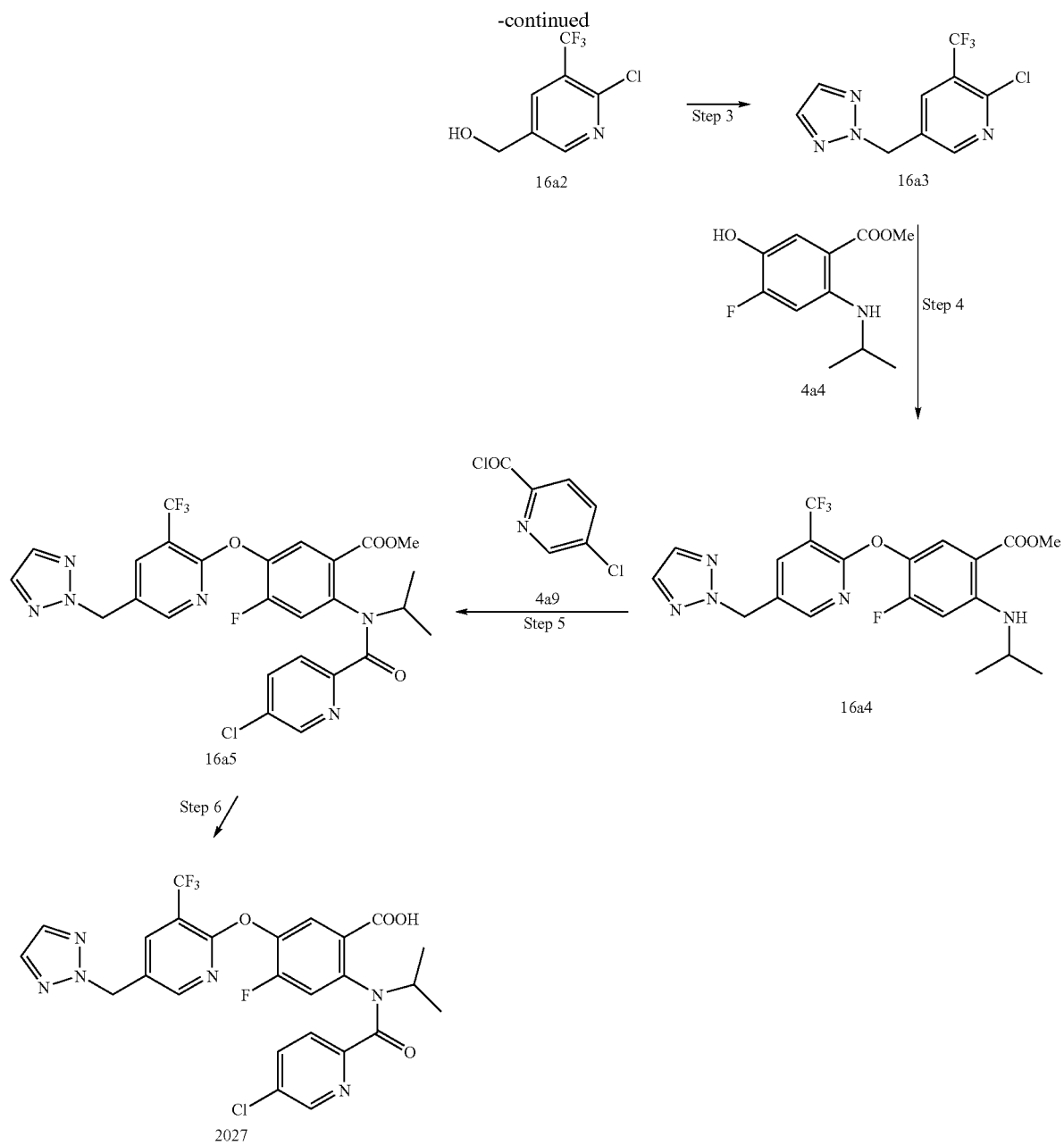

Step 1:
Iodide 12a3 (10 g, 32.5 mmol) is combined with a 1:3 mixture of anhydrous THF and anhydrous toluene (100 mL) under an argon atmosphere. The mixture is cooled to −78° C. then n-BuLi (1.6 M in hexanes, 24 mL, 38.4 mmol) is added slowly by syringe over about 40 minutes. Stirring is continued for about 1 hour before ethylformate (3.2 mL, 39.7 mmol) in THF (10 mL) is added over a period of about 40 minutes. The mixture is stirred for about 1 hour before being quenched by the addition of 2 M HCl. The mixture is partitioned between EtOAc and saturated aqueous NaHCO$_3$. The organic phase is washed with brined and dried over Na$_2$SO$_4$. The mixture is filtered and concentrated under reduced pressure. Purification is performed by flash chromatography where the silica gel is pre-treated with 3% NEt$_3$ in hexanes then eluted with 1:1 EtOAc/Hex to isolate aldehyde 16a1.

Step 2:
A mixture of aldehyde 16a1 (19 g, 81 mmol) in methanol (225 mL) is chilled to 0° C. Sodium borohydride (4.1 g, 109 mmol) is added portion-wise and the mixture is stirred at 0° C. for about 1.5 hours. Another portion of NaBH$_4$ (1 g) is added and the mixture is stirred for another 30 minutes. The reaction is quenched by the addition of NaHSO$_4$ (5% aqueous) then diluted in EtOAc (500 mL). The organic phase is separated then washed with water (500 mL) and brine. The organic phase is dried over Na$_2$SO$_4$, filtered then concentrated under reduced pressure. The residue is subjected to flash chromatography (1:1 EtOAc/Hex) to isolate alcohol 16a2.

Step 3:
Alcohol 16a2 (10.5 g, 48 mmol) is combined with triazole (3.42 g, 48 mmol) and triphenylphosphine (14.3 g, 54 mmol) in anhydrous THF (500 mL). The mixture is chilled to 0° C. and DIAD (10.6 mL, 54 mmol) is added drop-wise. Stirring continues at 0° C. for about 1 hour before the mixture is allowed to warm to ambient temperature and is then stirred overnight. The mixture is diluted in EtOAc and washed with water (500 mL) and brine (500 mL) before being dried over $Na_2SO_4$. The solvents are removed under reduced pressure and the residue is subject to flash chromatography (1:3 EtOAc/Hex) to afford benzylic triazole 16a3.

Step 4:
Phenol 4a4 is coupled to chloropyridine 16a3 using reaction conditions described in example 1A step 1a.

Step 5:
To a mixture of aniline 16a4 (445 mg, 0.98 mmol) in anhydrous DCE (10 mL) is added acid chloride 4a9 (249 mg, 1.4 mmol) and anhydrous pyridine (325 µL, 4.0 mmol). The mixture is heated in a microwave oven at 100° C. for about 10 minutes twice. The mixture is diluted in EtOAc and washed with saturated aqueous $NaHCO_3$ (×2) and brine. The organic phase is dried over $MgSO_4$, filtered and concentrated under reduced pressure. The residue is subject to flash chromatography (2:3 EtOAc/Hex) to isolate amide 16a5.

Step 6:
To a mixture of ester 16a5 (385 mg, 0.65 mmol) in DMSO (6 mL) is added aqueous NaOH (2.5 N, 1.8 mL, 4.5 mmol). The mixture stirs at RT for about 1 hour. The mixture is diluted in water then treated with AcOH. The resulting solid is recovered by filtration then taken up in MeCN and water, frozen and lyophilized to provide compound 2027.

Example 17A

Method G

Preparation of Intermediate 17a4

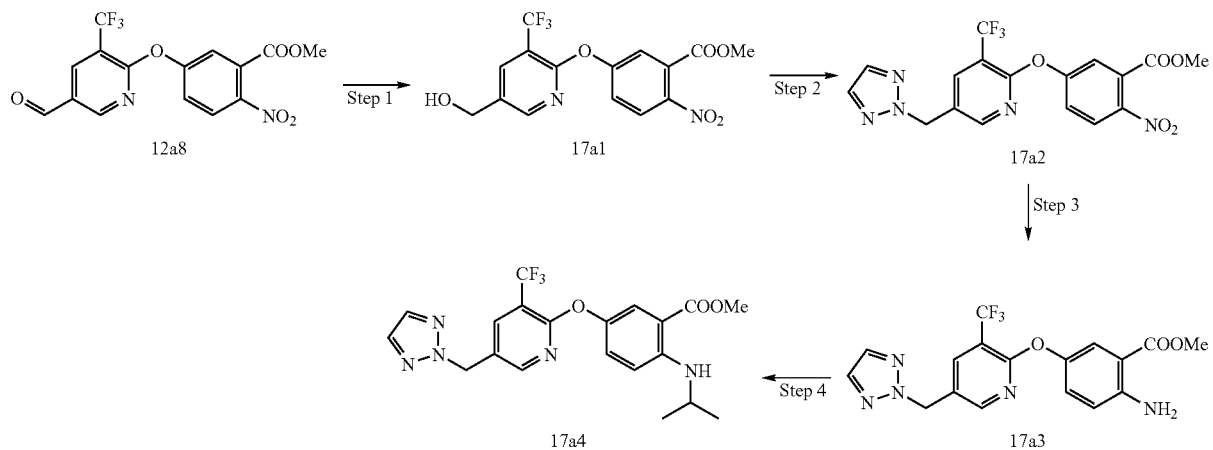

Step 1:
The conversion of aldehyde 12a8 to alcohol Va1 is performed using protocol described in example 4A step 8.

Step 2:
Triazole 17a2 is prepared from alcohol 17a1 using protocol described in example 16A step 3.

Step 3:
Nitroarene 17a2 (503 mg, 1.2 mmol) is dissolved in EtOAc (10 mL) under a stream of nitrogen. Pd/C (100 mg) is added and the degassing is continued for about 2 minutes. Hydrogen is then bubbled through the mixture for about 5 minutes and then the mixture is stirred under hydrogen (1 atm) overnight at RT. The mixture is filtered through celite. The filtrate is concentrated and the residue is purified by combiflash (20% EtOAc/Hex to ETOAc) to yield aniline 17a3.

Step 4:
Introduction of the i-Pr-group to aniline 17a3 to generate 17a4 is performed as described in example 4A step 4.

Example 18A

Method G

Preparation of Compound 2028

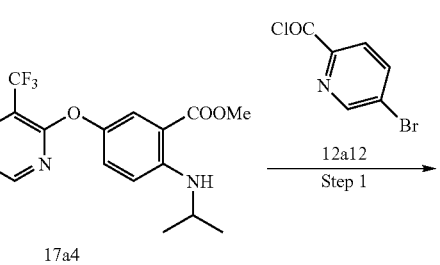

-continued

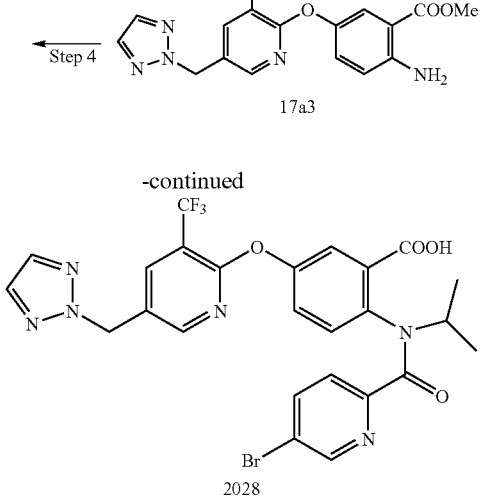

Step 1:

To a mixture of aniline 17a4 (33 mg, 0.07 mmol) in anhydrous DCE (1 mL) is added acid chloride 12a12 (85 mg, 0.39 mmol), DMAP (14 mg, 0.11 mmol) and anhydrous pyridine (30 μL, 0.37 mmol). The mixture is heated in a microwave oven at 150° C. for 15 minutes. The mixture is diluted in EtOAc and washed with saturated aqueous NaHCO₃ (×3) and brine. The organic phase is dried over MgSO₄, filtered and concentrated. The residue is taken-up in THF (1 mL) and MeOH (0.5 mL) and NaOH (10 N, 100 μL, 1.0 mmol) is added and the mixture stirs overnight at RT. The mixture is acidified with TFA before being filtered and injected onto a preparative HPLC to isolate compound 2028.

Example 19A

Preparation of Compound 2030

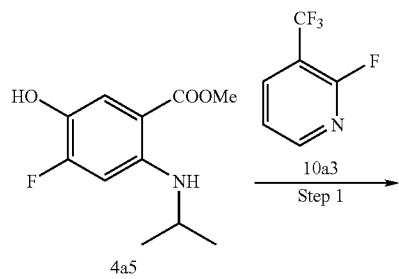

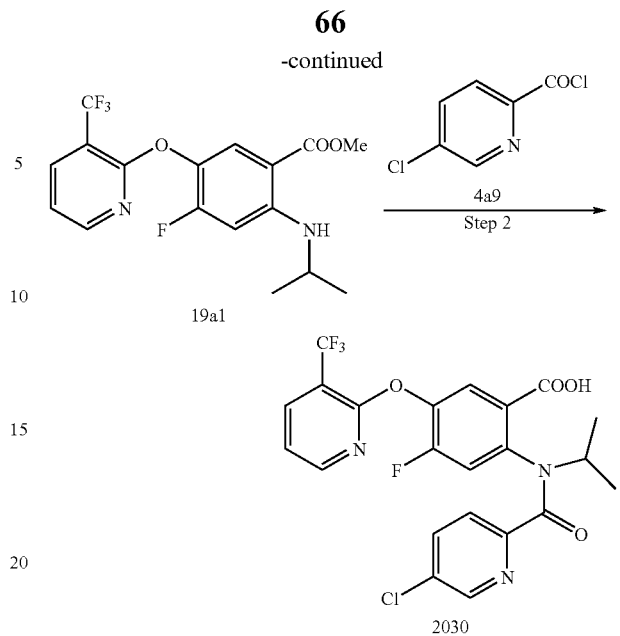

Step 1:
The coupling between phenol 4a5 and fluoropyridine 10a3 is performed under conditions described in example 1 step 1a. The crude product is purified by flash chromatography (1:9 EtOAc/Hex) to afford ether 19a1.

Step 2:
Coupling of aniline 19a1 to acid chloride 4a9, followed by saponification to form compound 2030 is performed as described in example 16A steps 5 & 6.

Example 20A

Preparation of Intermediate 20a4

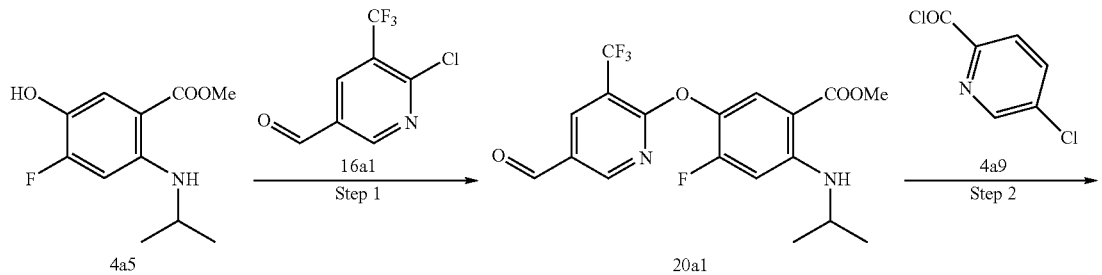

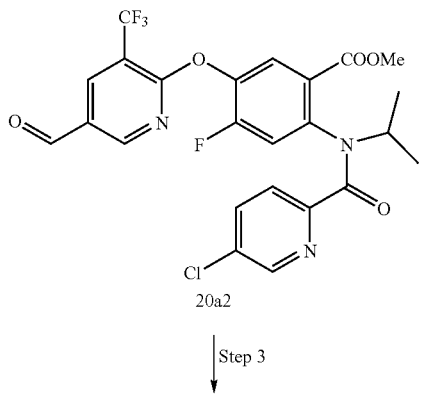

Step 3

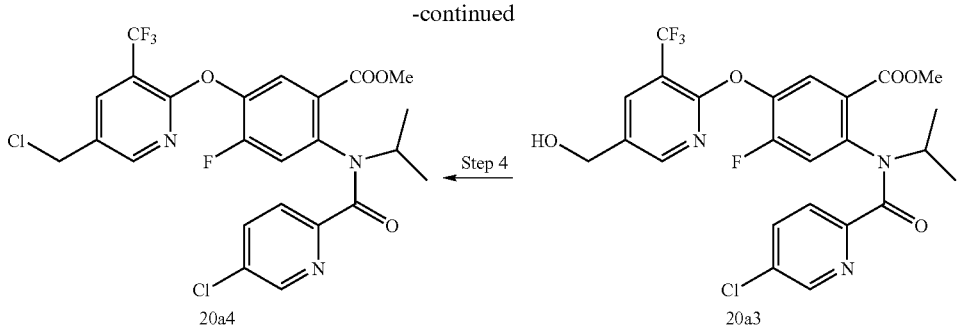

Steps 14:

The sequence demonstrated in example 4A steps 5 to 9 is used to provide intermediate 20a4.

Example 21A

Preparation of Compound 2031

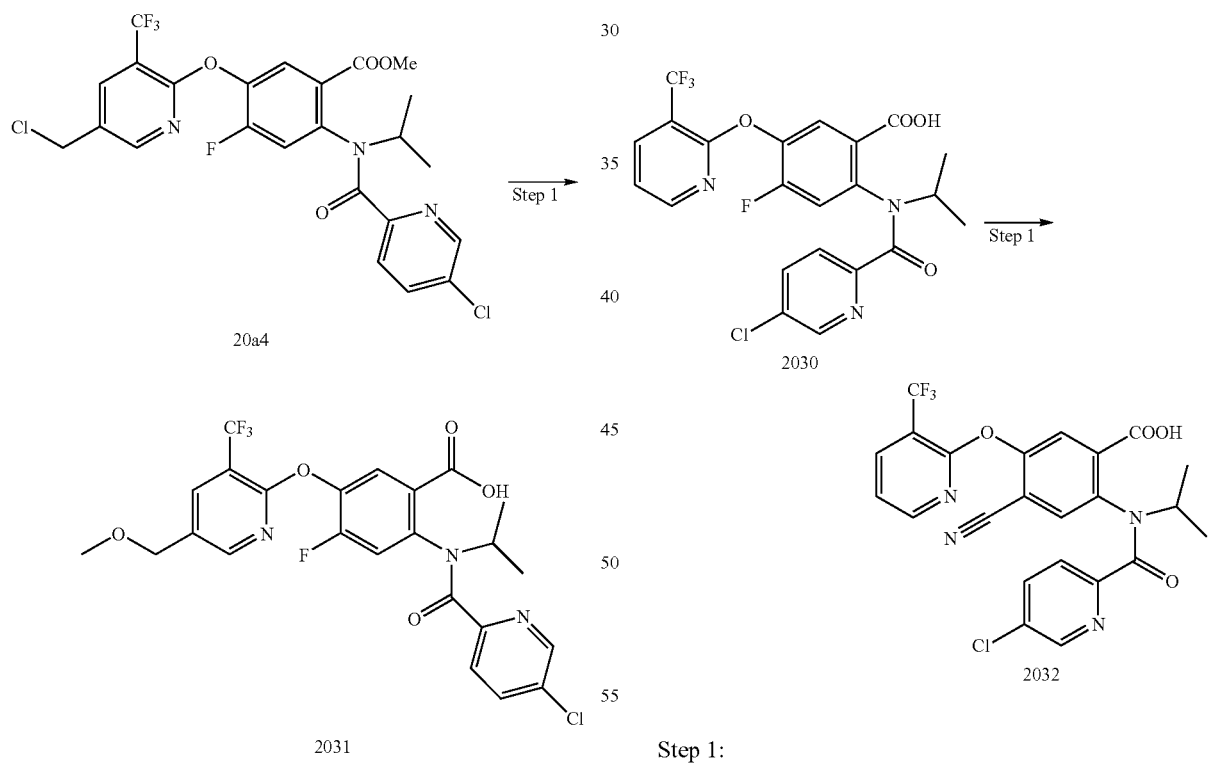

Step 1:

Sodium methoxide (25% in MeOH, 17 µL, 0.08 mmol) is added to a mixture of benzyl chloride 20a4 (40 mg, 0.07 mmol) in MeOH (5 mL) then stirred at ambient temperature for about 16 hours. DMSO (1 mL) is added, followed by NaOH (2.5 N, 240 µL, 0.6 mmol) and the mixture is stirred for about 1 hour at ambient temperature. The mixture is acidified with AcOH, concentrated to 2 mL under reduced pressure, and injected into a preparative HPLC to isolated compound 2031.

Example 22A

Method H

Preparation of Compound 2032

Step 1:

To a mixture of compound 2030 (106 mg, 0.21 mmol) in DCM (5 mL) is added $CH_2N_2$ (solution in ether) until the characteristic yellow colour persists. The mixture is concentrated and the residue is taken-up in DMSO (1 mL) then NaCN (78 mg, 1.2 mmol) is added. The mixture is heated to 150° C. for 20 minutes in a microwave oven until saponification of the ester is observed. The mixture is then injected onto the preparative HPLC to isolate 2032.

Example 23A

Preparation of Intermediate 23a4

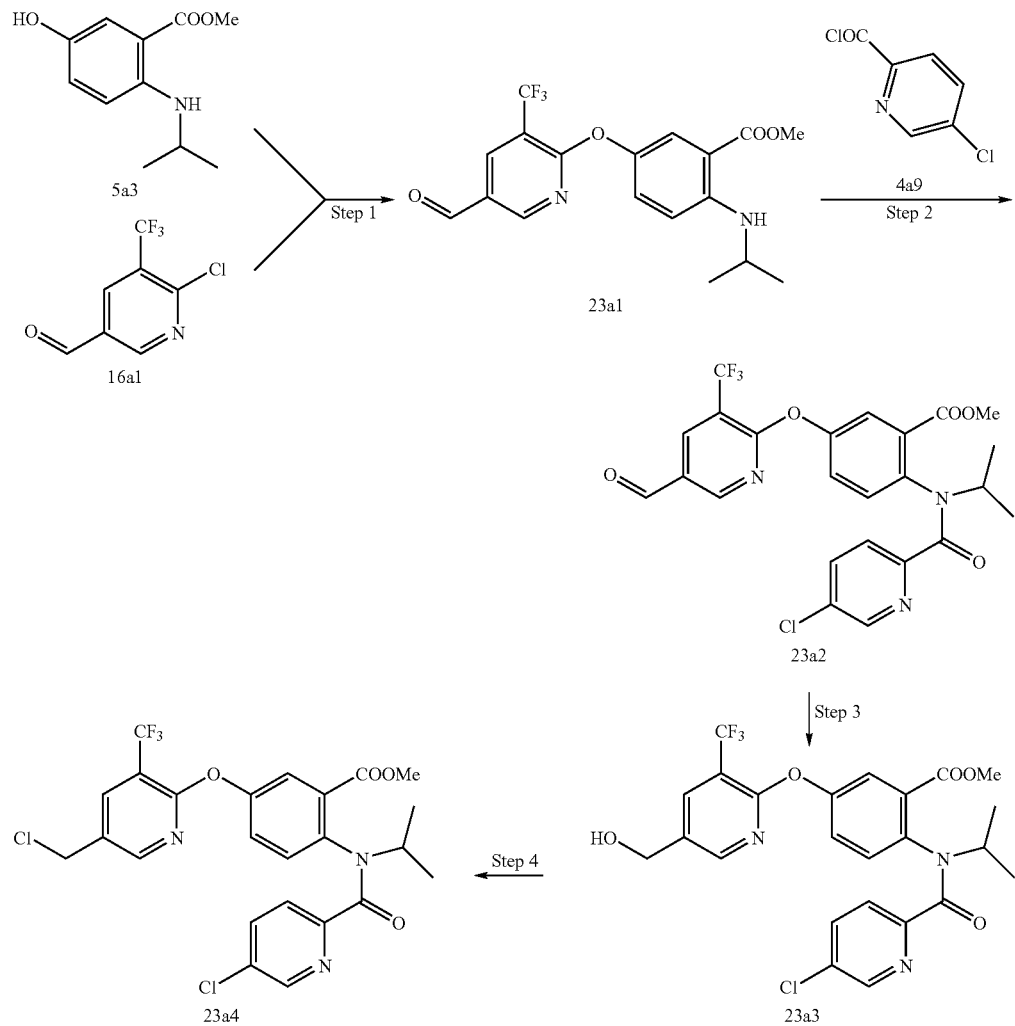

Steps 1-4:
The sequence demonstrated in example 4A steps 5 to 9 is used to provide intermediate 23a4.

Example 24A

Method F

Preparation of Compound 2033

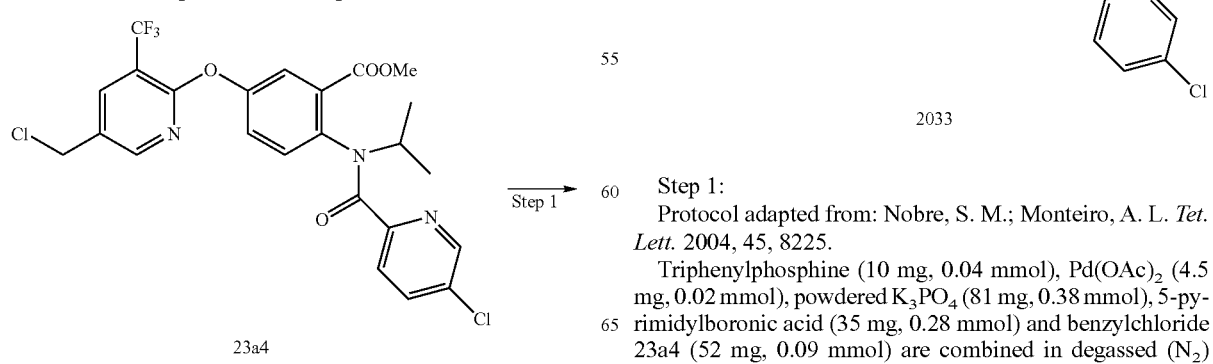

Step 1:
Protocol adapted from: Nobre, S. M.; Monteiro, A. L. *Tet. Lett.* 2004, 45, 8225.

Triphenylphosphine (10 mg, 0.04 mmol), Pd(OAc)$_2$ (4.5 mg, 0.02 mmol), powdered K$_3$PO$_4$ (81 mg, 0.38 mmol), 5-pyrimidylboronic acid (35 mg, 0.28 mmol) and benzylchloride 23a4 (52 mg, 0.09 mmol) are combined in degassed (N$_2$) DMF (2.5 mL). The mixture is heated with stirring at 120° C.

for 20 minutes in a microwave oven. The mixture is diluted in DMSO (2 mL)/MeOH (1 mL)/water (0.3 mL) then NaOH (10 N, 350 μL, 3.5 mmol) is added. The mixture is stirred for about 1.5 hours at RT. The mixture is acidified with TFA, partially concentrated, filtered then injected onto a preparative HPLC to isolate compound 2033.

Example 25A

Preparation of Compound 2066 extracts are dried over MgSO$_4$, filtered and concentrated. The residue is subjected to flash chromatography to provide cyclobutylaniline 25a2.

Step 3:

To a mixture of benzylether 25a2 (265 mg, 0.8 mmol) in EtOH (5 mL) and EtOAc (2 mL) under a N$_2$ atmosphere is added 10% Pd/C (20 mg). The vessel is purged with H$_2$ and is stirred at RT under 1 atm of H$_2$ overnight. The mixture is filtered through celite and the solvent is removed in vacuo to afford phenol 25a3.

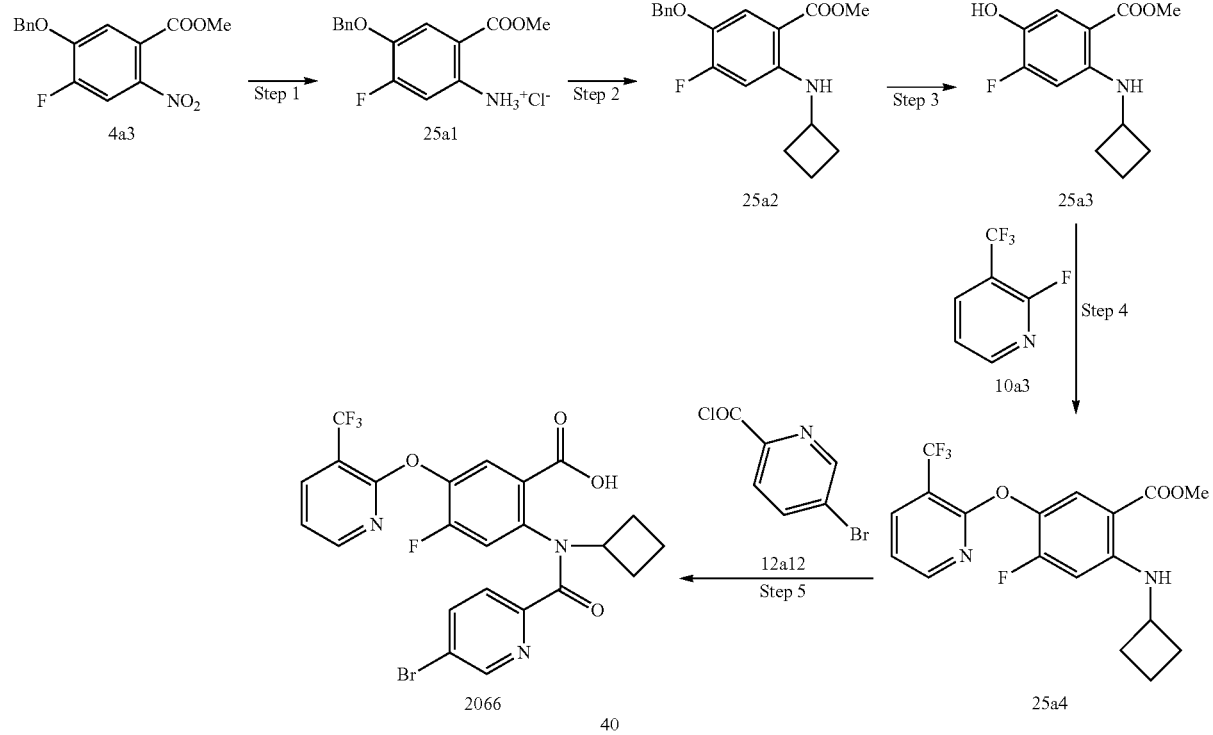

Step 1a:

The nitro intermediate 4a3 (63.8 g, 212 mmol) is diluted in THF (1 L). Aqueous hydrochloric acid (1 M, 500 mL) is added followed by tin powder (55 g, 467 mmol). The mixture is stirred for about 2 hours at RT. The reaction mixture is then diluted in EtOAc and the pH of the mixture is adjusted to 7 by the addition of 1 N NaOH. The organic phase is separated then washed with water and brine. The organic phase is then dried over NaSO$_4$ and solvent is removed to afford an aniline.

Step 1b:

The aniline (97.1 g, 377 mmol) is combined with anhydrous Et$_2$O (1 L) and the mixture is treated by the slow addition of HCl (2 M in ether, 2 L). The resulting hydrochloride salt 25a1 is collected by filtration and washed with excess ether.

Step 2:

Reference: Apodacca, R.; Xiao, W. *Org. Lett.* 2001, 3, 1745.

The HCl salt of 25a1 is converted to the free amine by washing a solution in EtOAc several times with saturated aqueous NaHCO$_3$. The organic phase is dried with MgSO$_4$, filtered and the solvent is removed under reduced pressure.

To a mixture of free base aniline 25a1 (275 mg, 1.0 mmol) in THF (5 mL) is added cyclobutanone (150 μL, 2.0 mmol) followed by Bu$_2$SnCl$_2$ (15 mg, 0.05 mmol). The mixture is stirred for about 5 minutes at RT before phenylsilane (140 μL, 1.1 mmol) is added. The mixture is stirred for about 4 days at RT before dilution with saturated aqueous NaHCO$_3$ followed by extraction with EtOAc (×2). The combined organic Step 4:

The S$_N$Ar coupling of phenol 25a3 with fluoropyridine 10a3 to produce intermediate 25a4 is performed as described in example 1A step 1.

Step 5:

Aniline 25a4 is coupled to acid chloride 12a12 followed by saponification to prepared compound 2066 using the protocol described in example 18A step 1.

Example 26A

Preparation of Compound 2068

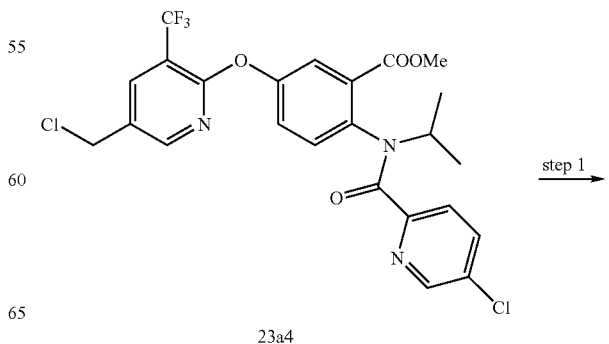

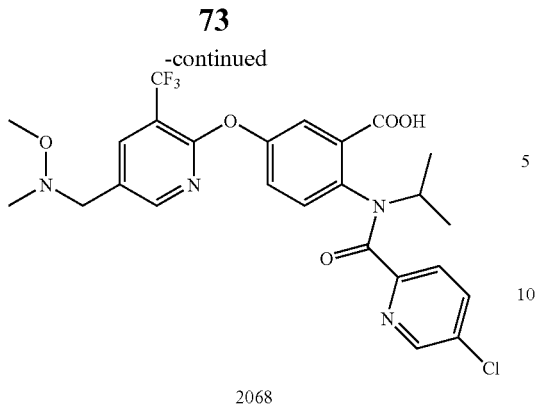

2068

Step 1:

A mixture of benzylchloride 23a4 (50 mg, 0.09 mmol), N,O-dimethylhydroxylamine hydrochloride (13 mg, 0.14 mmol) and Et$_3$N (0.026 mL, 0.18 mmol) in DMF (1 mL) is stirred at 70° C. overnight. After the mixture cools to RT, MeOH (0.5 mL) and LiOH—H$_2$O (39 mg, 0.9 mmol) are added and the mixture is stirred at RT overnight. The mixture is acidified with AcOH and then purified by preparative HPLC to isolate compound 2068.

Example 27A

Preparation of Compound 2073

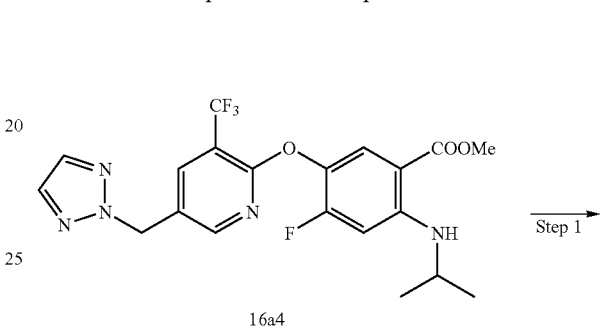

Step 1:

To a mixture of compound 2030 (40 mg, 0.08 mmol) in DCM (1 mL) is added m-CPBA (19 mg, 0.09 mmol). The mixture is stirred overnight at RT. Another portion of m-CPBA is added and the mixture is stirred again for an additional day. The mixture is concentrated and the residue is taken-up in AcOH and then injected onto a preparative HPLC to isolate compound 2073.

Example 28A

Method J

Preparation of Compound 2074

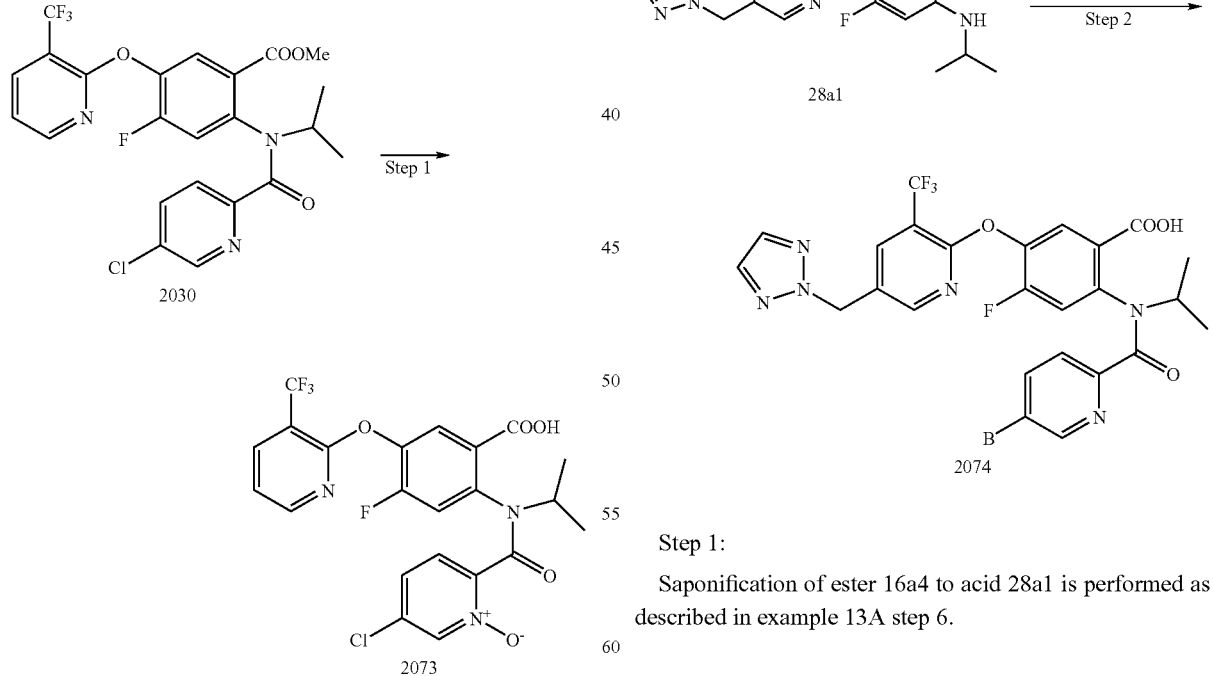

Step 1:

Saponification of ester 16a4 to acid 28a1 is performed as described in example 13A step 6.

Step 2:

Coupling of aniline 28a1 to acid chloride 12a12 to form compound 2074 is performed as described in example 13A step 7.

Example 29A

Method K

Preparation of Compound 2075

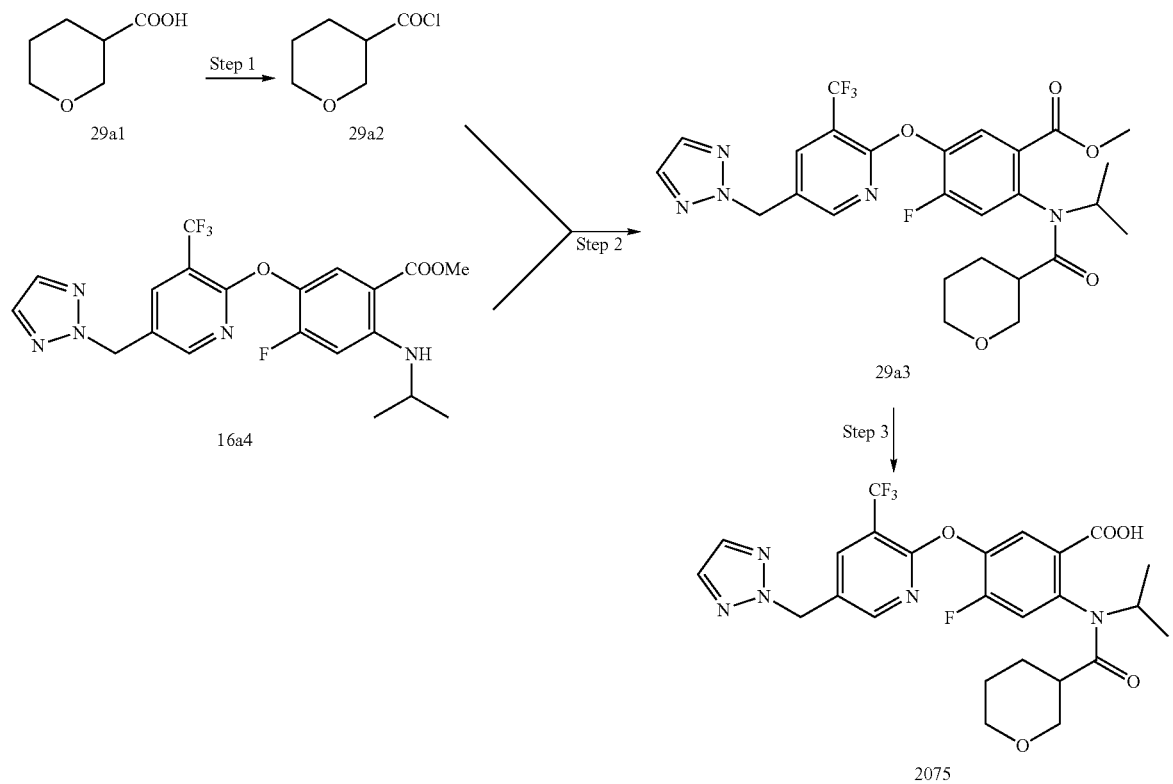

Step 1:

Acid chloride 29a2 is prepared from acid 29a1 using the protocol described in example 1A step 3.

Step 2:

To a mixture of aniline 16a4 (90 mg, 0.20 mmol) in anhydrous DCE (2 mL) is added acid chloride 29a2 (208 mg, 1.4 mmol) and anhydrous pyridine (243 μL, 3.0 mmol). The mixture is heated in a microwave oven at 170° C. for about 30 minutes. The mixture is diluted in EtOAc and washed with saturated aqueous $NaHCO_3$ and brine. The organic phase is dried over $Na_2SO_4$ and filtered. Silica gel is added to the filtrate and the mixture is concentrated. The silica gel dry-packed column is subjected to flash chromatography (30 to 90% EtOAc in Hex) to isolate amide 29a3.

Step 2:

To a mixture of ester 29a3 (57 mg, 0.1 mmol) in THF (2 mL) and DMSO (0.5 mL) is added aqueous NaOH (5 N, 200 μL, 1.0 mmol). The mixture is warmed to 50° C. and is stirred for about 1 hour. The mixture is acidified with AcOH (0.5 mL) before being filtered and injected onto a preparative HPLC to isolate compound 2075.

Example 30A

Preparation of Compound 2079

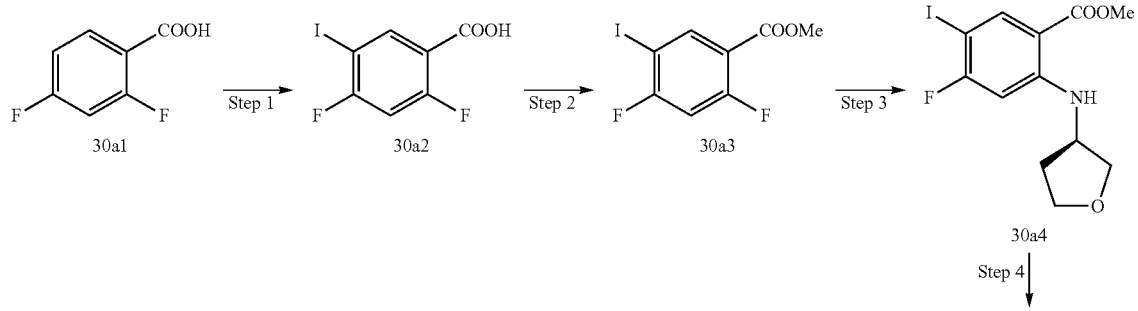

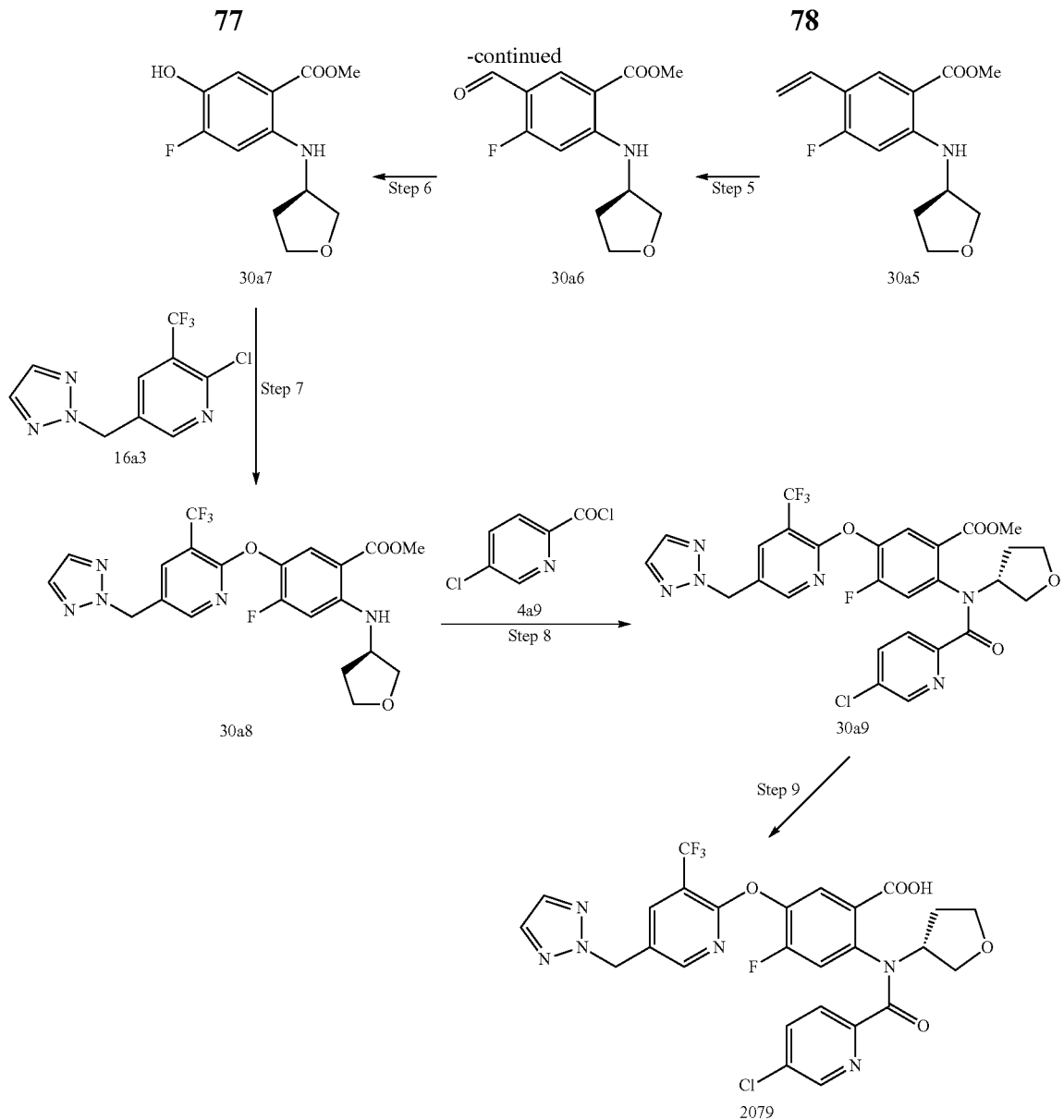

Step 1:
Reference: PCT/JP2005/009604

To a mixture of 2,4-difluorobenzoic acid 30a1 (5.00 g, 31.6 mmol) in concentrated $H_2SO_4$ (20 mL) chilled to −5° C. is added NIS (6.83 g, 30.4 mmol) portion-wise. The mixture is allowed to warm to RT and stirred overnight. The mixture is poured over ice then diluted with 10% aqueous sodium sulfite. The resulting solid is collected by filtration and washed with excess water (200 mL). The solid is taken-up in hot aqueous ethanol (50%) and the mixture is allowed to cool to RT (~1 hour), then chilled to 0° C. The solid 30a2 is recovered by filtration.

Step 2:
A mixture of acid 30a2 (37 g, 130 mmol) and concentrated $H_2SO_4$ (9 mL) in MeOH (200 mL) is heated to reflux and stirred overnight. The mixture is allowed to cool to RT before being partially concentrated. The residue is diluted in EtOAc then washed with saturated aqueous $NaHCO_3$ (×3) and brine. The organic phase is dried over $Na_2SO_4$, filtered and concentrated to afford methyl ester 30a3.

Step 3:
To a mixture of difluoroarene 30a3 (1.00 g, 3.4 mmol) in DMF (30 mL) is added $K_2CO_3$ (700 mg, 5.0 mmol) and (R)-tetrahydrofuran-3-amine-HCl (415 mg, 3.4 mmol). The mixture is heated to about 75° C. and stirred overnight. The mixture is partitioned between water and EtOAc. The organic phase is separated then washed with saturated aqueous $NaHCO_3$ and brine, dried over $Na_2SO_4$, filtered and concentrated. The residue is subjected to flash chromatography (0 to 30% EtOAc in Hex) to isolate aniline 30a4.

Step 4:
To a mixture of iodoarene 30a4 (413 mg, 1.1 mmol) in DMF (12 mL) is added tributylvinyltin (396 μL, 1.4 mmol) and $(Ph_3P)_4Pd$ (131 mg, 0.11 mmol). The mixture is degassed (Ar) before the vessel is sealed, then heated to about 110° C. and stirred for about 2.5 hours. The mixture is allowed to cool to RT then is diluted in EtOAc and washed with saturated aqueous $NaHCO_3$ and brine. The organic phase is dried over $Na_2SO_4$, filtered and concentrated. The residue is subjected to flash chromatography (0 to 30% EtOAc in Hex) to isolate alkene 30a5.

Step 5a:

To a mixture of alkene 30a5 (287 mg, 1.1 mmol) in acetone (7 mL), t-BuOH (2 mL) and water (1.5 mL), chilled to 0° C., is added $OsO_4$ (2.5% solution in t-BuOH, 676 μL, 0.05 mmol) and NMO (190 mg, 1.6 mmol). The mixture is stirred for about 2 hours at 0° C. before being poured into 10% aqueous $Ns_2S_2O_3$. The aqueous mixture is extracted with EtOAc (×2). The combined organic phases are washed with 10% aqueous $Ns_2S_2O_3$ and brine, dried over $Na_2SO_4$, filtered and concentrated. The dial is utilized in the next step without further purification.

Step 5b:

The residue from above is taken-up in THF (4.5 mL) and water (4.5 mL). The resulting mixture is chilled to 0° C. and $NaIO_4$ (34 g, 160 mmol) is added. The mixture stirs for 2 hours at 0° C. before being diluted in saturated aqueous $NaHCO_3$. The aqueous mixture is extracted with EtOAc (×2). The combined organic phases are washed with saturated aqueous $NaHCO_3$ and brine, dried over $Na_2SO_4$, filtered and concentrated. The residue is subjected to flash chromatography (10 to 30% EtOAc in Hex) to isolate aldehyde 30a6.

Step 6:

To a mixture of aldehyde 30a6 (206 mg, 0.77 mmol) in MeOH (1.5 mL), chilled to 0° C., is added concentrated $H_2SO_4$ (72 μL, 1.2 mmol) and hydrogen peroxide (30% aqueous solution, 131 μL, 1.2 mmol). The mixture is stirred at 0° C. for 1.5 hour before the mixture is diluted in 10% aqueous $KH_2PO_4$. The aqueous mixture is extracted with $Et_2O$. The organic phase is washed with 10% aqueous $KH_2PO_4$ and brine (×3). The combined aqueous phases are back-extracted with $Et_2O$ and the organic phase is washed with 10% aqueous $KH_2PO_4$ and brine (×3). The combined organic phases are dried over $Na_2SO_4$, filtered and concentrated. Crude phenol 30a7 is utilized in the next step without further purification.

Step 7:

To a mixture of phenol 30a7 (197 mg, 0.77 mmol) and chloropyridine 16a3 (203 mg, 0.77 mmol) in DMSO (3 mL) is added $Cs_2CO_3$ (376 mg, 1.2 mmol). The mixture is heated to 65° C. and stirs for 1 hour. The mixture is diluted in saturated aqueous $NaHCO_3$ then extracted with EtOAc (×2). The combined organic extracts are washed with brine, dried over $MgSO_4$, filtered and concentrated under reduced pressure. The residue is subjected to flash chromatography (10 to 50% EtOAc in Hex) to isolate ether 30a8.

Step 8:

To a mixture of aniline 30a8 (135 mg, 0.28 mmol) in anhydrous DCE (3 mL) is added acid chloride 4a9 (99 mg, 0.56 mmol), DMAP (3 mg, 0.03 mmol) and anhydrous pyridine (131 μL, 1.7 mmol). The mixture is heated in a microwave oven at 140° C. for about 1 hour. The mixture is diluted in EtOAc and washed with 1 N HCl, water, saturated aqueous $NaHCO_3$ and brine. The organic phase is dried over $Na_2SO_4$, filtered and concentrated. The residue is subjected to flash chromatography (20 to 100% EtOAc in Hex) to isolate ether 30a9.

Step 9:

Ester 30a9 is converted to compound 2079 using conditions described in example 29A step 2.

Example 31

Inhibition of NS5B RNA Dependent RNA Polymerase Activity

Representative compounds of the invention are tested for inhibitory activity against the hepatitis C virus RNA dependent polymerase (NS5B), according to the protocol described below.

The HCV His-NS5BΔ1 polymerase [SEQ ID NO.1] lacks the C-terminal 21 amino acids and is expressed with an N-terminal hexa-histidine tag from a pET-based vector in *E. coli* strain JM109(DE3) and purified as described in McKercher et al., (2004) Nucleic Acids Res. 32: 422-431. The homogeneous enzyme preparation is stored at −20° C. in storage buffer (25 mM Tris/HCl pH 7.5, 300 mM NaCl, 5 mM DTT, 1 M EDTA and 30% (v/v) glycerol).

The purified His-NS5BΔ21 polymerase is reconstituted in an assay that measures the incorporation of $^3$H-UTP during the elongation of a biotin-oligo-$(U)_{12}$ RNA primer annealed to a homopolymeric poly(A) template. The test compound is added first, followed by the substrate, then the enzyme. At the end of the reaction, streptavidin scintillation proximity assay (SPA) beads are added and the radioactivity from the captured double-stranded RNA product is quantified on TopCount instrument (Packard).

The components of the assay reaction are: 20 mM Tris-HCl pH 7.5, 1 mM TCEP, 1 mM EDTA, 5 mM $MgCl_2$, 0.01% w/v BSA, 5% v/v DMSO, 10 μg/mL Poly(A), 1 μg/mL Biotin-oligo-$(U)_{12}$, 333 nM UTP, 0.01 mCi/mL, (300 nM)$^3$H-UTP, 80 units/mL Rnasin, 12.5 nM His-NS5BΔ21 polymerase and test inhibitor compound that is serially diluted over a large concentration range. The assay is performed in 384-well plates with a 1.5 hour incubation at about 22° C., and then stopped with a solution of 0.5 M EDTA and the products captured with Streptavidin-coated beads. Following the addition of 6 M CsCl to the bottom of each well, the plate is left at room temperature for about 90 minutes before counting for 60 seconds on a TopCount. The calculated % inhibition values are then used to determine $IC_{50}$, slope factor (n) and maximum inhibition $(I_{max})$ by the non-linear regression routine NLIN procedure of SAS.

Example 32

Specificity of NS5B RNA Dependent RNA Polymerase Inhibition

Representative compounds of the invention are tested for inhibitory activity against polio virus RNA dependent RNA polymerase and calf thymus DNA dependent RNA polymerase II as described in McKercher et al., (2004) Nucleic Acids Res. 32: 422-431.

Example 33

Cell-Based Luciferase Reporter HCV RNA Replication Assay

Representative compounds of the invention are tested for activity as inhibitors of hepatitis C virus RNA replication in cells expressing a stable subgenomic HCV replicon, using the assay described in WO 2005/028501, herein incorporated by reference.

TABLES OF COMPOUNDS

The following tables list compounds representative of the invention. Representative compounds listed in Tables 1 and 2 below are tested in the assay of Example 31 and are found to have $IC_{50}$ value below 30 μM. Representative compounds listed in Tables 1 and 2 below are tested in the assay of Example 33 and are found to have a $EC_{50}$ values below 30 μM.

Retention times $(t_R)$ for each compound are measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

| Cpd | R20 | R21 | R3 | R5 | R6 | $t_R$ (min) | m/z (MH)+ | Method |
|---|---|---|---|---|---|---|---|---|
| 1001 | H | H | H | isobutyl | 5-bromothiophen-2-yl | 6.6 | 462.1 | EX 1A |
| 1002 | H | CF3 | H | isobutyl | 2-methylthiazol-4-yl | 6.2 | 465.1 | Ex 3AA |
| 1003 | H | CF3 | H | isobutyl | 1,5-dimethyl-1H-pyrazol-3-yl | 6 | 462.1 | A |
| 1004 | 2-(pyridin-3-yloxy)ethyl | CF3 | F | isobutyl | 5-chloropyridin-2-yl | 5.1 | 604 | B |
| 1005 | 2-(pyrimidin-2-ylthio)ethyl | CF3 | F | isobutyl | 5-chloropyridin-2-yl | 7.1 | 621 | B |
| 1006 | 2-(pyridin-3-yloxy)ethyl | CF3 | H | isobutyl | 5-chloropyridin-2-yl | 4.8 | 586.1 | B |
| 1007 | 2-(pyrimidin-2-ylthio)ethyl | CF3 | H | isobutyl | 5-chloropyridin-2-yl | 7.0 | 603 | B |

TABLE 1-continued
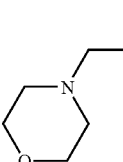
| Cpd | R²⁰ | R²¹ | R³ | R⁵ | R⁶ | t_R (min) | m/z (MH)⁺ | Method |
|---|---|---|---|---|---|---|---|---|
| 1008 | 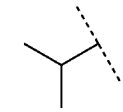 | CF₃ | F | 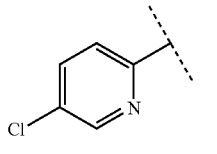 | 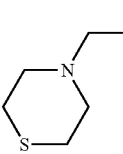 | 4.5 | 596 | EX 7A C |
| 1009 | 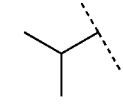 | CF₃ | F | 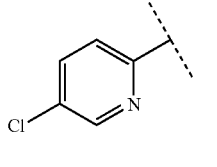 | 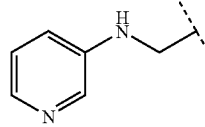 | 4.8 | 612 | C |
| 1010 | 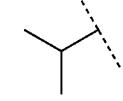 | CF₃ | F | 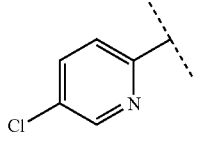 | 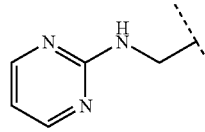 | 4.9 | 603 | B |
| 1011 | 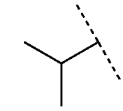 | CF₃ | F | 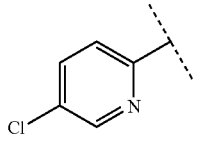 | 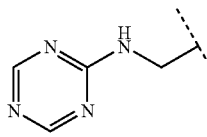 | 5.5 | 604 | B |
| 1012 | 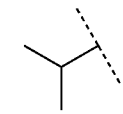 | CF₃ | F | 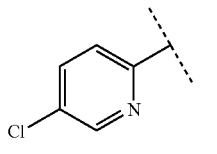 | 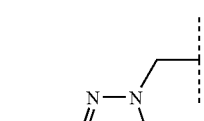 | 5.4 | 605 | B |
| 1013 | 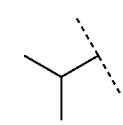 | CF₃ | F | 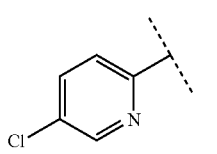 | 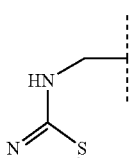 | 6.5 | 605.1 | B |
| 1014 | 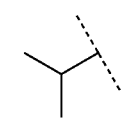 | CF₃ | F | 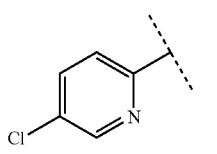 | | 4.9 | 609 | B |

TABLE 1-continued

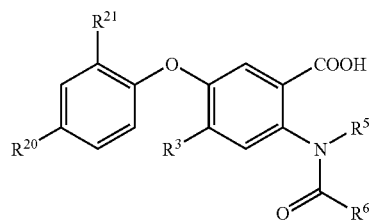

| Cpd | R20 | R21 | R3 | R5 | R6 | $t_R$ (min) | m/z (MH)+ | Method |
|---|---|---|---|---|---|---|---|---|
| 1015 | 1H-pyrrolo[2,3-b]pyridin-1-ylmethyl | CF$_3$ | F | isobutyl | 5-chloropyridin-2-yl | 6.9 | 627 | B |
| 1016 | (6-ethylpyridin-2-yl)aminomethyl | CF$_3$ | F | isobutyl | 5-chloropyridin-2-yl | 5.2 | 631.1 | EX 6A B |
| 1017 | (2-chloropyridin-3-yl)aminomethyl | CF$_3$ | F | isobutyl | 5-chloropyridin-2-yl | 7.0 | 637 | B |
| 1018 | morpholin-4-ylmethyl | CF$_3$ | H | isobutyl | 5-chloropyridin-2-yl | 4.3 | 578.1 | C |
| 1019 | thiomorpholin-4-ylmethyl | CF$_3$ | H | isobutyl | 5-chloropyridin-2-yl | 4.5 | 594.1 | C |
| 1020 | 1H-pyrazol-1-ylmethyl | CF$_3$ | H | isobutyl | 5-chloropyridin-2-yl | 6.3 | 559.1 | B |
| 1021 | (pyridin-3-yl)aminomethyl | CF$_3$ | H | isobutyl | 5-chloropyridin-2-yl | 4.6 | 585.1 | B |

TABLE 1-continued

| Cpd | R20 | R21 | R3 | R5 | R6 | tR (min) | m/z (MH)+ | Method |
|---|---|---|---|---|---|---|---|---|
| 1022 | pyrimidin-2-ylaminoethyl | CF3 | H | isobutyl | 5-chloropyridin-2-yl | 5.3 | 586.1 | B |
| 1023 | 1,3,5-triazin-2-ylaminoethyl | CF3 | H | isobutyl | 5-chloropyridin-2-yl | 5.1 | 587 | B |
| 1024 | (3,5-dimethylpyrazol-1-yl)ethyl | CF3 | H | isobutyl | 5-chloropyridin-2-yl | 6.3 | 587.1 | B |
| 1025 | thiazol-2-ylaminoethyl | CF3 | H | isobutyl | 5-chloropyridin-2-yl | 4.7 | 591 | B |
| 1026 | (7-azaindol-1-yl)ethyl | CF3 | H | isobutyl | 5-chloropyridin-2-yl | 6.7 | 609.1 | B |
| 1027 | (indazol-1-yl)ethyl | CF3 | H | isobutyl | 5-chloropyridin-2-yl | 7.2 | 609.1 | B |
| 1028 | (6-ethylpyridin-2-yl)aminoethyl | CF3 | H | isobutyl | 5-chloropyridin-2-yl | 5.0 | 613.1 | B |

TABLE 1-continued

| Cpd | R20 | R21 | R3 | R5 | R6 | tR (min) | m/z (MH)+ | Method |
|---|---|---|---|---|---|---|---|---|
| 1029 | 3-(NH)-2-chloropyridin-... | CF3 | H | isobutyl | 5-chloropyridin-2-yl | 6.9 | 619 | B |
| 1030 | 2-imino-thiazol-3-yl-methyl | CF3 | F | isobutyl | 5-chloropyridin-2-yl | 4.6 | 609 | B |
| 1031 | 7-azaindol-1-yl-methyl | CF3 | F | isobutyl | 5-chloropyridin-2-yl | 4.9 | 627.1 | B |
| 1032 | indazol-2-yl-methyl | CF3 | F | isobutyl | 5-chloropyridin-2-yl | 7.1 | 627 | B |
| 1033 | 2-imino-thiazol-3-yl-methyl | CF3 | H | isobutyl | 5-chloropyridin-2-yl | 4.4 | 591 | B |
| 1034 | indazol-2-yl-methyl | CF3 | H | isobutyl | 5-chloropyridin-2-yl | 6.9 | 609.1 | B |

TABLE 1-continued

| Cpd | R²⁰ | R²¹ | R³ | R⁵ | R⁶ | $t_R$ (min) | m/z (MH)⁺ | Method |
|---|---|---|---|---|---|---|---|---|
| 1035 | 7-azaindole-CH₂- | CF₃ | H | isobutyl | 5-chloropyridin-2-yl | 4.6 | 609.1 | B |
| 1036 | pyrazol-1-yl-CH₂- | CF₃ | F | isobutyl | 5-chloropyridin-2-yl | 6.1 | 577.3 | EX 8A |
| 1037 | thiazol-5-yl-CH₂- | CF₃ | F | isobutyl | 5-chloropyridin-2-yl | 6.7 | 594.1 | EX 9A D |

TABLE 2

| Cpd | R²⁰ | R³ | R⁵ | R⁶ | $t_R$ (min) | m/z (MH)⁺ | Method |
|---|---|---|---|---|---|---|---|
| 2001 | H | H | isobutyl | 5-bromothiophen-2-yl | 6.9 | 528.9 | EX 11A E |
| 2002 | H | H | isobutyl | 5-bromopyridin-2-yl | 6.3 | 523.9 | E |

TABLE 2-continued
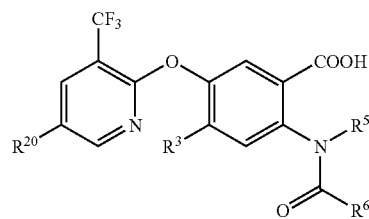
| Cpd | R20 | R3 | R5 | R6 | $t_R$ (min) | m/z (MH)+ | Method |
|---|---|---|---|---|---|---|---|
| 2003 | morpholinoethyl | H | isobutyl | 5-bromopyridin-2-yl | 4.3 | 623.1 | EX 12A |
| 2004 | H | H | isobutyl | 2,5-dichlorothiophen-3-yl | 7 | 518.9 | E |
| 2005 | H | H | isobutyl | 4-bromo-1,3-dimethylpyrazol-5-yl | 6.4 | 541 | E |
| 2006 | H | H | isobutyl | 3-chloro-5-trifluoromethylpyridin-2-yl | 6.8 | 548 | E |
| 2007 | H | H | isobutyl | 3,5-dichloropyridin-2-yl | 6.5 | 514 | E |
| 2008 | H | H | isobutyl | 5-chloropyridin-2-yl | 6.2 | 480 | E |
| 2009 | H | H | isobutyl | 3-fluoro-5-hydroxypyridin-2-yl | 5.4 | 480 | E |
| 2010 | H | Cl | isobutyl | 5-bromopyridin-2-yl | 5.8 | 557.9 | EX 13A |

TABLE 2-continued

| Cpd | R20 | R3 | R5 | R6 | tR (min) | m/z (MH)+ | Method |
|---|---|---|---|---|---|---|---|
| 2011 | H | H | cyclobutylmethyl | 5-bromopyridin-2-yl | 6.5 | 536 | EX 15A F |
| 2012 | H | H | 2,3,3-trimethylbutyl | 5-bromopyridin-2-yl | 7.3 | 566 | F |
| 2013 | H | H | sec-butyl | 5-bromopyridin-2-yl | 6.7 | 538 | F |
| 2014 | H | H | hexan-2-yl | 5-bromopyridin-2-yl | 7.1 | 552 | F |
| 2015 | H | H | 3,3,3-trifluoropropyl | 5-bromopyridin-2-yl | 6.8 | 564 | F |
| 2016 | H | H | neopentyl | 5-bromopyridin-2-yl | 7.0 | 552 | F |
| 2017 | H | H | isobutyl | 5-bromopyridin-2-yl | 6.8 | 538 | F |
| 2018 | H | H | isopentyl | 5-bromopyridin-2-yl | 7.1 | 552 | F |

TABLE 2-continued

| Cpd | R20 | R3 | R5 | R6 | $t_R$ (min) | m/z (MH)+ | Method |
|---|---|---|---|---|---|---|---|
| 2019 | H | H | tetrahydrothiophene 1,1-dioxide-3-yl | 5-bromopyridin-2-yl | 5.6 | 600 | F |
| 2020 | H | H | (S)-2-methylbutyl | 5-bromopyridin-2-yl | 7.1 | 552 | F |
| 2021 | 2-(pyridin-3-yloxy)ethyl | F | isobutyl | 5-chloropyridin-2-yl | 4.8 | 605 | B |
| 2022 | 2-(pyrimidin-2-ylthio)ethyl | F | isobutyl | 5-chloropyridin-2-yl | 6.9 | 622 | B |
| 2023 | 2-morpholinoethyl | F | isobutyl | 5-chloropyridin-2-yl | 4.4 | 597.1 | C |
| 2024 | 2-thiomorpholinoethyl | F | isobutyl | 5-chloropyridin-2-yl | 4.6 | 613 | C |
| 2025 | H | H | 2-(5-methylisoxazol-3-yl)ethyl | 5-bromopyridin-2-yl | 6.3 | 577 | F |

TABLE 2-continued

| Cpd | R20 | R3 | R5 | R6 | $t_R$ (min) | m/z (MH)+ | Method |
|---|---|---|---|---|---|---|---|
| 2026 | H | H | cyclopropylmethyl | 5-bromopyridin-2-yl | 6.1 | 522 | F |
| 2027 | (2H-1,2,3-triazol-2-yl)methyl | | isobutyl | 5-chloropyridin-2-yl | 6.2 | 579.0 | EX 16A |
| 2028 | (2H-1,2,3-triazol-2-yl)methyl | H | isobutyl | 5-bromopyridin-2-yl | 6.6 | 605.0 | EX 18A G |
| 2029 | (2H-1,2,3-triazol-2-yl)methyl | H | isobutyl | 5-chloropyridin-2-yl | 6.5 | 561.1 | G |
| 2030 | H | F | isobutyl | 5-chloropyridin-2-yl | 6.2 | 497.9 | EX 19A |
| 2031 | —CH2OCH3 | F | isobutyl | 5-chloropyridin-2-yl | 6.3 | 542.0 | EX 21A |
| 2032 | H | CN | isobutyl | 5-chloropyridin-2-yl | 5.9 | 505.0 | EX 22A H |
| 2033 | (pyrimidin-5-yl)methyl | H | isobutyl | 5-chloropyridin-2-yl | 5.1 | 572.1 | EX 24A I |

TABLE 2-continued

| Cpd | R20 | R3 | R5 | R6 | tR (min) | m/z (MH)+ | Method |
|---|---|---|---|---|---|---|---|
| 2034 | pyrimidin-5-ylmethyl | F | isobutyl | 5-chloropyridin-2-yl | 5.3 | 590.1 | I |
| 2035 | (2H-1,2,3-triazol-2-yl)methyl | CN | isobutyl | 5-chloropyridin-2-yl | 5.9 | 586.1 | H |
| 2036 | pyridin-3-ylmethyl | F | isobutyl | 5-chloropyridin-2-yl | 4.3 | 589.1 | I |
| 2037 | 2-(pyridin-3-yloxy)ethyl | H | isobutyl | 5-chloropyridin-2-yl | 4.6 | 587.1 | B |
| 2038 | 2-(pyrimidin-2-ylthio)ethyl | H | isobutyl | 5-chloropyridin-2-yl | 6.7 | 604 | B |
| 2039 | (1H-pyrazol-1-yl)methyl | F | isobutyl | 5-chloropyridin-2-yl | 6.2 | 578 | B |
| 2040 | 2-(pyridin-3-ylamino)ethyl | F | isobutyl | 5-chloropyridin-2-yl | 4.6 | 604 | B |
| 2041 | 2-(pyrimidin-2-ylamino)ethyl | F | isobutyl | 5-chloropyridin-2-yl | 5.5 | 605 | B |

TABLE 2-continued

| Cpd | R20 | R3 | R5 | R6 | t_R (min) | m/z (MH)+ | Method |
|---|---|---|---|---|---|---|---|
| 2042 | pyrazin-2-yl-NH-CH2- | F | isobutyl | 5-chloropyridin-2-yl | 5.9 | 605 | B |
| 2043 | 3,5-dimethylpyrazol-1-yl-CH2- | F | isobutyl | 5-chloropyridin-2-yl | 6.4 | 606.1 | B |
| 2044 | pyridin-2-yl-NH-CH2- | F | isobutyl | 5-chloropyridin-2-yl | 4.7 | 610 | B |
| 2045 | 7-azaindol-1-yl-CH2- | F | isobutyl | 5-chloropyridin-2-yl | 6.8 | 628 | B |
| 2046 | indazol-1-yl-CH2- | F | isobutyl | 5-chloropyridin-2-yl | 7.2 | 628 | B |
| 2047 | (6-ethylpyridin-2-yl)-NH-CH2- | F | isobutyl | 5-chloropyridin-2-yl | 5.1 | 632.1 | B |
| 2048 | (2-chloropyridin-3-yl)-NH-CH2- | F | isobutyl | 5-chloropyridin-2-yl | 6.8 | 638 | B |
| 2049 | morpholin-4-yl-CH2- | H | isobutyl | 5-chloropyridin-2-yl | 4.2 | 579.1 | C |

TABLE 2-continued

| Cpd | R20 | R3 | R5 | R6 | $t_R$ (min) | m/z (MH)+ | Method |
|---|---|---|---|---|---|---|---|
| 2050 | thiomorpholinyl-CH2- | H | isobutyl | 5-chloropyridin-2-yl | 4.3 | 595 | C |
| 2051 | pyrazol-1-yl-CH2- | H | isobutyl | 5-chloropyridin-2-yl | 6.0 | 560.1 | B |
| 2052 | pyridin-3-yl-NH-CH2- | H | isobutyl | 5-chloropyridin-2-yl | 4.4 | 586.1 | B |
| 2053 | pyrimidin-2-yl-NH-CH2- | H | isobutyl | 5-chloropyridin-2-yl | 5.1 | 587.1 | B |
| 2054 | 3,5-dimethylpyrazol-1-yl-CH2- | H | isobutyl | 5-chloropyridin-2-yl | 6.2 | 588.1 | B |
| 2055 | thiazol-2-yl-NH-CH2- | H | isobutyl | 5-chloropyridin-2-yl | 4.5 | 592 | B |
| 2056 | 7-azaindol-1-yl-CH2- | H | isobutyl | 5-chloropyridin-2-yl | 6.6 | 610.1 | B |
| 2057 | indazol-1-yl-CH2- | H | isobutyl | 5-chloropyridin-2-yl | 7.0 | 610.1 | B |

TABLE 2-continued

| Cpd | R[20] | R[3] | R[5] | R[6] | $t_R$ (min) | m/z (MH)+ | Method |
|---|---|---|---|---|---|---|---|
| 2058 | 6-ethyl-pyridin-2-yl-NH- | H | isobutyl | 5-chloro-pyridin-2-yl | 4.8 | 614.1 | B |
| 2059 | 2-chloro-pyridin-3-yl-NH- | H | isobutyl | 5-chloro-pyridin-2-yl | 6.6 | 620 | B |
| 2060 | 2-imino-thiazol-3-yl-methyl | F | isobutyl | 5-chloro-pyridin-2-yl | 4.5 | 610.0 | B |
| 2061 | pyrrolo[2,3-b]pyridin-1-yl-methyl | F | isobutyl | 5-chloro-pyridin-2-yl | 4.7 | 628 | B |
| 2062 | indazol-1-yl-methyl | F | isobutyl | 5-chloro-pyridin-2-yl | 7.0 | 628 | B |
| 2063 | 2-imino-thiazol-3-yl-methyl | H | isobutyl | 5-chloro-pyridin-2-yl | 4.3 | 592 | B |
| 2064 | pyrazolo[3,4-b]pyridin-1-yl-methyl | H | isobutyl | 5-chloro-pyridin-2-yl | 4.5 | 610A | B |

TABLE 2-continued
| Cpd | R20 | R3 | R5 | R6 | tR (min) | m/z (MH)+ | Method |
|---|---|---|---|---|---|---|---|
| 2065 | 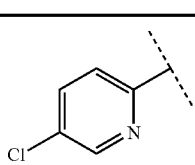 | H |  | 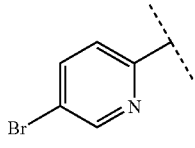 | 6.7 | 610.1 | B |
| 2066 | H | F |  | 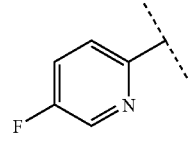 | 7.1 | 556.0 | EX25A |
| 2067 |  | H |  | 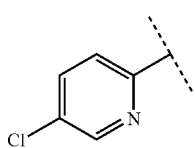 | 6.1 | 545.1 | G |
| 2068 |  | H |  | 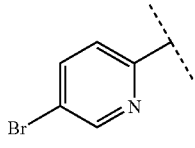 | 5.4 | 552.1 | EX 26A |
| 2069 | 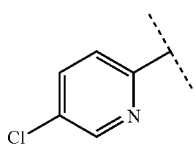 | F |  | 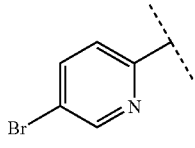 | 5.1 | 631.3 | C |
| 2070 |  | F |  | 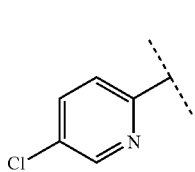 | 5.1 | 617.3 | C |
| 2071 |  | F |  | 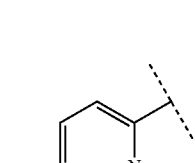 | 5.2 | 675.3 | C |

TABLE 2-continued
| Cpd | R20 | R3 | R5 | R6 | $t_R$ (min) | m/z (MH)+ | Method |
|---|---|---|---|---|---|---|---|
| 2072 |  | F |  |  | 5.2 | 661.3 | C |
| 2073 | H | F |  |  | 5.3 | 514.1 | EX 27A |
| 2074 |  | F |  |  | 6.5 | 625.1 | EX 28A J |
| 2075 |  | F |  |  | 6.1 | 552.1 | EX 29A K |
| 2076 |  | F |  |  | 6.5 | 595.1 | D |
| 2077 |  | F |  |  | 5.8 | 552.2 | K |
| 2078 |  | F |  |  | 5.7 | 584.2 | J |

TABLE 2-continued

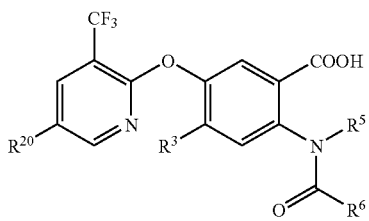

| Cpd | R²⁰ | R³ | R⁵ | R⁶ | tR (min) | m/z (MH)⁺ | Method |
|---|---|---|---|---|---|---|---|
| 2079 | 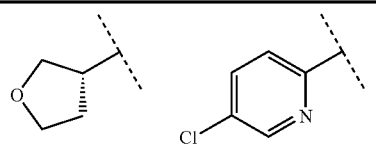 | F | 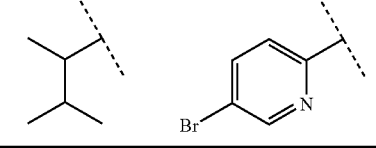 | 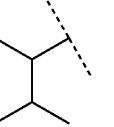 | 6.1 | 607.2 | EX 30A |
| 2080 | H | H | 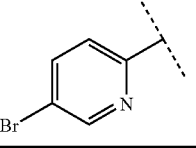 |  | 7.1 | 552 | F |

All of the documents cited herein are incorporated into the application by reference, as if each of them is individually incorporated. Further, it would be appreciated that in the teachings of the invention, those skilled in the art could make certain changes or modifications to the invention, and these equivalents would still be within the scope of the invention defined by the appended claims of the application.

The invention claimed is:

1. A compound of formula (I):

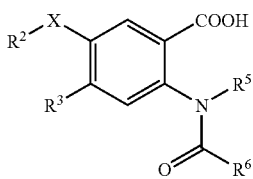

wherein:
X is selected from O and S;
$R^2$ is of the formula:

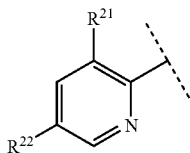

wherein $R^{21}$ is selected from H, halo, $(C_{1-6})$alkyl, $(C_{1-6})$haloalkyl, $(C_{3-7})$cycloalkyl and —O—$(C_{1-6})$haloalkyl; and $R^{22}$ is $R^{20}$, wherein $R^{20}$ in each case is independently selected from:

a) halo, cyano or nitro;
b) $R^7$, —C(=O)—$R^7$, —C(=O)—O—$R^7$, —O—$R^7$, —S—$R^7$, —SO—$R^7$, —SO$_2$—$R^7$, —$(C_{1-6})$alkylene-$R^7$, —$(C_{1-6})$alkylene-C(=O)—$R^7$, —$(C_{1-6})$alkylene-C(=O)—O—$R^7$, —$(C_{1-6})$alkylene-O—$R^7$, —$(C_{1-6})$alkylene-S—$R^7$, —$(C_{1-6})$alkylene-SO—$R^7$ or —$(C_{1-6})$alkylene-SO$_2$—$R^7$;
wherein $R^7$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; wherein the $(C_{1-6})$alkyl, $(C_{2-6})$alkenyl, $(C_{2-6})$alkynyl and $(C_{3-7})$cycloalkyl are optionally substituted with 1 or 2 substituents each independently selected from —OH, —$(C_{1-6})$alkyl, halo, —$(C_{1-6})$haloalkyl, $(C_{3-7})$cycloalkyl, —O—$(C_{1-6})$alkyl, cyano, COOH, —NH$_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$; and wherein each of the aryl and Het is optionally substituted with 1 to 3 substituents each independently selected from:
i) halo, cyano, oxo, thioxo, imino, —OH, —O—$(C_{1-6})$alkyl, —O—$(C_{1-6})$haloalkyl, $(C_{3-7})$cycloalkyl, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —C(=O)—NH$(C_{3-7})$cycloalkyl, —C(=O)—N$((C_{1-4})$alkyl$)(C_{3-7})$cycloalkyl, —NH$_2$, —NH$(C_{1-4})$alkyl, —N$((C_{1-4})$alkyl$)_2$, —NH$(C_{3-7})$cycloalkyl, —N$((C_{1-4})$alkyl$)(C_{3-7})$cycloalkyl or —NH—C(=O)$(C_{1-4})$alkyl;
ii) $(C_{1-6})$alkyl optionally substituted with —OH, —O—$(C_{1-6})$haloalkyl, or —O—$(C_{1-6})$alkyl; and
iii) aryl or Het, wherein each of the aryl and Het is optionally substituted with halo or $(C_{1-6})$alkyl; and
c) —N$(R^8)R^9$, —C(=O)—N$(R^8)R^9$, —O—C(=O)—N$(R^8)R^9$, —SO$_2$—N$(R^8)R^9$, —$(C_{1-6})$alkylene-N$(R^8)R^9$, —$(C_{1-6})$alkylene-C(=O)—N$(R^8)R^9$, —$(C_{1-6})$alkylene-O—C(=O)—N$(R^8)R^9$, or —$(C_{1-6})$alkylene-SO$_2$—N$(R^8)R^9$; wherein the $(C_{1-6})$alkylene is optionally substituted with 1 or 2 substituents each independently selected from —OH, —$(C_{1-6})$alkyl, halo, —$(C_{1-6})$haloalkyl$(C_{3-7})$cycloalkyl, —O—$(C_{1-6})$alkyl, cyano, COOH, —NH$_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$;
$R^8$ is in each instance independently selected from H, $(C_{1-6})$alkyl and $(C_{3-7})$cycloalkyl; and
$R^9$ is in each instance independently selected from $R^7$, —O—$(C_{1-6})$alkyl, —$(C_{1-6})$alkylene-$R^7$, —SO$_2$—$R^7$, —C(=O)—$R^7$, —C(=O)O$R^7$ and —C(=O)N$(R^8)R^7$; wherein $R^7$ and $R^8$ are as defined above;
or $R^8$ and $R^9$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;
wherein the heterocycle is optionally substituted with 1 to 3 substituents each independently selected from $(C_{1-6})$alkyl, $(C_{1-6})$haloalkyl, halo, oxo, —OH, SH, —O$(C_{1-6})$alkyl, —S$(C_{1-6})$alkyl, $(C_{3-7})$cycloalkyl, —NH$_2$, —NH$(C_{1-6})$alkyl, —N$((C_{1-6})$alkyl$)_2$, —NH$(C_{3-7})$cycloalkyl, —N$((C_{1-4})$alkyl$)(C_{3-7})$cycloalkyl, —C(=O)$(C_{1-6})$alkyl and —NHC(=O)—$(C_{1-6})$alkyl;
$R^3$ is selected from H, halo, CN, $(C_{1-4})$alkyl, —OH, —O—$(C_{1-4})$alkyl, —S—$(C_{1-4})$alkyl, —NH$_2$, —NH$(C_{1-4})$alkyl, —NH$(C_{3-7})$cycloalkyl, —N$((C_{1-4})$alkyl$)(C_{3-7})$cycloalkyl and —N$((C_{1-4})$alkyl$)_2$;
$R^5$ is H, $(C_{1-6})$alkyl, $(C_{3-7})$cycloalkyl, $(C_{3-7})$cycloalkyl-$(C_{1-6})$alkyl- or Het; the $(C_{1-6})$alkyl and Het each being optionally substituted with 1 to 4 substituents each independently selected from $(C_{1-6})$alkyl, $(C_{1-6})$haloalkyl, $(C_{3-7})$cycloalkyl, Het, —OH, —COOH, —C(=O)—$(C_{1-6})$alkyl, —C(=O)—O—$(C_{1-6})$alkyl, —SO$_2(C_{1-6})$alkyl and —C(=O)—N$(R^{51})R^{52}$; wherein $R^{51}$ is H, $(C_{1-6})$alkyl or $(C_{3-7})$cycloalkyl; and
$R^{52}$ is H, $(C_{1-6})$alkyl, $(C_{3-7})$cycloalkyl, aryl, Het, aryl-$(C_{1-3})$alkyl- or Het-$(C_{1-3})$alkyl-; wherein each of the $(C_{1-6})$alkyl, $(C_{3-7})$cycloalkyl, aryl, Het, aryl-$(C_{1-3})$alkyl- and Het-$(C_{1-3})$alkyl- are optionally substituted with 1 to 3 substituents each independently selected from $(C_{1-6})$alkyl, $(C_{1-6})$haloalkyl, halo, oxo, —OH, —O$(C_{1-6})$alkyl, —NH$_2$, —NH$(C_{1-6})$alkyl, —N((C$_{1-6}$)alkyl)$_2$, —NH(C$_{3-7}$)cycloalkyl, —N((C$_{1-4}$)alkyl)(C$_{3-7}$)cycloalkyl, —C(=O)(C$_{1-6}$)alkyl and —NHC(=O)—(C$_{1-6}$)alkyl;
wherein the (C$_{1-6}$)alkyl is optionally substituted with OH;
or R$^{51}$ and R$^{52}$, together with the N to which they are attached, are linked to form a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;
wherein the heterocycle is optionally substituted with 1 to 3 substituents each independently selected from (C$_{1-6}$)alkyl, (C$_{1-6}$)haloalkyl, halo, oxo, —OH, —O(C$_{1-6}$)alkyl, —NH$_2$, —NH(C$_{1-6}$)alkyl, —N((C$_{1-6}$)alkyl)$_2$, —NH(C$_{3-7}$)cycloalkyl, —N((C$_{1-4}$)alkyl)(C$_{3-7}$)cycloalkyl, —C(=O)(C$_{1-6}$)alkyl and —NHC(=O)—(C$_{1-6}$)alkyl;
wherein the (C$_{1-6}$)alkyl is optionally substituted with OH;
R$^6$ is pyridinyl; being optionally substituted with 1 to 5 substituents each independently selected from halo, (C$_{1-6}$)alkyl, (C$_{1-6}$)haloalkyl, (C$_{3-7}$)cycloalkyl, —OH, —SH, —O—(C$_{1-4}$)alkyl, —S—(C$_{1-4}$)alkyl and —N(R$^8$)R$^9$; wherein R$^8$ and R$^9$ are as defined above; and
Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;
a pharmaceutically acceptable salt or ester thereof.

2. The compound according to claim 1 wherein X is O.

3. The compound according to claim 1 wherein R$^{21}$ is CF$_3$.

4. The compound according to claim 1 wherein R$^{20}$ is selected from:
a) halo, cyano or nitro;
b) R$^7$, —(C$_{1-6}$)alkylene-R$^7$, —C(=O)—R$^7$, —O—R$^7$, —C(=O)—O—R$^7$, —(C$_{1-6}$)alkylene-O—R$^7$, —S—R$^7$, —SO$_2$—R$^7$, —(C$_{1-6}$)alkylene-S—R$^7$ or —(C$_{1-6}$)alkylene-SO$_2$—R$^7$;
wherein R$^7$ is in each instance independently selected from H, (C$_{1-6}$)alkyl, (C$_{2-6}$)alkenyl, (C$_{1-6}$)haloalkyl, (C$_{3-7}$)cycloalkyl, aryl and Het; wherein the Het is a 5- or 6-membered heterocycle containing 1 to 4 heteroatoms, each independently selected from N, O and S, or Het is a 9- or 10-membered heteropolycycle containing 1 to 4 heteroatoms, each independently selected from N, O and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$; and wherein the (C$_{1-6}$)alkyl is optionally substituted with 1 or 2 substituents each independently selected from —OH, —O—(C$_{1-6}$)alkyl and COOH;
and wherein each of the aryl and Het is optionally substituted with 1 to 3 substituents each independently selected from halo, cyano, oxo, imino, —OH, —O—(C$_{1-6}$)alkyl, —NH$_2$, —NH(C$_{1-4}$)alkyl, —N((C$_{1-4}$)alkyl)$_2$, —NH—C(=O)(C$_{1-4}$)alkyl, (C$_{1-6}$)alkyl and Het, wherein the Het is a 5- or 6-membered heterocycle containing 1 to 4 heteroatoms, each independently selected from N, O and S; and
c) —N(R$^8$)R$^9$, —(C$_{1-6}$)alkylene-N(R$^8$)R$^9$ or —(C$_{1-6}$)alkylene-C(=O)—N(R$^8$)R$^9$ wherein
R$^8$ is in each instance independently selected from H and (C$_{1-6}$)alkyl; and
R$^9$ is in each instance independently selected from R$^7$, —O—(C$_{1-6}$)alkyl, —SO$_2$—R$^7$, —C(=O)—R$^7$, —C(=O)OR$^7$ and —C(=O)N(R$^8$)R$^7$; wherein R$^7$ and R$^8$ are as defined above.

5. The compound according to claim 4 wherein R$^{20}$ is selected from:
b) R$^7$, —(C$_{1-6}$)alkylene-R$^7$, —C(=O)—R$^7$, —(C$_{1-6}$)alkylene-O—R$^7$, —SO$_2$—R$^7$, —(C$_{1-6}$)alkylene-S—R$^7$ or —(C$_{1-6}$)alkylene-SO$_2$—R$^7$;
wherein R$^7$ is in each instance independently selected from H, (C$_{1-6}$)alkyl, (C$_{2-6}$)alkenyl, (C$_{1-6}$)haloalkyl, (C$_{3-7}$)cycloalkyl, aryl and Het; wherein the Het is selected from the group:

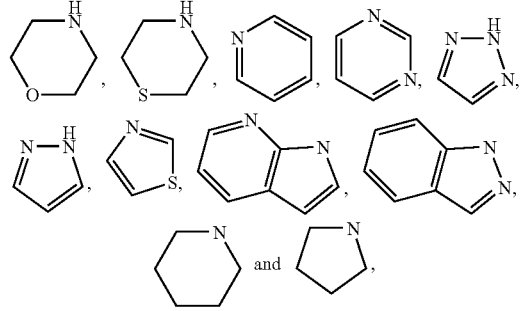

wherein the (C$_{1-6}$)alkyl is optionally substituted with 1 or 2 substituents each independently selected from —OH, —O—(C$_{1-6}$)alkyl and COOH; and wherein each of the aryl and Het is optionally substituted with 1 to 3 substituents each independently selected from halo, cyano, oxo, imino, —OH, —O—(C$_{1-6}$)alkyl, —NH$_2$, —NH(C$_{1-4}$)alkyl, —N((C$_{1-4}$)alkyl)$_2$, —NH—C(=O)(C$_{1-4}$)alkyl, (C$_{1-6}$)alkyl and Het, wherein the Het is a 5- or 6-membered heterocycle containing 1 to 4 heteroatoms, each independently selected from N, O and S; and
c) —(C$_{1-6}$)alkylene-N(R$^8$)R$^9$ or —(C$_{1-6}$)alkylene-C(=O)—N(R$^8$)R$^9$ wherein
R$^8$ is in each instance independently selected from H and (C$_{1-6}$)alkyl; and
R$^9$ is in each instance independently selected from R$^7$, —O— (C$_{1-6}$)alkyl, —SO$_2$—R$^7$, —C(=O)—R$^7$, —C(=O)OR$^7$ and —C(=O)N(R$^8$)R$^7$; wherein R$^7$ and R$^8$ are as defined above.

6. The compound according to claim 1 wherein R$^3$ is selected from H, halo and CN.

7. A compound according to claim 1 wherein R$^5$ is Het, (C$_{3-7}$)cycloalkyl or (C$_{1-6}$)alkyl, optionally substituted with (C$_{1-6}$)haloalkyl.

8. The compound according to claim 7 wherein R$^5$ is 1-methylethyl.

9. The compound according to claim 1 wherein $R^6$ is pyridinyl optionally substituted with 1 to 3 substituents each independently selected from halo, OH, $(C_{1-6})$alkyl and $(C_{1-6})$haloalkyl.

10. A pharmaceutical composition comprising a therapeutically effective amount of a compound according to claim 1, or a pharmaceutically acceptable salt or ester thereof; and one or more pharmaceutically acceptable carriers.

11. The pharmaceutical composition according to claim 10 additionally comprising at least one other antiviral agent.

* * * * *